US009809620B2

(12) United States Patent
Marciniuk et al.

(10) Patent No.: US 9,809,620 B2
(45) Date of Patent: Nov. 7, 2017

(54) PRION DISEASE-SPECIFIC EPITOPES AND METHODS OF USE THEREOF

(71) Applicant: University of Saskatchewan, Saskatoon (CA)

(72) Inventors: Kristen Marciniuk, Saskatoon (CA); Ryan Taschuk, Saskatoon (CA); Scott Napper, Saskatoon (CA); Andrew Potter, Saskatoon (CA); Neil Cashman, Saskatoon (CA)

(73) Assignee: University of Saskatchewan, Saskatchewan (CA)

(*) Notice: Subject to any disclaimer, the term of this patent is extended or adjusted under 35 U.S.C. 154(b) by 70 days.

(21) Appl. No.: 14/265,136

(22) Filed: Apr. 29, 2014

(65) Prior Publication Data

US 2015/0004185 A1 Jan. 1, 2015

Related U.S. Application Data

(60) Provisional application No. 61/817,827, filed on Apr. 30, 2013, provisional application No. 61/899,989, filed on Nov. 5, 2013.

(51) Int. Cl.

| | |
|---|---|
| *A61K 39/00* | (2006.01) |
| *C07K 14/47* | (2006.01) |
| *C07K 7/06* | (2006.01) |
| *C07K 7/08* | (2006.01) |
| *C07K 16/28* | (2006.01) |
| *C07K 16/18* | (2006.01) |
| *C07K 14/00* | (2006.01) |
| *C07K 16/44* | (2006.01) |
| *G01N 33/68* | (2006.01) |
| *C07K 14/285* | (2006.01) |

(52) U.S. Cl.

CPC ............ *C07K 7/06* (2013.01); *A61K 39/0007* (2013.01); *C07K 14/001* (2013.01); *C07K 14/285* (2013.01); *C07K 14/47* (2013.01); *C07K 16/18* (2013.01); *C07K 16/44* (2013.01); *G01N 33/6854* (2013.01); *G01N 33/6896* (2013.01); *A61K 2039/55566* (2013.01); *A61K 2039/6037* (2013.01); *C07K 2317/34* (2013.01); *C07K 2319/00* (2013.01); *C07K 2319/40* (2013.01); *C12N 2760/20134* (2013.01); *G01N 2333/001* (2013.01); *G01N 2800/24* (2013.01); *G01N 2800/2828* (2013.01)

(58) Field of Classification Search

CPC ........ A61K 2039/6037; A61K 39/0007; A61K 2039/55566; A61K 35/12; A61K 38/00; C07K 14/47; C07K 2317/34; C07K 7/06; C07K 16/2872; C07K 7/08; C07K 14/001; C07K 14/285; C07K 16/18; C07K 16/44; C07K 2319/00

See application file for complete search history.

(56) References Cited

U.S. PATENT DOCUMENTS

| | | | | | |
|---|---|---|---|---|---|
| 2002/0168377 | A1* | 11/2002 | Schaetzl | C07K 14/47 | 424/185.1 |
| 2003/0091579 | A1* | 5/2003 | Manns | A61K 39/0006 | 424/185.1 |
| 2005/0255525 | A1* | 11/2005 | Bastian | G01N 33/6896 | 435/7.1 |
| 2009/0047696 | A1* | 2/2009 | Caughey | G01N 33/6896 | 435/15 |

FOREIGN PATENT DOCUMENTS

| | | |
|---|---|---|
| EP | 1251138 | 10/2002 |
| WO | WO 93/08290 | 4/1993 |
| WO | WO 00/78344 | 12/2000 |
| WO | WO 03/040685 | 5/2003 |
| WO | WO 03/080665 | 10/2003 |

OTHER PUBLICATIONS

Bainbridge, et al., "Multiple Antigenic Peptides Facilitate Generation of Anti-Prion Antibodies," *Clin Exp Immunol* 137:298-304 (2004).

Desmezieres et al., "Lyssavirus Glycoproteins Expressing Immunologically Potent Foreign B Cell and Cytotoxic T Lymphocyte Epitopes as Prototypes for Multivalent Vaccines," *J. Gen. Virol.* (1999) 80:2343-2351.

Enari, et al., "Scrapie Prion Protein Accumulation by Scrapie-Infected Neuroblastoma Cells Abrogated by Exposure to a Prion Protein Antibody," *PNAS USA* 98:9295-9299 (2001).

Gregoire, et al., "Identification of Two Immunogenic Domains of the Prion Protein—PRP—Which Activate Class II-Restricted T Cells and Elicit Antibody Responses Against the Native Molecule," *J Leukocyte Biology* 76:125-134 (2004).

Gupta et al., "Immunogenic and Antigenic Properties of Recombinant Soluble Glycoprotein of Rabies Virus," *Vet. Microbial* 108:207-214 (2005).

Heisey et al., "Chronic Wasting Disease (CWD) Susceptibility of Several North American Rodents That Are Sympatric with Cervid CWD Epidemics," Journal of Virology, 84(1):210-215 (2010).

Highlander et al., "DNA Sequence of the Pasteurella Haemolytica Leukotoxin Gene Cluster," DNA 8:15-28 (1989).

Hedlin, et al., "Design and Delivery of a Cryptic $PRP^C$ Epitope for Induction of $PRP^{sc}$-Specific Antibody Responses," Vaccine, 28:981-988 (2010).

Lo, "Molecular Characterization of Cytotoxins Produced by Haemophilus, Actinobacillus, Pasteurella," Can J Vet Res 54:S33-S35 (1990).

Lo et al., "Nucleotide Sequence of the Leukotoxin Genes of Pasteurella Haemolytica A1," *Infect. Immun* 55(9):1987-1996 (1987).

Lo et al., "Cloning and Expression of the Leukotoxin Gene of Pasteurella Haemolytica A1 in *Escherichia coli* K-12," *Infect. Immun.* 50(3):667-671 (1985).

(Continued)

*Primary Examiner* — S. Devi

(74) *Attorney, Agent, or Firm* — Roberta L. Robins; Robins Law Group

(57) ABSTRACT

Prion peptides comprising prion epitopes and fusions thereof, that display enhanced immunogenicity are described. Also described are methods of treating and diagnosing prion disease.

17 Claims, 18 Drawing Sheets

(56) References Cited

OTHER PUBLICATIONS

Nonno et al., "Efficient Transmission and Characterization of Creutzfeldt-Jakob Disease Strains in Bank Voles," PLOS Pathogens, 2(2 e12):0112-0120 (2006).

Paramithiotis, et al., "A Prion Protein Epitope Selective for the Pathologically Misfolded Conformation," *Nat Med* 9(7):893-899 (2003).

Peretz, et al., "Antibodies Inhibit Prion Propagation and Clear Cell Cultures of Prion Infectivity," *Nature* 412:739-743 (2001).

Smith et al., "Rabies Virus Glycoprotein as a Carrier for Anthrax Protective Antigen," *Virol.* 353:344-356 (2006).
Strathdee, et al., "Extensive Homology Between the Leukotoxin of Pasteurella Haemolytica A1 and the Alpha-Hemolysin of *Escherichia coli," Infect Immun* 55(12):3233-3236 (1987).
Sui et al., "Structural and Functional Bases for Broad-Spectrum Neutralization of Avian and Human Influenza A Viruses," Nature Structural & Molecular Biology, 16(3):265-273 (2009).
Vercauteren et al., "Prion Remains Infectious after Passage through Digestive Systems of American Crows (*Corvus brachyrhynchos*)," PLOS One, 7(10):1-4 (2012).
Welch, "Pore-Forming Cytolysins of Gram-Negative Bacteria," *Mol Microbiol* 5(3):521-528 (1991).
White, et al., "Monoclonal Antibodies Inhibit Prion Replication and Delay the Development of Prion Disease," *Nature* 422:80-83 (2003).
Yokoyama, et al., "Preparation and Characterization of Antibodies Against Mouse Prion Protein (PrP) Peptides," Clin. Diagn. Lab. Immunol, 2(2):172-176 (1995).
Marciniuk, et al., "Development of a Multivalent, PrP(Sc)-Specific Prion Vaccine Through Rational Optimization of Three Disease-Specific Epitopes," Vaccine, 32(17):1998-97 (2014).

* cited by examiner

```
Sheep          1 mvkshigswilvlfvamwsdvglckkrpkpggwntggsrypggspggnryppqg------ggwgqphggwgqphgggwgqphgggwgqphgggwgqphgggwgqphgggwgqphgggg
Bovine         1 mvkshigswilvlfvamwsdvglckkrpkpggwntggsrypggspggnryppqgggggggqphgggwgqphgggwgqphgggwgqphgggwgqphgggwgqphgggwgqphgggg
Human          1 --manlgcwmlvlfvatwsdlglckkrpkp-ggwntggsrypggspggnryppqg--------ggwgqphgggwgqphgggwgqphgggwgqphgggph-ggg
Mouse          1 --manlgywllalfvtmwtdvglckkrpkp-ggwntggsrypggspggnryppqg--------ggtwgqphgggwgqphggswgqphgggwgqphgggwgqph-ggg
Elk            1 mvkshigswilvlfvamwsdvglckkrpkpggwntggsrypggspggnryppqg--------gggwgqphgggwgqphgggwgqphgggwgqphgggwgqphgggg
Mule Deer      1 mvkshigswilvlfvamwsdvglckkrpkpggwntggsrypggspggnryppqg--------gggwgqphgggwgqphgggwgqphgggwgqphgggwgqphgggg
Whitetail Deer 1 mvkshigswilvlfvamwsdvglckkrpkpggwntggsrypggspggnryppqg--------gggwgqphgggwgqphgggwgqphgggwgqphgggwgqphgggg Sheep          93 wgq-ggshsqwnkpskpktnmkhvagaaaagavvgglggymlgsamsrplihfgndyedryyrenmyrypnqvyyrpvdqysnqnfvhdcvnitvkqht
Bovine        101 wgq-ggthgqwnkpskpktnmkhvagaaaagavvgglggymlgsamsrplihfgxdyedryyrenmhrypnqvyyrpvdqysnqnfvhdcvnitvkeht
Human          89 wgqggthsqwnkpskpktnmkhmagaaaagavvgglggyvlgsamsrpliihfgsdyedryyrenmhrypnqvyyrpmdeysnqnfvhdcvnitikqht
Mouse          88 wggggthnqwnkpskpktnlkhvagaaaagavvgglggymlgsamsrpmihfgndwedryyrenmyrypnqvyyrpvdqysnqnfvhdcvnitikqht
Elk            93 wgq-ggthsqwnkpskpktnmkhvagaaaagavvgglggymlgsamsrplihfgndyedryyrenmyrypnqvyyrpvdqymqntfvhdcvnitvkqht
Mule Deer      93 wgq-ggthsqwnkpskpktnmkhvagaaaagavvgglggymlgsamsrplihfgndyedryyrenmyrypnqvyyrpvdqymqntfvhdcvnitvkqht
Whitetail Deer 93 wgq-ggthsqwnkpskpktnmkhvagaaaagavvgglggymlgsamsrplihfgndyedryyrenmyrypnqvyyrpvdqymqntfvhdcvnitvkqht Sheep         192 vttttkgenftetdikimervveqmcitqyqresqayy--qrgasvilfssppvillisflifliivg
Bovine        200 vttttkgenftetdikmmervveqmcitqyqresqayy--qrgasvilfssppvillisflifliivg
Human         189 vttttkgenftetdvkmmervveqmcitqyeresqayy--qrgssmvlfssppvillisflifliivg
Mouse         188 vttttkgenftetdvkmmervveqmcvtqyqkesqayydgrrsssstvlfssppvillisflifliivg
Elk           192 vttttkgenftetdikmmervveqmcitqyqreseayy--qrgasvilfssppvillisflifliivg
Mule Deer     192 vttttkgenftetdikmmervveqmcitqyqresqayy--qrgasvilfssppvillisflifliivg
Whitetail Deer192 vttttkgenftetdikmmervveqmcitqyqresqayy--qrgasvilfssppvillisflifliivg
```

Fig. 1

```
              10          20          30          40          50          60
     *     *     *     *     *     *     *     *     *     *     *     *
ATG GCT ACT GTT ATA GAT CTA AGC TTC CCA AAA ACT GGG GCA AAA AAA ATT ATC CTC TAT
TAC CGA TGA CAA TAT CTA GAT TCG AAG GGT TTT TGA CCC CGT TTT TTT TAA TAG GAG ATA
Met Ala Thr Val Ile Asp Leu Ser Phe Pro Lys Thr Gly Ala Lys Lys Ile Ile Leu Tyr>
___c___c___c___c___c_____RECOMBINANT LEUKOTOXIN PEPTIDE_c___c___c___c___c___c___>
___a___a____VECTOR SEQUENCE_a___a___a__>

70          80          90         100         110         120
     *     *     *     *     *     *     *     *     *     *     *     *
ATT CCC CAA AAT TAC CAA TAT GAT ACT GAA CAA GGT AAT GGT TTA CAG GAT TTA GTC AAA
TAA GGG GTT TTA ATG GTT ATA CTA TGA CTT GTT CCA TTA CCA AAT GTC CTA AAT CAG TTT
Ile Pro Gln Asn Tyr Gln Tyr Asp Thr Glu Gln Gly Asn Gly Leu Gln Asp Leu Val Lys>
___c___c___c___c___c_____RECOMBINANT LEUKOTOXIN PEPTIDE_c___c___c___c___c___c___>

130         140         150         160         170         180
     *     *     *     *     *     *     *     *     *     *     *     *
GCG GCC GAA GAG TTG GGG ATT GAG GTA CAA AGA GAA GAA CGC AAT AAT ATT GCA ACA GCT
CGC CGG CTT CTC AAC CCC TAA CTC CAT GTT TCT CTT CTT GCG TTA TTA TAA CGT TGT CGA
Ala Ala Glu Glu Leu Gly Ile Glu Val Gln Arg Glu Glu Arg Asn Asn Ile Ala Thr Ala>
___c___c___c___c___c_____RECOMBINANT LEUKOTOXIN PEPTIDE_c___c___c___c___c___c___>

190         200         210         220         230         240
     *     *     *     *     *     *     *     *     *     *     *     *
CAA ACC AGT TTA GGC ACG ATT CAA ACC GCT ATT GGC TTA ACT GAG CGT GGC ATT GTG TTA
GTT TGG TCA AAT CCG TGC TAA GTT TGG CGA TAA CCG AAT TGA CTC GCA CCG TAA CAC AAT
Gln Thr Ser Leu Gly Thr Ile Gln Thr Ala Ile Gly Leu Thr Glu Arg Gly Ile Val Leu>
___c___c___c___c___c_____RECOMBINANT LEUKOTOXIN PEPTIDE_c___c___c___c___c___c___>

250         260         270         280         290         300
     *     *     *     *     *     *     *     *     *     *     *     *
TCC GCT CCA CAA ATT GAT AAA TTG CTA CAG AAA ACT AAA GCA GGC CAA GCA TTA GGT TCT
AGG CGA GGT GTT TAA CTA TTT AAC GAT GTC TTT TGA TTT CGT CCG GTT CGT AAT CCA AGA
Ser Ala Pro Gln Ile Asp Lys Leu Leu Gln Lys Thr Lys Ala Gly Gln Ala Leu Gly Ser>
___c___c___c___c___c_____RECOMBINANT LEUKOTOXIN PEPTIDE_c___c___c___c___c___c___>

310         320         330         340         350         360
     *     *     *     *     *     *     *     *     *     *     *     *
GCC GAA AGC ATT GTA CAA AAT GCA AAT AAA GCC AAA ACT GTA TTA TCT GGC ATT CAA TCT
CGG CTT TCG TAA CAT GTT TTA CGT TTA TTT CGG TTT TGA CAT AAT AGA CCG TAA GTT AGA
Ala Glu Ser Ile Val Gln Asn Ala Asn Lys Ala Lys Thr Val Leu Ser Gly Ile Gln Ser>
___c___c___c___c___c_____RECOMBINANT LEUKOTOXIN PEPTIDE_c___c___c___c___c___c___>

370         380         390         400         410         420
     *     *     *     *     *     *     *     *     *     *     *     *
ATT TTA GGC TCA GTA TTG GCT GGA ATG GAT TTA GAT GAG GCC TTA CAG AAT AAC AGC AAC
TAA AAT CCG AGT CAT AAC CGA CCT TAC CTA AAT CTA CTC CGG AAT GTC TTA TTG TCG TTG
Ile Leu Gly Ser Val Leu Ala Gly Met Asp Leu Asp Glu Ala Leu Gln Asn Asn Ser Asn>
___c___c___c___c___c_____RECOMBINANT LEUKOTOXIN PEPTIDE_c___c___c___c___c___c___>

430         440         450         460         470         480
     *     *     *     *     *     *     *     *     *     *     *     *
CAA CAT GCT CTT GCT AAA GCT GGC TTG GAG CTA ACA AAT TCA TTA ATT GAA AAT ATT GCT
GTT GTA CGA GAA CGA TTT CGA CCG AAC CTC GAT TGT TTA AGT AAT TAA CTT TTA TAA CGA
Gln His Ala Leu Ala Lys Ala Gly Leu Glu Leu Thr Asn Ser Leu Ile Glu Asn Ile Ala>
___c___c___c___c___c_____RECOMBINANT LEUKOTOXIN PEPTIDE_c___c___c___c___c___c___>
```

FIG. 3A

```
          490         500         510         520         530         540
           *           *           *           *           *           *
AAT TCA GTA AAA ACA CTT GAC GAA TTT GGT GAG CAA ATT AGT CAA TTT GGT TCA AAA CTA
TTA AGT CAT TTT TGT GAA CTG CTT AAA CCA CTC GTT TAA TCA GTT AAA CCA AGT TTT GAT
Asn Ser Val Lys Thr Leu Asp Glu Phe Gly Glu Gln Ile Ser Gln Phe Gly Ser Lys Leu>
___c___c___c___c___c_____RECOMBINANT LEUKOTOXIN PEPTIDE_c___c___c___c___c___c___>

550         560         570         580         590         600
           *           *           *           *           *           *
CAA AAT ATC AAA GGC TTA GGG ACT TTA GGA GAC AAA CTC AAA AAT ATC GGT GGA CTT GAT
GTT TTA TAG TTT CCG AAT CCC TGA AAT CCT CTG TTT GAG TTT TTA TAG CCA CCT GAA CTA
Gln Asn Ile Lys Gly Leu Gly Thr Leu Gly Asp Lys Leu Lys Asn Ile Gly Gly Leu Asp>
___c___c___c___c___c_____RECOMBINANT LEUKOTOXIN PEPTIDE_c___c___c___c___c___c___>

610         620         630         640         650         660
           *           *           *           *           *           *
AAA GCT GGC CTT GGT TTA GAT GTT ATC TCA GGG CTA TTA TCG GGC GCA ACA GCT GCA CTT
TTT CGA CCG GAA CCA AAT CTA CAA TAG AGT CCC GAT AAT AGC CCG CGT TGT CGA CGT GAA
Lys Ala Gly Leu Gly Leu Asp Val Ile Ser Gly Leu Leu Ser Gly Ala Thr Ala Ala Leu>
___c___c___c___c___c_____RECOMBINANT LEUKOTOXIN PEPTIDE_c___c___c___c___c___c___>

670         680         690         700         710         720
           *           *           *           *           *           *
GTA CTT GCA GAT AAA AAT GCT TCA ACA GCT AAA AAA GTG GGT GCG GGT TTT GAA TTG GCA
CAT GAA CGT CTA TTT TTA CGA AGT TGT CGA TTT TTT CAC CCA GCG CCA AAA CTT AAC CGT
Val Leu Ala Asp Lys Asn Ala Ser Thr Ala Lys Lys Val Gly Ala Gly Phe Glu Leu Ala>
___c___c___c___c___c_____RECOMBINANT LEUKOTOXIN PEPTIDE_c___c___c___c___c___c___>

730         740         750         760         770         780
           *           *           *           *           *           *
AAC CAA GTT GTT GGT AAT ATT ACC AAA GCC GTT TCT TCT TAC ATT TTA GCC CAA CGT GTT
TTG GTT CAA CAA CCA TTA TAA TGG TTT CGG CAA AGA AGA ATG TAA AAT CGG GTT GCA CAA
Asn Gln Val Val Gly Asn Ile Thr Lys Ala Val Ser Ser Tyr Ile Leu Ala Gln Arg Val>
___c___c___c___c___c_____RECOMBINANT LEUKOTOXIN PEPTIDE_c___c___c___c___c___c___>

790         800         810         820         830         840
           *           *           *           *           *           *
GCA GCA GGT TTA TCT TCA ACT GGG CCT GTG GCT GCT TTA ATT GCT TCT ACT GTT TCT CTT
CGT CGT CCA AAT AGA AGT TGA CCC GGA CAC CGA CGA AAT TAA CGA AGA TGA CAA AGA GAA
Ala Ala Gly Leu Ser Ser Thr Gly Pro Val Ala Ala Leu Ile Ala Ser Thr Val Ser Leu>
___c___c___c___c___c_____RECOMBINANT LEUKOTOXIN PEPTIDE_c___c___c___c___c___c___>

850         860         870         880         890         900
           *           *           *           *           *           *
GCG ATT AGC CCA TTA GCA TTT GCC GGT ATT GCC GAT AAA TTT AAT CAT GCA AAA AGT TTA
CGC TAA TCG GGT AAT CGT AAA CGG CCA TAA CGG CTA TTT AAA TTA GTA CGT TTT TCA AAT
Ala Ile Ser Pro Leu Ala Phe Ala Gly Ile Ala Asp Lys Phe Asn His Ala Lys Ser Leu>
___c___c___c___c___c_____RECOMBINANT LEUKOTOXIN PEPTIDE_c___c___c___c___c___c___>

910         920         930         940         950         960
           *           *           *           *           *           *
GAG AGT TAT GCC GAA CGC TTT AAA AAA TTA GGC TAT GAC GGA GAT AAT TTA TTA GCA GAA
CTC TCA ATA CGG CTT GCG AAA TTT TTT AAT CCG ATA CTG CCT CTA TTA AAT AAT CGT CTT
Glu Ser Tyr Ala Glu Arg Phe Lys Lys Leu Gly Tyr Asp Gly Asp Asn Leu Leu Ala Glu>
___c___c___c___c___c_____RECOMBINANT LEUKOTOXIN PEPTIDE_c___c___c___c___c___c___>
```

FIG. 3B

```
               970         980         990        1000        1010        1020
                 *           *           *           *           *           *
TAT CAG CGG GGA ACA GGG ACT ATT GAT GCA TCG GTT ACT GCA ATT AAT ACC GCA TTG GCC
ATA GTC GCC CCT TGT CCC TGA TAA CTA CGT AGC CAA TGA CGT TAA TTA TGG CGT AAC CGG
Tyr Gln Arg Gly Thr Gly Thr Ile Asp Ala Ser Val Thr Ala Ile Asn Thr Ala Leu Ala>
___c____c____c____c____c____RECOMBINANT LEUKOTOXIN PEPTIDE_c____c____c____c____c____c___>

1030        1040        1050        1060        1070        1080
                 *           *           *           *           *           *
GCT ATT GCT GGT GGT GTG TCT GCT GCT GCA GCC GGC TCG GTT ATT GCT TCA CCG ATT GCC
CGA TAA CGA CCA CCA CAC AGA CGA CGA CGT CGG CCG AGC CAA TAA CGA AGT GGC TAA CGG
Ala Ile Ala Gly Gly Val Ser Ala Ala Ala Ala Gly Ser Val Ile Ala Ser Pro Ile Ala>
___c____c____c____c____c____RECOMBINANT LEUKOTOXIN PEPTIDE_c____c____c____c____c____c___>

1090        1100        1110        1120        1130        1140
                 *           *           *           *           *           *
TTA TTA GTA TCT GGG ATT ACC GGT GTA ATT TCT ACG ATT CTG CAA TAT TCT AAA CAA GCA
AAT AAT CAT AGA CCC TAA TGG CCA CAT TAA AGA TGC TAA GAC GTT ATA AGA TTT GTT CGT
Leu Leu Val Ser Gly Ile Thr Gly Val Ile Ser Thr Ile Leu Gln Tyr Ser Lys Gln Ala>
___c____c____c____c____c____RECOMBINANT LEUKOTOXIN PEPTIDE_c____c____c____c____c____c___>

1150        1160        1170        1180        1190        1200
                 *           *           *           *           *           *
ATG TTT GAG CAC GTT GCA AAT AAA ATT CAT AAC AAA ATT GTA GAA TGG GAA AAA AAT AAT
TAC AAA CTC GTG CAA CGT TTA TTT TAA GTA TTG TTT TAA CAT CTT ACC CTT TTT TTA TTA
Met Phe Glu His Val Ala Asn Lys Ile His Asn Lys Ile Val Glu Trp Glu Lys Asn Asn>
___c____c____c____c____c____RECOMBINANT LEUKOTOXIN PEPTIDE_c____c____c____c____c____c___>

1210        1220        1230        1240        1250        1260
                 *           *           *           *           *           *
CAC GGT AAG AAC TAC TTT GAA AAT GGT TAC GAT GCC CGT TAT CTT GCG AAT TTA CAA GAT
GTG CCA TTC TTG ATG AAA CTT TTA CCA ATG CTA CGG GCA ATA GAA CGC TTA AAT GTT CTA
His Gly Lys Asn Tyr Phe Glu Asn Gly Tyr Asp Ala Arg Tyr Leu Ala Asn Leu Gln Asp>
___c____c____c____c____c____RECOMBINANT LEUKOTOXIN PEPTIDE_c____c____c____c____c____c___>

1270        1280        1290        1300        1310        1320
                 *           *           *           *           *           *
AAT ATG AAA TTC TTA CTG AAC TTA AAC AAA GAG TTA CAG GCA GAA CGT GTC ATC GCT ATT
TTA TAC TTT AAG AAT GAC TTG AAT TTG TTT CTC AAT GTC CGT CTT GCA CAG TAG CGA TAA
Asn Met Lys Phe Leu Leu Asn Leu Asn Lys Glu Leu Gln Ala Glu Arg Val Ile Ala Ile>
___c____c____c____c____c____RECOMBINANT LEUKOTOXIN PEPTIDE_c____c____c____c____c____c___>

1330        1340        1350        1360        1370        1380
                 *           *           *           *           *           *
ACT CAG CAG CAA TGG GAT AAC AAC ATT GGT GAT TTA GCT GGT ATT AGC CGT TTA GGT GAA
TGA GTC GTC GTT ACC CTA TTG TTG TAA CCA CTA AAT CGA CCA TAA TCG GCA AAT CCA CTT
Thr Gln Gln Gln Trp Asp Asn Asn Ile Gly Asp Leu Ala Gly Ile Ser Arg Leu Gly Glu>
___c____c____c____c____c____RECOMBINANT LEUKOTOXIN PEPTIDE_c____c____c____c____c____c___>

1390        1400        1410        1420        1430        1440
                 *           *           *           *           *           *
AAA GTC CTT AGT GGT AAA GCC TAT GTG GAT GCG TTT GAA GAA GGC AAA CAC ATT AAA GCC
TTT CAG GAA TCA CCA TTT CGG ATA CAC CTA CGC AAA CTT CTT CCG TTT GTG TAA TTT CGG
Lys Val Leu Ser Gly Lys Ala Tyr Val Asp Ala Phe Glu Glu Gly Lys His Ile Lys Ala>
___c____c____c____c____c____RECOMBINANT LEUKOTOXIN PEPTIDE_c____c____c____c____c____c___>
```

FIG. 3C

```
              1450        1460        1470        1480        1490        1500
          *     *     *     *     *     *     *     *     *     *     *     *
       GAT AAA TTA GTA CAG TTG GAT TCG GCA AAC GGT ATT ATT GAT GTG AGT AAT TCG GGT AAA
       CTA TTT AAT CAT GTC AAC CTA AGC CGT TTG CCA TAA TAA CTA CAC TCA TTA AGC CCA TTT
       Asp Lys Leu Val Gln Leu Asp Ser Ala Asn Gly Ile Ile Asp Val Ser Asn Ser Gly Lys>

1510        1520        1530        1540        1550        1560
          *     *     *     *     *     *     *     *     *     *     *     *
       GCG AAA ACT CAG CAT ATC TTA TTC AGA ACG CCA TTA TTG ACG CCG GGA ACA GAG CAT CGT
       CGC TTT TGA GTC GTA TAG AAT AAG TCT TGC GGT AAT AAC TGC GGC CCT TGT CTC GTA GCA
       Ala Lys Thr Gln His Ile Leu Phe Arg Thr Pro Leu Leu Thr Pro Gly Thr Glu His Arg>
         c    c    c    c    c   RECOMBINANT LEUKOTOXIN PEPTIDE_c    c    c    c    c    c   >

1570        1580        1590        1600        1610        1620
          *     *     *     *     *     *     *     *     *     *     *     *
       GAA CGC GTA CAA ACA GGT AAA TAT GAA TAT ATT ACC AAG CTC AAT ATT AAC CGT GTA GAT
       CTT GCG CAT GTT TGT CCA TTT ATA CTT ATA TAA TGG TTC GAG TTA TAA TTG GCA CAT CTA
       Glu Arg Val Gln Thr Gly Lys Tyr Glu Tyr Ile Thr Lys Leu Asn Ile Asn Arg Val Asp>
         c    c    c    c    c   RECOMBINANT LEUKOTOXIN PEPTIDE_c    c    c    c    c    c   >

1630        1640        1650        1660        1670        1680
          *     *     *     *     *     *     *     *     *     *     *     *
       AGC TGG AAA ATT ACA GAT GGT GCA GCA AGT TCT ACC TTT GAT TTA ACT AAC GTT GTT CAG
       TCG ACC TTT TAA TGT CTA CCA CGT CGT TCA AGA TGG AAA CTA AAT TGA TTG CAA CAA GTC
       Ser Trp Lys Ile Thr Asp Gly Ala Ala Ser Ser Thr Phe Asp Leu Thr Asn Val Val Gln>
         c    c    c    c    c   RECOMBINANT LEUKOTOXIN PEPTIDE_c    c    c    c    c    c   >

1690        1700        1710        1720        1730        1740
          *     *     *     *     *     *     *     *     *     *     *     *
       CGT ATT GGT ATT GAA TTA GAC AAT GCT GGA AAT GTA ACT AAA ACC AAA GAA ACA AAA ATT
       GCA TAA CCA TAA CTT AAT CTG TTA CGA CCT TTA CAT TGA TTT TGG TTT CTT TGT TTT TAA
       Arg Ile Gly Ile Glu Leu Asp Asn Ala Gly Asn Val Thr Lys Thr Lys Glu Thr Lys Ile>
         c    c    c    c    c   RECOMBINANT LEUKOTOXIN PEPTIDE_c    c    c    c    c    c   >

1750        1760        1770        1780        1790        1800
          *     *     *     *     *     *     *     *     *     *     *     *
       ATT GCC AAA CTT GGT GAA GGT GAT GAC AAC GTA TTT GTT GGT TCT GGT ACG ACG GAA ATT
       TAA CGG TTT GAA CCA CTT CCA CTA CTG TTG CAT AAA CAA CCA AGA CCA TGC TGC CTT TAA
       Ile Ala Lys Leu Gly Glu Gly Asp Asp Asn Val Phe Val Gly Ser Gly Thr Thr Glu Ile>
         c    c    c    c    c   RECOMBINANT LEUKOTOXIN PEPTIDE_c    c    c    c    c    c   >

1810        1820        1830        1840        1850        1860
          *     *     *     *     *     *     *     *     *     *     *     *
       GAT GGC GGT GAA GGT TAC GAC CGA GTT CAC TAT AGC CGT GGA AAC TAT GGT GCT TTA ACT
       CTA CCG CCA CTT CCA ATG CTG GCT CAA GTG ATA TCG GCA CCT TTG ATA CCA CGA AAT TGA
       Asp Gly Gly Glu Gly Tyr Asp Arg Val His Tyr Ser Arg Gly Asn Tyr Gly Ala Leu Thr>
         c    c    c    c    c   RECOMBINANT LEUKOTOXIN PEPTIDE_c    c    c    c    c    c   >

1870        1880        1890        1900        1910        1920
          *     *     *     *     *     *     *     *     *     *     *     *
       ATT GAT GCA ACC AAA GAG ACC GAG CAA GGT AGT TAT ACC GTA AAT CGT TTC GTA GAA ACC
       TAA CTA CGT TGG TTT CTC TGG CTC GTT CCA TCA ATA TGG CAT TTA GCA AAG CAT CTT TGG
       Ile Asp Ala Thr Lys Glu Thr Glu Gln Gly Ser Tyr Thr Val Asn Arg Phe Val Glu Thr>
         c    c    c    c    c   RECOMBINANT LEUKOTOXIN PEPTIDE_c    c    c    c    c    c   >
```

FIG. 3D

```
              1930          1940          1950          1960          1970          1980
          *     *       *     *       *     *       *     *       *     *       *     *
     GGT AAA GCA CTA CAC GAA GTG ACT TCA ACC CAT ACC GCA TTA GTG GGC AAC CGT GAA GAA
     CCA TTT CGT GAT GTG CTT CAC TGA AGT TGG GTA TGG CGT AAT CAC CCG TTG GCA CTT CTT
     Gly Lys Ala Leu His Glu Val Thr Ser Thr His Thr Ala Leu Val Gly Asn Arg Glu Glu>
     __c___c___c___c___c____RECOMBINANT LEUKOTOXIN PEPTIDE_c____c____c____c____c____c___>

1990          2000          2010          2020          2030          2040
          *     *       *     *       *     *       *     *       *     *       *     *
     AAA ATA GAA TAT CGT CAT AGC AAT AAC CAG CAC CAT GCC GGT TAT TAC ACC AAA GAT ACC
     TTT TAT CTT ATA GCA GTA TCG TTA TTG GTC GTG GTA CGG CCA ATA ATG TGG TTT CTA TGG
     Lys Ile Glu Tyr Arg His Ser Asn Asn Gln His His Ala Gly Tyr Tyr Thr Lys Asp Thr>
     __c___c___c___c___c____RECOMBINANT LEUKOTOXIN PEPTIDE_c____c____c____c____c____c___>

2050          2060          2070          2080          2090          2100
          *     *       *     *       *     *       *     *       *     *       *     *
     TTG AAA GCT GTT GAA GAA ATT ATC GGT ACA TCA CAT AAC GAT ATC TTT AAA GGT AGT AAG
     AAC TTT CGA CAA CTT CTT TAA TAG CCA TGT AGT GTA TTG CTA TAG AAA TTT CCA TCA TTC
     Leu Lys Ala Val Glu Glu Ile Ile Gly Thr Ser His Asn Asp Ile Phe Lys Gly Ser Lys>
     __c___c___c___c___c____RECOMBINANT LEUKOTOXIN PEPTIDE_c____c____c____c____c____c___>

2110          2120          2130          2140          2150          2160
          *     *       *     *       *     *       *     *       *     *       *     *
     TTC AAT GAT GCC TTT AAC GGT GGT GAT GGT GTC GAT ACT ATT GAC GGT AAC GAC GGC AAT
     AAG TTA CTA CGG AAA TTG CCA CCA CTA CCA CAG CTA TGA TAA CTG CCA TTG CTG CCG TTA
     Phe Asn Asp Ala Phe Asn Gly Gly Asp Gly Val Asp Thr Ile Asp Gly Asn Asp Gly Asn>
     __c___c___c___c___c____RECOMBINANT LEUKOTOXIN PEPTIDE_c____c____c____c____c____c___>

2170          2180          2190          2200          2210          2220
          *     *       *     *       *     *       *     *       *     *       *     *
     GAC CGC TTA TTT GGT GGT AAA GGC GAT GAT ATT CTC GAT GGT GGA AAT GGT GAT GAT TTT
     CTG GCG AAT AAA CCA CCA TTT CCG CTA CTA TAA GAG CTA CCA CCT TTA CCA CTA CTA AAA
     Asp Arg Leu Phe Gly Gly Lys Gly Asp Asp Ile Leu Asp Gly Gly Asn Gly Asp Asp Phe>
     __c___c___c___c___c____RECOMBINANT LEUKOTOXIN PEPTIDE_c____c____c____c____c____c___>

2230          2240          2250          2260          2270          2280
          *     *       *     *       *     *       *     *       *     *       *     *
     ATC GAT GGC GGT AAA GGC AAC GAC CTA TTA CAC GGT GGC AAG GGC GAT GAT ATT TTC GTT
     TAG CTA CCG CCA TTT CCG TTG CTG GAT AAT GTG CCA CCG TTC CCG CTA CTA TAA AAG CAA
     Ile Asp Gly Gly Lys Gly Asn Asp Leu Leu His Gly Gly Lys Gly Asp Asp Ile Phe Val>
     __c___c___c___c___c____RECOMBINANT LEUKOTOXIN PEPTIDE_c____c____c____c____c____c___>

2290          2300          2310          2320          2330          2340
          *     *       *     *       *     *       *     *       *     *       *     *
     CAC CGT AAA GGC GAT GGT AAT GAT ATT ATT ACC GAT TCT GAC GGC AAT GAT AAA TTA TCA
     GTG GCA TTT CCG CTA CCA TTA CTA TAA TAA TGG CTA AGA CTG CCG TTA CTA TTT AAT AGT
     His Arg Lys Gly Asp Gly Asn Asp Ile Ile Thr Asp Ser Asp Gly Asn Asp Lys Leu Ser>
     __c___c___c___c___c____RECOMBINANT LEUKOTOXIN PEPTIDE_c____c____c____c____c____c___>

2350          2360          2370          2380          2390          2400
          *     *       *     *       *     *       *     *       *     *       *     *
     TTC TCT GAT TCG AAC TTA AAA GAT TTA ACA TTT GAA AAA GTT AAA CAT AAT CTT GTC ATC
     AAG AGA CTA AGC TTG AAT TTT CTA AAT TGT AAA CTT TTT CAA TTT GTA TTA GAA CAG TAG
     Phe Ser Asp Ser Asn Leu Lys Asp Leu Thr Phe Glu Lys Val Lys His Asn Leu Val Ile>
     __c___c___c___c___c____RECOMBINANT LEUKOTOXIN PEPTIDE_c____c____c____c____c____c___>
```

FIG. 3E

```
         2410        2420        2430        2440        2450        2460
      *        *        *        *        *        *        *        *        *        *        *        *
ACG AAT AGC AAA AAA GAG AAA GTG ACC ATT CAA AAC TGG TTC CGA GAG GCT GAT TTT GCT
TGC TTA TCG TTT TTT CTC TTT CAC TGG TAA GTT TTG ACC AAG GCT CTC CGA CTA AAA CGA
Thr Asn Ser Lys Lys Glu Lys Val Thr Ile Gln Asn Trp Phe Arg Glu Ala Asp Phe Ala>
 __c___c___c___c___c____RECOMBINANT LEUKOTOXIN PEPTIDE_c___c___c___c___c___c___>

2470        2480        2490        2500        2510        2520
      *        *        *        *        *        *        *        *        *        *        *        *
AAA GAA GTG CCT AAT TAT AAA GCA ACT AAA GAT GAG AAA ATC GAA GAA ATC ATC GGT CAA
TTT CTT CAC GGA TTA ATA TTT CGT TGA TTT CTA CTC TTT AAG CTT CTT TAG TAG CCA GTT
Lys Glu Val Pro Asn Tyr Lys Ala Thr Lys Asp Glu Lys Ile Glu Glu Ile Ile Gly Gln>
 __c___c___c___c___c____RECOMBINANT LEUKOTOXIN PEPTIDE_c___c___c___c___c___c___>

2530        2540        2550        2560        2570        2580
      *        *        *        *        *        *        *        *        *        *        *        *
AAT GGC GAG CGG ATC ACC TCA AAG CAA GTT GAT GAT CTT ATC GCA AAA GGT AAC GGC AAA
TTA CCG CTC GCC TAG TGG AGT TTC GTT CAA CTA CTA GAA TAG CGT TTT CCA TTG CCG TTT
Asn Gly Glu Arg Ile Thr Ser Lys Gln Val Asp Asp Leu Ile Ala Lys Gly Asn Gly Lys>
 __c___c___c___c___c____RECOMBINANT LEUKOTOXIN PEPTIDE_c___c___c___c___c___c___>

2590        2600        2610        2620        2630        2640
      *        *        *        *        *        *        *        *        *        *        *        *
ATT ACC CAA GAT GAG CTA TCA AAA GTT GTT GAT AAC TAT GAA TTG CTC AAA CAT AGC AAA
TAA TGG GTT CTA CTC GAT AGT TTT CAA CAA CTA TTG ATA CTT AAC GAG TTT GTA TCG TTT
Ile Thr Gln Asp Glu Leu Ser Lys Val Val Asp Asn Tyr Glu Leu Leu Lys His Ser Lys>
 __c___c___c___c___c____RECOMBINANT LEUKOTOXIN PEPTIDE_c___c___c___c___c___c___>

2650        2660        2670        2680        2690        2700
      *        *        *        *        *        *        *        *        *        *        *        *
AAT GTG ACA AAC AGC TTA GAT AAG TTA ATC TCA TCT GTA AGT GCA TTT ACC TCG TCT AAT
TTA CAC TGT TTG TCG AAT CTA TTC AAT TAG AGT AGA CAT TCA CGT AAA TGG AGC AGA TTA
Asn Val Thr Asn Ser Leu Asp Lys Leu Ile Ser Ser Val Ser Ala Phe Thr Ser Ser Asn>
 __c___c___c___c___c____RECOMBINANT LEUKOTOXIN PEPTIDE_c___c___c___c___c___c___>

2710        2720        2730        2740        2750        2760
      *        *        *        *        *        *        *        *        *        *        *        *
GAT TCG AGA AAT GTA TTA GTG GCT CCA ACT TCA ATG TTG GAT CAA AGT TTA TCT TCT CTT
CTA AGC TCT TTA CAT AAT CAC CGA GGT TGA AGT TAC AAC CTA GTT TCA AAT AGA AGA GAA
Asp Ser Arg Asn Val Leu Val Ala Pro Thr Ser Met Leu Asp Gln Ser Leu Ser Ser Leu>
 __c___c___c___c___c____RECOMBINANT LEUKOTOXIN PEPTIDE_c___c___c___c___c___c___>

2770        2780        2790
      *        *        *        *        *        *
CAA TTT GCT AGG GGA TCC TAG CTAGCTAGCCATG
GTT AAA CGA TCC CCT AGG ATC GATCGATCGGTAC
Gln Phe Ala Arg Gly Ser End>
 ____RECOMBINANT LEUKOTOX____>
             __b____VECTOR SEQUENCE_____>
```

FIG. 3F

A)
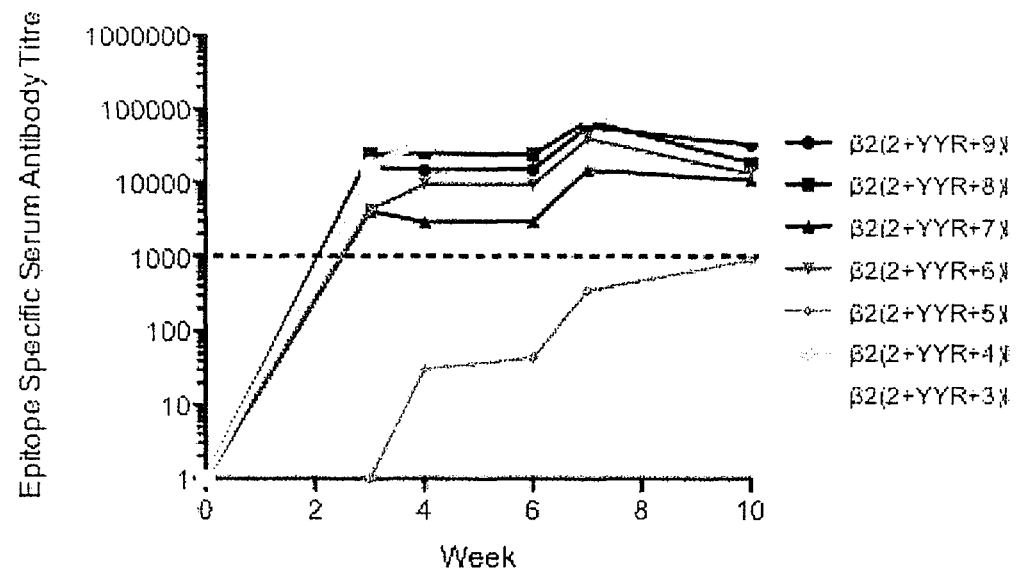
B)
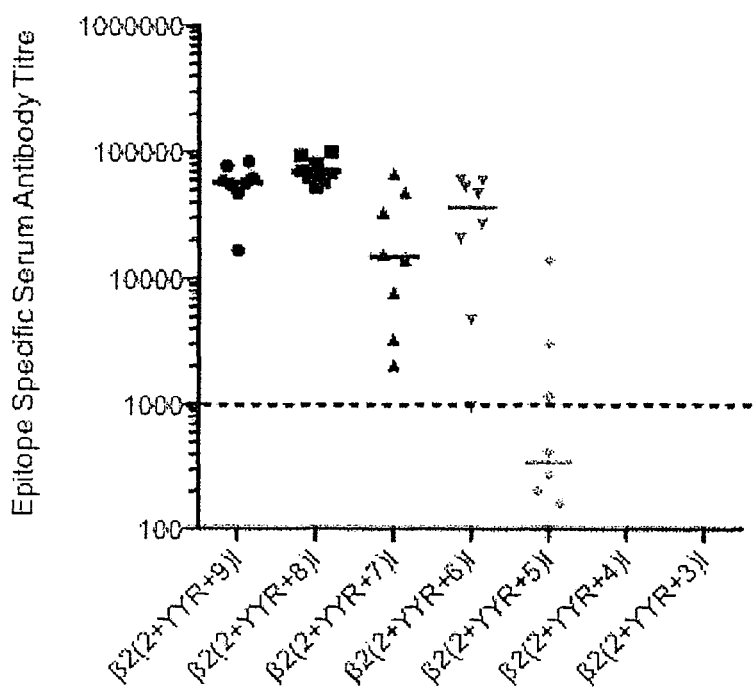
FIGURE 4

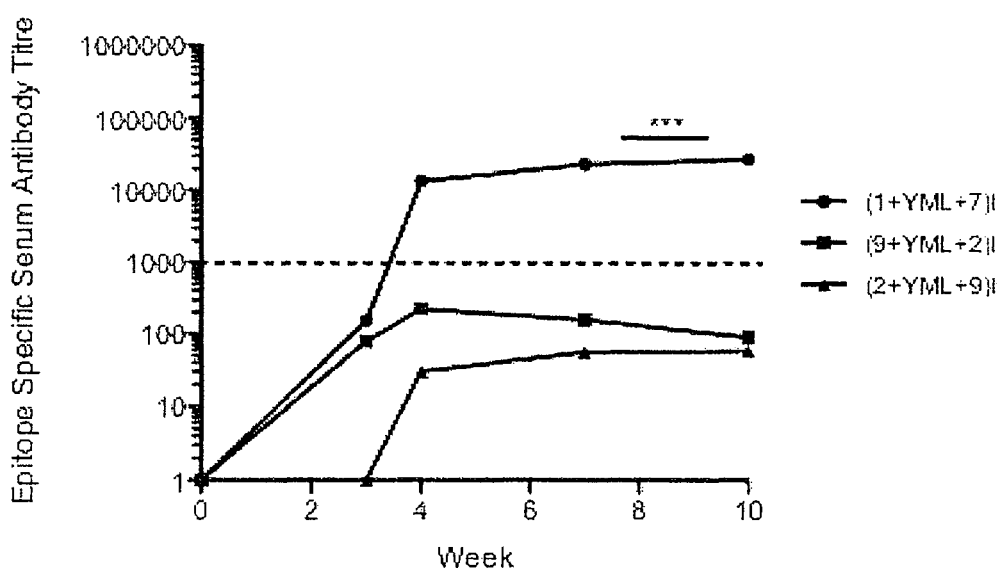
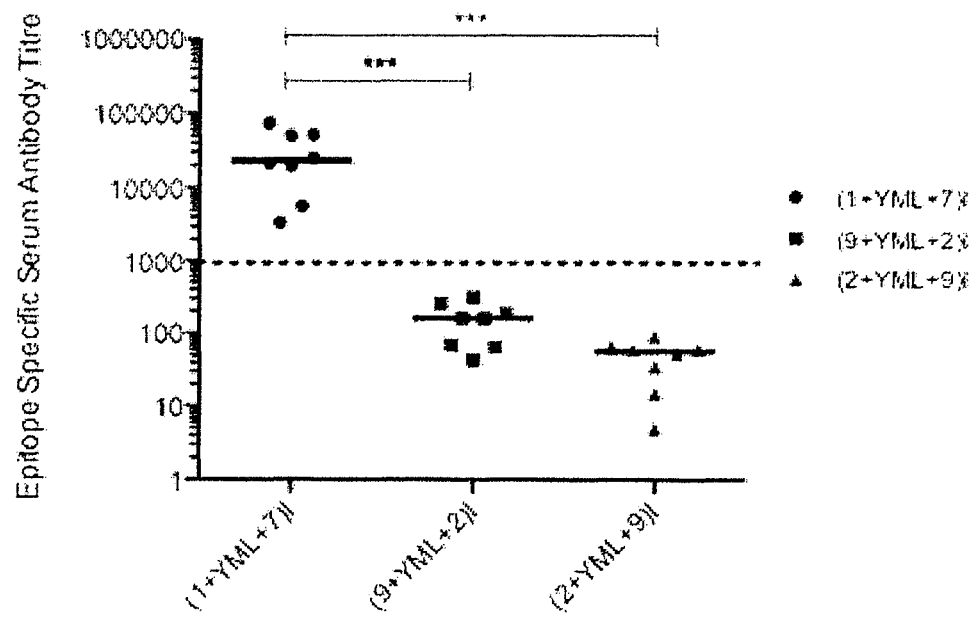
FIGURE 5

B)
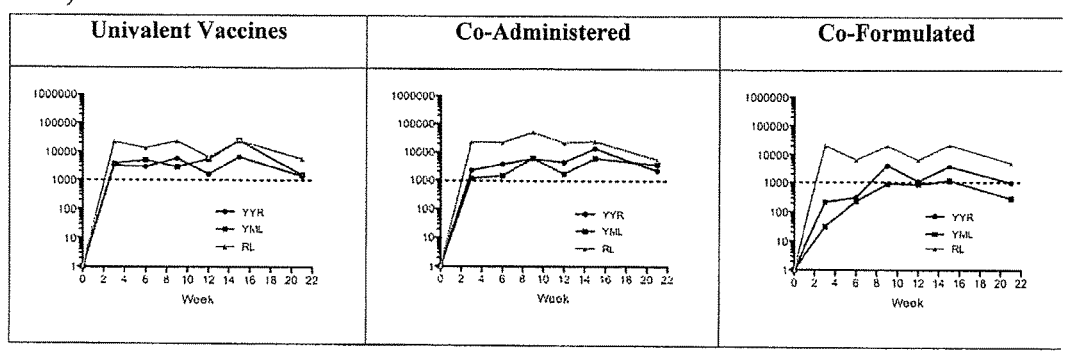
C)
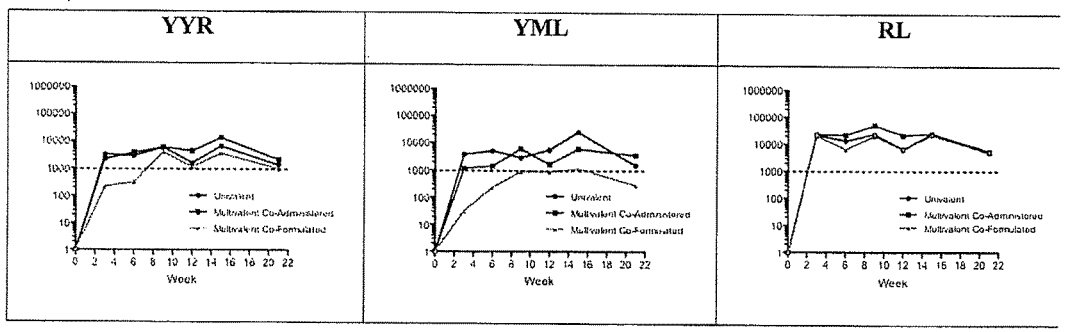
FIGURE 7 CONT'D

```
MVPQALLFVPLLAFPMCFGKFPIYTIPDKLGPWSPIDIHHLSCPNNLVVEDEGCTNLSGF    60
SYMELKVGYISAIKVNGFTCTGVVTEAETYTNFVGYVTTTFKRKHFRPTPDACRAAYNWK   120
MAGDPRYEESLHNPYPDYHWLRTVKTTKESLIIISPSVADLDPYDKSLHSRVFPSGKCLG   180
ITISSTYCSTNHDYTIWMPENVRLGTSCDIFTNSRGKRASKGSKTCGFVDERGLYKSLKG   240
ACKLKLCGVLGLRLMDGTWVAMPTSDETKWCPPDQLVNLHDFRSDEIEHLVVEELVRKRE   300
ECLDALESIMTTKSVSFRRLSHLRKLVPGFGKAYTIFNKTLMEADAHYKSVRTWNEIIPS   360
KGCLRVGGRCHPHVNGVFFNGIILGPDGHVLIPEMQSSLLQQHMELLESSVIPLMHPLAD   420
PSTVFKDGDEAEDFVEVHLPDVHKQISGVDLGLPNWG   457
```

FIGURE 10

SEQUENCE LISTING

<160> NUMBER OF SEQ ID NOS: 49

<210> SEQ ID NO 1
<211> LENGTH: 256
<212> TYPE: PRT

<213> ORGANISM: Sheep

<400> SEQUENCE: 1

Met Val Lys Ser His Ile Gly Ser Trp Ile Leu Val Leu Phe Val Ala
1               5                   10                  15

Met Trp Ser Asp Val Gly Leu Cys Lys Lys Arg Pro Lys Pro Gly Gly
            20                  25                  30

Gly Trp Asn Thr Gly Gly Ser Arg Tyr Pro Gly Gln Gly Ser Pro Gly
        35                  40                  45

Gly Asn Arg Tyr Pro Pro Gln Gly Gly Gly Trp Gly Gln Pro His
    50                  55                  60

Gly Gly Gly Trp Gly Gln Pro His Gly Gly Gly Trp Gly Gln Pro His
65                  70                  75                  80

Gly Gly Gly Trp Gly Gln Pro His Gly Gly Gly Trp Gly Gln Gly
                85                  90                  95

Gly Ser His Ser Gln Trp Asn Lys Pro Ser Lys Pro Lys Thr Asn Met
            100                 105                 110

Lys His Val Ala Gly Ala Ala Ala Ala Gly Ala Val Val Gly Gly Leu
        115                 120                 125

Gly Gly Tyr Met Leu Gly Ser Ala Met Ser Arg Pro Leu Ile His Phe
    130                 135                 140

Gly Asn Asp Tyr Glu Asp Arg Tyr Tyr Arg Glu Asn Met Tyr Arg Tyr
145                 150                 155                 160

Pro Asn Gln Val Tyr Tyr Arg Pro Val Asp Gln Tyr Ser Asn Gln Asn
                165                 170                 175

Asn Phe Val His Asp Cys Val Asn Ile Thr Val Lys Gln His Thr Val
            180                 185                 190

Thr Thr Thr Thr Lys Gly Glu Asn Phe Thr Glu Thr Asp Ile Lys Ile
        195                 200                 205

Met Glu Arg Val Val Glu Gln Met Cys Ile Thr Gln Tyr Gln Arg Glu
    210                 215                 220

Ser Gln Ala Tyr Tyr Gln Arg Gly Ala Ser Val Ile Leu Phe Ser Ser
225                 230                 235                 240

Pro Pro Val Ile Leu Leu Ile Ser Phe Leu Ile Phe Leu Ile Val Gly
                245                 250                 255

<210> SEQ ID NO 2
<211> LENGTH: 264
<212> TYPE: PRT
<213> ORGANISM: Bovine
<220> FEATURE:
<221> NAME/KEY: misc_feature
<222> LOCATION: (154)..(154)
<223> OTHER INFORMATION: Xaa can be any naturally occurring amino acid

<400> SEQUENCE: 2

Met Val Lys Ser His Ile Gly Ser Trp Ile Leu Val Leu Phe Val Ala
1               5                   10                  15

Met Trp Ser Asp Val Gly Leu Cys Lys Lys Arg Pro Lys Pro Gly Gly
            20                  25                  30

Gly Trp Asn Thr Gly Gly Ser Arg Tyr Pro Gly Gln Gly Ser Pro Gly
        35                  40                  45

Gly Asn Arg Tyr Pro Pro Gln Gly Gly Gly Trp Gly Gln Pro His
    50                  55                  60

Gly Gly Gly Trp Gly Gln Pro His Gly Gly Gly Trp Gly Gln Pro His
65                  70                  75                  80

```
Gly Gly Gly Trp Gly Gln Pro His Gly Gly Trp Gly Gln Pro His
            85                  90                  95
Gly Gly Gly Gly Trp Gly Gln Gly Gly Thr His Gly Gln Trp Asn Lys
            100                 105                 110
Pro Ser Lys Pro Lys Thr Asn Met Lys His Val Ala Gly Ala Ala Ala
            115                 120                 125
Ala Gly Ala Val Val Gly Gly Leu Gly Gly Tyr Met Leu Gly Ser Ala
            130                 135                 140
Met Ser Arg Pro Leu Ile His Phe Gly Xaa Asp Tyr Glu Asp Arg Tyr
145                 150                 155                 160
Tyr Arg Glu Asn Met His Arg Tyr Pro Asn Gln Val Tyr Tyr Arg Pro
            165                 170                 175
Val Asp Gln Tyr Ser Asn Gln Asn Asn Phe Val His Asp Cys Val Asn
            180                 185                 190
Ile Thr Val Lys Glu His Thr Val Thr Thr Thr Lys Gly Glu Asn
            195                 200                 205
Phe Thr Glu Thr Asp Ile Lys Met Met Glu Arg Val Val Glu Gln Met
            210                 215                 220
Cys Ile Thr Gln Tyr Gln Arg Glu Ser Gln Ala Tyr Tyr Gln Arg Gly
225                 230                 235                 240
Ala Ser Val Ile Leu Phe Ser Ser Pro Val Ile Leu Leu Ile Ser
            245                 250                 255
Phe Leu Ile Phe Leu Ile Val Gly
            260

<210> SEQ ID NO 3
<211> LENGTH: 253
<212> TYPE: PRT
<213> ORGANISM: Human

<400> SEQUENCE: 3

Met Ala Asn Leu Gly Cys Trp Met Leu Val Leu Phe Val Ala Thr Trp
1               5                   10                  15
Ser Asp Leu Gly Leu Cys Lys Lys Arg Pro Lys Pro Gly Gly Trp Asn
            20                  25                  30
Thr Gly Gly Ser Arg Tyr Pro Gly Gln Gly Ser Pro Gly Gly Asn Arg
            35                  40                  45
Tyr Pro Pro Gln Gly Gly Gly Trp Gly Gln Pro His Gly Gly Gly
50                  55                  60
Trp Gly Gln Pro His Gly Gly Trp Gly Gln Pro His Gly Gly Gly
65                  70                  75                  80
Trp Gly Gln Pro His Gly Gly Trp Gly Gln Gly Gly Gly Thr His
            85                  90                  95
Ser Gln Trp Asn Lys Pro Ser Lys Pro Lys Thr Asn Met Lys His Met
            100                 105                 110
Ala Gly Ala Ala Ala Ala Gly Ala Val Val Gly Gly Leu Gly Gly Tyr
            115                 120                 125
Val Leu Gly Ser Ala Met Ser Arg Pro Ile Ile His Phe Gly Ser Asp
            130                 135                 140
Tyr Glu Asp Arg Tyr Tyr Arg Glu Asn Met His Arg Tyr Pro Asn Gln
145                 150                 155                 160
Val Tyr Tyr Arg Pro Met Asp Glu Tyr Ser Asn Gln Asn Asn Phe Val
            165                 170                 175
His Asp Cys Val Asn Ile Thr Ile Lys Gln His Thr Val Thr Thr Thr
            180                 185                 190
```

Thr Lys Gly Glu Asn Phe Thr Glu Thr Asp Val Lys Met Met Glu Arg
            195                 200                 205

Val Val Glu Gln Met Cys Ile Thr Gln Tyr Glu Arg Glu Ser Gln Ala
210                 215                 220

Tyr Tyr Gln Arg Gly Ser Ser Met Val Leu Phe Ser Ser Pro Pro Val
225                 230                 235                 240

Ile Leu Leu Ile Ser Phe Leu Ile Phe Leu Ile Val Gly
            245                 250

<210> SEQ ID NO 4
<211> LENGTH: 254
<212> TYPE: PRT
<213> ORGANISM: Mouse

<400> SEQUENCE: 4

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro Gly Gly Trp Asn
            20                  25                  30

Thr Gly Gly Ser Arg Tyr Pro Gly Gln Gly Ser Pro Gly Gly Asn Arg
        35                  40                  45

Tyr Pro Pro Gln Gly Gly Thr Trp Gly Gln Pro His Gly Gly Gly Trp
    50                  55                  60

Gly Gln Pro His Gly Gly Ser Trp Gly Gln Pro His Gly Gly Ser Trp
65                  70                  75                  80

Gly Gln Pro His Gly Gly Trp Gly Gln Gly Gly Gly Thr His Asn
            85                  90                  95

Gln Trp Asn Lys Pro Ser Lys Pro Lys Thr Asn Leu Lys His Val Ala
            100                 105                 110

Gly Ala Ala Ala Ala Gly Ala Val Val Gly Gly Leu Gly Gly Tyr Met
        115                 120                 125

Leu Gly Ser Ala Met Ser Arg Pro Met Ile His Phe Gly Asn Asp Trp
    130                 135                 140

Glu Asp Arg Tyr Tyr Arg Glu Asn Met Tyr Arg Tyr Pro Asn Gln Val
145                 150                 155                 160

Tyr Tyr Arg Pro Val Asp Gln Tyr Ser Asn Gln Asn Asn Phe Val His
                165                 170                 175

Asp Cys Val Asn Ile Thr Ile Lys Gln His Thr Val Thr Thr Thr Thr
            180                 185                 190

Lys Gly Glu Asn Phe Thr Glu Thr Asp Val Lys Met Met Glu Arg Val
        195                 200                 205

Val Glu Gln Met Cys Val Thr Gln Tyr Gln Lys Glu Ser Gln Ala Tyr
    210                 215                 220

Tyr Asp Gly Arg Arg Ser Ser Ser Thr Val Leu Phe Ser Ser Pro Pro
225                 230                 235                 240

Val Ile Leu Leu Ile Ser Phe Leu Ile Phe Leu Ile Val Gly
                245                 250

<210> SEQ ID NO 5
<211> LENGTH: 256
<212> TYPE: PRT
<213> ORGANISM: Elk

<400> SEQUENCE: 5

Met Val Lys Ser His Ile Gly Ser Trp Ile Leu Val Leu Phe Val Ala
1               5                   10                  15

```
Met Trp Ser Asp Val Gly Leu Cys Lys Lys Arg Pro Lys Pro Gly Gly
            20                  25                  30

Gly Trp Asn Thr Gly Gly Ser Arg Tyr Pro Gly Gln Gly Ser Pro Gly
        35                  40                  45

Gly Asn Arg Tyr Pro Pro Gln Gly Gly Gly Trp Gly Gln Pro His
50                  55                  60

Gly Gly Gly Trp Gly Gln Pro His Gly Gly Trp Gly Gln Pro His
65                  70                  75                  80

Gly Gly Gly Trp Gly Gln Pro His Gly Gly Gly Trp Gly Gln Gly
                85                  90                  95

Gly Thr His Ser Gln Trp Asn Lys Pro Ser Lys Pro Lys Thr Asn Met
            100                 105                 110

Lys His Val Ala Gly Ala Ala Ala Gly Ala Val Val Gly Gly Leu
            115                 120                 125

Gly Gly Tyr Met Leu Gly Ser Ala Met Ser Arg Pro Leu Ile His Phe
        130                 135                 140

Gly Asn Asp Tyr Glu Asp Arg Tyr Tyr Arg Glu Asn Met Tyr Arg Tyr
145                 150                 155                 160

Pro Asn Gln Val Tyr Tyr Arg Pro Val Asp Gln Tyr Asn Asn Gln Asn
                165                 170                 175

Thr Phe Val His Asp Cys Val Asn Ile Thr Val Lys Gln His Thr Val
            180                 185                 190

Thr Thr Thr Thr Lys Gly Glu Asn Phe Thr Glu Thr Asp Ile Lys Met
        195                 200                 205

Met Glu Arg Val Val Glu Gln Met Cys Ile Thr Gln Tyr Gln Arg Glu
    210                 215                 220

Ser Glu Ala Tyr Tyr Gln Arg Gly Ala Ser Val Ile Leu Phe Ser Ser
225                 230                 235                 240

Pro Pro Val Ile Leu Leu Ile Ser Phe Leu Ile Phe Leu Ile Val Gly
                245                 250                 255

<210> SEQ ID NO 6
<211> LENGTH: 256
<212> TYPE: PRT
<213> ORGANISM: MuleDeer

<400> SEQUENCE: 6

Met Val Lys Ser His Ile Gly Ser Trp Ile Leu Val Leu Phe Val Ala
1               5                   10                  15

Met Trp Ser Asp Val Gly Leu Cys Lys Lys Arg Pro Lys Pro Gly Gly
            20                  25                  30

Gly Trp Asn Thr Gly Gly Ser Arg Tyr Pro Gly Gln Gly Ser Pro Gly
        35                  40                  45

Gly Asn Arg Tyr Pro Pro Gln Gly Gly Gly Trp Gly Gln Pro His
50                  55                  60

Gly Gly Gly Trp Gly Gln Pro His Gly Gly Trp Gly Gln Pro His
65                  70                  75                  80

Gly Gly Gly Trp Gly Gln Pro His Gly Gly Gly Trp Gly Gln Gly
                85                  90                  95

Gly Thr His Ser Gln Trp Asn Lys Pro Ser Lys Pro Lys Thr Asn Met
            100                 105                 110

Lys His Val Ala Gly Ala Ala Ala Gly Ala Val Val Gly Gly Leu
            115                 120                 125

Gly Gly Tyr Met Leu Gly Ser Ala Met Ser Arg Pro Leu Ile His Phe
```

```
              130                 135                 140
Gly Asn Asp Tyr Glu Asp Arg Tyr Tyr Arg Glu Asn Met Tyr Arg Tyr
145                 150                 155                 160

Pro Asn Gln Val Tyr Tyr Arg Pro Val Asp Gln Tyr Asn Asn Gln Asn
                165                 170                 175

Thr Phe Val His Asp Cys Val Asn Ile Thr Val Lys Gln His Thr Val
            180                 185                 190

Thr Thr Thr Thr Lys Gly Glu Asn Phe Thr Glu Thr Asp Ile Lys Met
        195                 200                 205

Met Glu Arg Val Val Glu Gln Met Cys Ile Thr Gln Tyr Gln Arg Glu
    210                 215                 220

Ser Gln Ala Tyr Tyr Gln Arg Gly Ala Ser Val Ile Leu Phe Ser Ser
225                 230                 235                 240

Pro Pro Val Ile Leu Leu Ile Ser Phe Leu Ile Phe Leu Ile Val Gly
                245                 250                 255

<210> SEQ ID NO 7
<211> LENGTH: 256
<212> TYPE: PRT
<213> ORGANISM: Whitetail Deer

<400> SEQUENCE: 7

Met Val Lys Ser His Ile Gly Ser Trp Ile Leu Val Leu Phe Val Ala
1               5                   10                  15

Met Trp Ser Asp Val Gly Leu Cys Lys Lys Arg Pro Lys Pro Gly Gly
            20                  25                  30

Gly Trp Asn Thr Gly Gly Ser Arg Tyr Pro Gly Gln Gly Ser Pro Gly
        35                  40                  45

Gly Asn Arg Tyr Pro Pro Gln Gly Gly Gly Trp Gly Gln Pro His
50                  55                  60

Gly Gly Gly Trp Gly Gln Pro His Gly Gly Gly Trp Gly Gln Pro His
65                  70                  75                  80

Gly Gly Gly Trp Gly Gln Pro His Gly Gly Gly Trp Gly Gln Gly
                85                  90                  95

Gly Thr His Ser Gln Trp Asn Lys Pro Ser Lys Pro Lys Thr Asn Met
            100                 105                 110

Lys His Val Ala Gly Ala Ala Ala Ala Gly Ala Val Val Gly Gly Leu
        115                 120                 125

Gly Gly Tyr Met Leu Gly Ser Ala Met Ser Arg Pro Leu Ile His Phe
    130                 135                 140

Gly Asn Asp Tyr Glu Asp Arg Tyr Tyr Arg Glu Asn Met Tyr Arg Tyr
145                 150                 155                 160

Pro Asn Gln Val Tyr Tyr Arg Pro Val Asp Gln Tyr Asn Asn Gln Asn
                165                 170                 175

Thr Phe Val His Asp Cys Val Asn Ile Thr Val Lys Gln His Thr Val
            180                 185                 190

Thr Thr Thr Thr Lys Gly Glu Asn Phe Thr Glu Thr Asp Ile Lys Met
        195                 200                 205

Met Glu Arg Val Val Glu Gln Met Cys Ile Thr Gln Tyr Gln Arg Glu
    210                 215                 220

Ser Gln Ala Tyr Tyr Gln Arg Gly Ala Ser Val Ile Leu Phe Ser Ser
225                 230                 235                 240

Pro Pro Val Ile Leu Leu Ile Ser Phe Leu Ile Phe Leu Ile Val Gly
                245                 250                 255
```

<210> SEQ ID NO 8
<211> LENGTH: 2794
<212> TYPE: DNA
<213> ORGANISM: Pasteurella haemolytica

<400> SEQUENCE: 8

```
atggctactg ttatagatct aagcttccca aaaactgggg caaaaaaaat tatcctctat      60
attccccaaa attaccaata tgatactgaa caaggtaatg gtttacagga tttagtcaaa     120
gcggccgaag agttggggat tgaggtacaa agagaagaac gcaataatat tgcaacagct     180
caaaccagtt taggcacgat tcaaaccgct attggcttaa ctgagcgtgg cattgtgtta     240
tccgctccac aaattgataa attgctacag aaaactaaag caggccaagc attaggttct     300
gccgaaagca ttgtacaaaa tgcaaataaa gccaaaactg tattatctgg cattcaatct     360
attttaggct cagtattggc tggaatggat ttagatgagg ccttacagaa taacagcaac     420
caacatgctc ttgctaaagc tggcttggag ctaacaaatt cattaattga aaatattgct     480
aattcagtaa aaacacttga cgaatttggt gagcaaatta gtcaatttgg ttcaaaacta     540
caaaatatca aaggcttagg gactttagga gacaaactca aaaatatcgg tggacttgat     600
aaagctggcc ttggtttaga tgttatctca gggctattat cgggcgcaac agctgcactt     660
gtacttgcag ataaaaatgc ttcaacagct aaaaagtgg gtgcgggttt tgaattggca     720
aaccaagttg ttggtaatat taccaaagcc gtttcttctt acattttagc ccaacgtgtt     780
gcagcaggtt tatcttcaac tgggcctgtg gctgctttaa ttgcttctac tgtttctctt     840
gcgattagcc cattagcatt tgccggtatt gccgataaat ttaatcatgc aaaaagttta     900
gagagttatg ccgaacgctt taaaaaatta ggctatgacg agataatttt attagcagaa     960
tatcagcggg gaacagggac tattgatgca tcggttactg caattaatac cgcattggcc    1020
gctattgctg tggtgtgtc tgctgctgca gccggctcgg ttattgcttc accgattgcc    1080
ttattagtat ctgggattac cggtgtaatt tctacgattc tgcaatattc taaacaagca    1140
atgtttgagc acgttgcaaa taaaattcat aacaaaattg tagaatggga aaaaaataat    1200
cacggtaaga actactttga aaatggttac gatgcccgtt atcttgcgaa tttcaagat    1260 aatatgaaat tcttactgaa cttaaacaaa gagttacagg cagaacgtgt catcgctatt    1320
actcagcagc aatgggataa caacattggt gatttagctg gtattagccg tttaggtgaa    1380
aaagtcctta gtggtaaagc ctatgtggat gcgtttgaag aaggcaaaca cattaaagcc    1440 gataaaattag tacagttgga ttcggcaaac ggtattattg atgtgagtaa ttcgggtaaa    1500
gcgaaaactc agcatatctt attcagaacg ccattattga cgccgggaac agagcatcgt    1560
gaacgcgtac aaacaggtaa atatgaatat attaccaagc tcaatattaa ccgtgtagat    1620
agctggaaaa ttacagatgg tgcagcaagt tctacctttg atttaactaa cgttgttcag    1680
cgtattggta ttgaattaga caatgctgga aatgtaacta aaccaaaga aacaaaaatt    1740 attgccaaac ttggtgaagg tgatgacaac gtatttgttg gttctggtac gacgaaaatt    1800
gatggcggtg aaggttacga ccgagttcac tatagccgtg gaaactatgg tgctttaact    1860
attgatgcaa ccaaagagac cgagcaaggt agttataccg taaatcgttt cgtagaaacc    1920
ggtaaagcac tacacgaagt gacttcaacc cataccgcat tagtgggcaa ccgtgaagaa    1980
aaaatagaat atcgtcatag caataaccag caccatgccg ttattacac caaagatacc    2040 ttgaaagctg ttgaagaaat tatccggtaca tcacataacg atatctttaa aggtagtaag    2100
ttcaatgatg cctttaacgg tggtgatggt gtcgatacta ttgacggtaa cgacggcaat    2160
```

```
gaccgcttat ttggtggtaa aggcgatgat attctcgatg gtggaaatgg tgatgatttt    2220
atcgatggcg gtaaaggcaa cgacctatta cacggtggca agggcgatga tattttcgtt    2280
caccgtaaag gcgatggtaa tgatattatt accgattctg acggcaatga taaattatca    2340
ttctctgatt cgaacttaaa agatttaaca tttgaaaaag ttaaacataa tcttgtcatc    2400
acgaatagca aaaagagaa agtgaccatt caaaactggt tccgagaggc tgattttgct    2460
aaagaagtgc ctaattataa agcaactaaa gatgagaaaa tcgaagaaat catcggtcaa    2520
aatggcgagc ggatcacctc aaagcaagtt gatgatctta tcgcaaaagg taacggcaaa    2580
attacccaag atgagctatc aaaagttgtt gataactatg aattgctcaa acatagcaaa    2640
aatgtgacaa acagcttaga taagttaatc tcatctgtaa gtgcatttac ctcgtctaat    2700
gattcgagaa atgtattagt ggctccaact tcaatgttgg atcaaagttt atcttctctt    2760
caatttgcta ggggatccta gctagctagc catg                                2794
```

`<210>` SEQ ID NO 9
`<211>` LENGTH: 2794
`<212>` TYPE: DNA
`<213>` ORGANISM: Pasteurella haemolytica

`<400>` SEQUENCE: 9

```
catggctagc tagctaggat cccctagcaa attgaagaga agataaactt tgatccaaca      60
ttgaagttgg agccactaat acatttctcg aatcattaga cgaggtaaat gcacttacag     120
atgagattaa cttatctaag ctgttttgtca cattttttgct atgttgagc aattcatagt    180 tatcaacaac ttttgatagc tcatcttggg taattttgcc gttaccttt gcgataagat     240 catcaacttg ctttgaggtg atccgctcgc cattttgacc gatgatttct tcgatttttct    300 catctttagt tgcttttataa ttaggcactt ctttagcaaa atcagcctct cggaaccagt    360
tttgaatggt cactttctct ttttttgctat tcgtgatgac aagattatgt ttaacttttt    420
caaatgttaa atcttttaag ttcgaatcag agaatgataa tttatcattg ccgtcagaat    480
cggtaataat atcattacca tcgcctttac ggtgaacgaa aatatcatcg cccttgccac    540
cgtgtaatag gtcgttgcct ttaccgccat cgataaaatc atcaccattt ccaccatcga    600
gaatatcatc gccttaccca ccaaataagc ggtcattgcc gtcgttaccg tcaatagtat    660
cgacaccatc accaccgtta aaggcatcat tgaacttact acctttaaag atatcgttat    720
gtgatgtacc gataatttct tcaacagctt tcaaggtatc tttggtgtaa taaccggcat    780
ggtgctggtt attgctatga cgatattcta tttttcttc acggttgccc actaatgcgg    840
tatgggttga agtcacttcg tgtagtgctt taccggtttc tacgaaacga tttacggtat    900
aactaccttg ctcggtctct ttggttgcat caatagttaa agcaccatag tttccacggc    960
tatagtgaac tcggtcgtaa ccttcaccgc catcaatttc cgtcgtacca gaaccaacaa   1020
atacgttgtc atcaccttca ccaagtttgg caataatttt tgtttctttg gttttagtta   1080
catttccagc attgtctaat tcaataccaa tacgctgaac aacgttagtt aaatcaaagg   1140
tagaacttgc tgcaccatct gtaattttcc agctatctac acggttaata ttgagcttgg   1200
taatatattc atatttacct gtttgtacgc gttcacgatg ctctgttccc ggcgtcaata   1260
atggcgttct gaataagata tgctgagttt tcgctttacc cgaattactc acatcaataa   1320
taccgtttgc cgaatccaac tgtactaatt tatcggcttt aatgtgtttg ccttcttcaa   1380
acgcatccac ataggcttta ccactaagga cttttttcacc taaacggcta ataccagcta   1440
```

```
aatcaccaat gttgttatcc cattgctgct gagtaatagc gatgacacgt tctgcctgta     1500
actctttgtt taagttcagt aagaatttca tattatcttg taaattcgca agataacggg     1560
catcgtaacc attttcaaag tagttcttac cgtgattatt tttttcccat tctacaattt     1620
tgttatgaat tttatttgca acgtgctcaa acattgcttg tttagaatat tgcagaatcg     1680
tagaaattac accggtaatc ccagatacta ataaggcaat cggtgaagca ataaccgagc     1740
cggctgcagc agcagacaca ccaccagcaa tagcggccaa tgcggtatta attgcagtaa     1800
ccgatgcatc aatagtccct gttccccgct gatattctgc taataaatta tctccgtcat     1860
agcctaattt tttaaagcgt tcggcataac tctctaaact ttttgcatga ttaaatttat     1920
cggcaatacc ggcaaatgct aatgggctaa tcgcaagaga aacagtagaa gcaattaaag     1980
cagccacagg cccagttgaa gataaacctg ctgcaacacg ttgggctaaa atgtaagaag     2040
aaacggcttt ggtaatatta ccaacaactt ggtttgccaa ttcaaaaccc gcacccactt     2100
ttttagctgt tgaagcattt ttatctgcaa gtacaagtgc agctgttgcg cccgataata     2160
gccctgagat aacatctaaa ccaaggccag ctttatcaag tccaccgata ttttttgagtt    2220 tgtctcctaa agtccctaag cctttgatat tttgtagttt tgaaccaaat tgactaattt     2280
gctcaccaaa ttcgtcaagt gttttactg  aattagcaat attttcaatt aatgaatttg     2340
ttagctccaa gccagcttta gcaagagcat gttggttgct gttattctgt aaggcctcat     2400
ctaaatccat tccagccaat actgagccta aaatagattg aatgccagat aatacagttt     2460
tggctttatt tgcattttgt acaatgcttt cggcagaacc taatgcttgg cctgctttag     2520
ttttctgtag caattatca  atttgtggag cggataacac aatgccacgc tcagttaagc     2580
caatagcggt ttgaatcgtg cctaaactgg tttgagctgt tgcaatatta ttgcgttctt     2640
ctctttgtac ctcaatcccc aactcttcgg ccgctttgac taaatcctgt aaaccattac     2700
cttgttcagt atcatattgg taattttggg gaatatagag gataattttt tttgccccag     2760
tttttgggaa gcttagatct ataacagtag ccat                                 2794
```

<210> SEQ ID NO 10
<211> LENGTH: 926
<212> TYPE: PRT
<213> ORGANISM: Pasteurella haemolytica

<400> SEQUENCE: 10

```
Met Ala Thr Val Ile Asp Leu Ser Phe Pro Lys Thr Gly Ala Lys Lys
1               5                   10                  15

Ile Ile Leu Tyr Ile Pro Gln Asn Tyr Gln Tyr Asp Thr Glu Gln Gly
            20                  25                  30

Asn Gly Leu Gln Asp Leu Val Lys Ala Ala Glu Glu Leu Gly Ile Glu
        35                  40                  45

Val Gln Arg Glu Glu Arg Asn Asn Ile Ala Thr Ala Gln Thr Ser Leu
    50                  55                  60

Gly Thr Ile Gln Thr Ala Ile Gly Leu Thr Arg Gly Ile Val Leu
65                  70                  75                  80

Ser Ala Pro Gln Ile Asp Lys Leu Leu Gln Lys Thr Lys Ala Gly Gln
                85                  90                  95

Ala Leu Gly Ser Ala Glu Ser Ile Val Gln Asn Ala Asn Lys Ala Lys
            100                 105                 110

Thr Val Leu Ser Gly Ile Gln Ser Ile Leu Gly Ser Val Leu Ala Gly
        115                 120                 125

Met Asp Leu Asp Glu Ala Leu Gln Asn Asn Ser Asn Gln His Ala Leu
```

```
            130                 135                 140
Ala Lys Ala Gly Leu Glu Leu Thr Asn Ser Leu Ile Glu Asn Ile Ala
145                 150                 155                 160

Asn Ser Val Lys Thr Leu Asp Glu Phe Gly Glu Gln Ile Ser Gln Phe
                165                 170                 175

Gly Ser Lys Leu Gln Asn Ile Lys Gly Leu Gly Thr Leu Gly Asp Lys
            180                 185                 190

Leu Lys Asn Ile Gly Gly Leu Asp Lys Ala Gly Leu Gly Leu Asp Val
        195                 200                 205

Ile Ser Gly Leu Leu Ser Gly Ala Thr Ala Ala Leu Val Leu Ala Asp
    210                 215                 220

Lys Asn Ala Ser Thr Ala Lys Lys Val Gly Ala Gly Phe Glu Leu Ala
225                 230                 235                 240

Asn Gln Val Val Gly Asn Ile Thr Lys Ala Val Ser Ser Tyr Ile Leu
                245                 250                 255

Ala Gln Arg Val Ala Ala Gly Leu Ser Ser Thr Gly Pro Val Ala Ala
            260                 265                 270

Leu Ile Ala Ser Thr Val Ser Leu Ala Ile Ser Pro Leu Ala Phe Ala
        275                 280                 285

Gly Ile Ala Asp Lys Phe Asn His Ala Lys Ser Leu Glu Ser Tyr Ala
    290                 295                 300

Glu Arg Phe Lys Lys Leu Gly Tyr Asp Gly Asp Asn Leu Leu Ala Glu
305                 310                 315                 320

Tyr Gln Arg Gly Thr Gly Thr Ile Asp Ala Ser Val Thr Ala Ile Asn
                325                 330                 335

Thr Ala Leu Ala Ala Ile Ala Gly Gly Val Ser Ala Ala Ala Ala Gly
            340                 345                 350

Ser Val Ile Ala Ser Pro Ile Ala Leu Leu Val Ser Gly Ile Thr Gly
        355                 360                 365

Val Ile Ser Thr Ile Leu Gln Tyr Ser Lys Gln Ala Met Phe Glu His
    370                 375                 380

Val Ala Asn Lys Ile His Asn Lys Ile Val Glu Trp Glu Lys Asn Asn
385                 390                 395                 400

His Gly Lys Asn Tyr Phe Glu Asn Gly Tyr Asp Ala Arg Tyr Leu Ala
                405                 410                 415

Asn Leu Gln Asp Asn Met Lys Phe Leu Leu Asn Leu Asn Lys Glu Leu
            420                 425                 430

Gln Ala Glu Arg Val Ile Ala Ile Thr Gln Gln Trp Asp Asn Asn
        435                 440                 445

Ile Gly Asp Leu Ala Gly Ile Ser Arg Leu Gly Glu Lys Val Leu Ser
    450                 455                 460

Gly Lys Ala Tyr Val Asp Ala Phe Glu Glu Gly Lys His Ile Lys Ala
465                 470                 475                 480

Asp Lys Leu Val Gln Leu Asp Ser Ala Asn Gly Ile Ile Asp Val Ser
                485                 490                 495

Asn Ser Gly Lys Ala Lys Thr Gln His Ile Leu Phe Arg Thr Pro Leu
            500                 505                 510

Leu Thr Pro Gly Thr Glu His Arg Glu Arg Val Gln Thr Gly Lys Tyr
        515                 520                 525

Glu Tyr Ile Thr Lys Leu Asn Ile Asn Arg Val Asp Ser Trp Lys Ile
    530                 535                 540

Thr Asp Gly Ala Ala Ser Ser Thr Phe Asp Leu Thr Asn Val Val Gln
545                 550                 555                 560
```

-continued

```
Arg Ile Gly Ile Glu Leu Asp Asn Ala Gly Asn Val Thr Lys Thr Lys
                565                 570                 575
Glu Thr Lys Ile Ile Ala Lys Leu Gly Gly Asp Asp Asn Val Phe
            580                 585                 590
Val Gly Ser Gly Thr Thr Glu Ile Asp Gly Gly Glu Gly Tyr Asp Arg
        595                 600                 605
Val His Tyr Ser Arg Gly Asn Tyr Gly Ala Leu Thr Ile Asp Ala Thr
    610                 615                 620
Lys Glu Thr Glu Gln Gly Ser Tyr Thr Val Asn Arg Phe Val Glu Thr
625                 630                 635                 640
Gly Lys Ala Leu His Glu Val Thr Ser Thr His Thr Ala Leu Val Gly
                645                 650                 655
Asn Arg Glu Glu Lys Ile Glu Tyr Arg His Ser Asn Asn Gln His His
            660                 665                 670
Ala Gly Tyr Tyr Thr Lys Asp Thr Leu Lys Ala Val Glu Glu Ile Ile
        675                 680                 685
Gly Thr Ser His Asn Asp Ile Phe Lys Gly Ser Lys Phe Asn Asp Ala
    690                 695                 700
Phe Asn Gly Gly Asp Gly Val Asp Thr Ile Asp Gly Asn Asp Gly Asn
705                 710                 715                 720
Asp Arg Leu Phe Gly Gly Lys Gly Asp Ile Leu Asp Gly Gly Asn
                725                 730                 735
Gly Asp Asp Phe Ile Asp Gly Gly Lys Gly Asn Asp Leu Leu His Gly
            740                 745                 750
Gly Lys Gly Asp Asp Ile Phe Val His Arg Lys Gly Asp Gly Asn Asp
        755                 760                 765
Ile Ile Thr Asp Ser Asp Gly Asn Asp Lys Leu Ser Phe Ser Asp Ser
    770                 775                 780
Asn Leu Lys Asp Leu Thr Phe Glu Lys Val Lys His Asn Leu Val Ile
785                 790                 795                 800
Thr Asn Ser Lys Lys Glu Lys Val Thr Ile Gln Asn Trp Phe Arg Glu
                805                 810                 815
Ala Asp Phe Ala Lys Glu Val Pro Asn Tyr Lys Ala Thr Lys Asp Glu
            820                 825                 830
Lys Ile Glu Glu Ile Ile Gly Gln Asn Gly Glu Arg Ile Thr Ser Lys
        835                 840                 845
Gln Val Asp Asp Leu Ile Ala Lys Gly Asn Gly Lys Ile Thr Gln Asp
    850                 855                 860
Glu Leu Ser Lys Val Val Asp Asn Tyr Glu Leu Leu Lys His Ser Lys
865                 870                 875                 880
Asn Val Thr Asn Ser Leu Asp Lys Leu Ile Ser Ser Val Ser Ala Phe
                885                 890                 895
Thr Ser Ser Asn Asp Ser Arg Asn Val Leu Val Ala Pro Thr Ser Met
            900                 905                 910
Leu Asp Gln Ser Leu Ser Ser Leu Gln Phe Ala Arg Gly Ser
        915                 920                 925
```

<210> SEQ ID NO 11
<211> LENGTH: 6
<212> TYPE: PRT
<213> ORGANISM: Artificial Sequence
<220> FEATURE:
<223> OTHER INFORMATION: Sythetic peptide
<220> FEATURE:
<221> NAME/KEY: misc_feature

```
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 11

Gly Gly Xaa Gly Xaa Asp
1               5

<210> SEQ ID NO 12
<211> LENGTH: 4
<212> TYPE: PRT
<213> ORGANISM: Artificial Sequence
<220> FEATURE:
<223> OTHER INFORMATION: Sythetic peptide

<400> SEQUENCE: 12

Gln Tyr Ser Asn
1

<210> SEQ ID NO 13
<211> LENGTH: 7
<212> TYPE: PRT
<213> ORGANISM: Artificial Sequence
<220> FEATURE:
<223> OTHER INFORMATION: Sythetic peptide

<400> SEQUENCE: 13

Gly Tyr Met Leu Gly Ser Ala
1               5

<210> SEQ ID NO 14
<211> LENGTH: 8
<212> TYPE: PRT
<213> ORGANISM: Artificial Sequence
<220> FEATURE:
<223> OTHER INFORMATION: Sythetic peptide

<400> SEQUENCE: 14

Gly Tyr Met Leu Gly Ser Ala Met
1               5

<210> SEQ ID NO 15
<211> LENGTH: 9
<212> TYPE: PRT
<213> ORGANISM: Artificial Sequence
<220> FEATURE:
<223> OTHER INFORMATION: Sythetic peptide

<400> SEQUENCE: 15

Gly Tyr Met Leu Gly Ser Ala Met Ser
1               5

<210> SEQ ID NO 16
<211> LENGTH: 10
<212> TYPE: PRT
<213> ORGANISM: Artificial Sequence
<220> FEATURE:
<223> OTHER INFORMATION: Sythetic peptide

<400> SEQUENCE: 16

Gly Tyr Met Leu Gly Ser Ala Met Ser Arg
1               5                   10

<210> SEQ ID NO 17
```

```
<211> LENGTH: 11
<212> TYPE: PRT
<213> ORGANISM: Artificial Sequence
<220> FEATURE:
<223> OTHER INFORMATION: Sythetic peptide

<400> SEQUENCE: 17

Gly Tyr Met Leu Gly Ser Ala Met Ser Arg Pro
1               5                   10

<210> SEQ ID NO 18
<211> LENGTH: 9
<212> TYPE: PRT
<213> ORGANISM: Artificial Sequence
<220> FEATURE:
<223> OTHER INFORMATION: Sythetic peptide

<400> SEQUENCE: 18

Asp Gln Tyr Ser Asn Gln Asn Asn Phe
1               5

<210> SEQ ID NO 19
<211> LENGTH: 10
<212> TYPE: PRT
<213> ORGANISM: Artificial Sequence
<220> FEATURE:
<223> OTHER INFORMATION: Sythetic peptide

<400> SEQUENCE: 19

Val Asp Gln Tyr Ser Asn Gln Asn Asn Phe
1               5                   10

<210> SEQ ID NO 20
<211> LENGTH: 9
<212> TYPE: PRT
<213> ORGANISM: Artificial Sequence
<220> FEATURE:
<223> OTHER INFORMATION: Sythetic peptide

<400> SEQUENCE: 20

Asp Glu Tyr Ser Asn Gln Asn Asn Phe
1               5

<210> SEQ ID NO 21
<211> LENGTH: 10
<212> TYPE: PRT
<213> ORGANISM: Artificial Sequence
<220> FEATURE:
<223> OTHER INFORMATION: Sythetic peptide

<400> SEQUENCE: 21

Met Asp Glu Tyr Ser Asn Gln Asn Asn Phe
1               5                   10

<210> SEQ ID NO 22
<211> LENGTH: 9
<212> TYPE: PRT
<213> ORGANISM: Artificial Sequence
<220> FEATURE:
<223> OTHER INFORMATION: Sythetic peptide

<400> SEQUENCE: 22

Asp Gln Tyr Asn Asn Gln Asn Thr Phe
1               5

<210> SEQ ID NO 23
<211> LENGTH: 10
```

<212> TYPE: PRT
<213> ORGANISM: Artificial Sequence
<220> FEATURE:
<223> OTHER INFORMATION: Sythetic peptide

<400> SEQUENCE: 23

Val Asp Gln Tyr Asn Asn Gln Asn Thr Phe
1               5                   10

<210> SEQ ID NO 24
<211> LENGTH: 14
<212> TYPE: PRT
<213> ORGANISM: Artificial Sequence
<220> FEATURE:
<223> OTHER INFORMATION: Sythetic peptide

<400> SEQUENCE: 24

Gln Val Tyr Tyr Arg Pro Val Asp Gln Tyr Ser Asn Gln Asn
1               5                   10

<210> SEQ ID NO 25
<211> LENGTH: 168
<212> TYPE: PRT
<213> ORGANISM: Artificial Sequence
<220> FEATURE:
<223> OTHER INFORMATION: Sythetic peptide

<400> SEQUENCE: 25

Gln Val Tyr Tyr Arg Pro Val Asp Gln Tyr Ser Asn Gln Asn Asn Gln
1               5                   10                  15

Asn Ser Tyr Gln Asp Val Pro Arg Tyr Tyr Val Gln Asn Gln Asn Ser
            20                  25                  30

Tyr Gln Asp Val Pro Arg Tyr Tyr Val Gln Gln Val Tyr Tyr Arg Pro
        35                  40                  45

Val Asp Gln Tyr Ser Asn Gln Asn Gln Asn Ser Tyr Gln Asp Val
    50                  55                  60

Pro Arg Tyr Tyr Val Gln Asn Gln Asn Ser Tyr Gln Asp Val Pro Arg
65                  70                  75                  80

Tyr Tyr Val Gln Gln Val Tyr Tyr Arg Pro Val Asp Gln Tyr Ser Asn
                85                  90                  95

Gln Asn Asn Gln Asn Ser Tyr Gln Asp Val Pro Arg Tyr Tyr Val Gln
            100                 105                 110

Asn Gln Asn Ser Tyr Gln Asp Val Pro Arg Tyr Tyr Val Gln Gln Val
        115                 120                 125

Tyr Tyr Arg Pro Val Asp Gln Tyr Ser Asn Gln Asn Asn Gln Asn Ser
    130                 135                 140

Tyr Gln Asp Val Pro Arg Tyr Tyr Val Gln Asn Gln Asn Ser Tyr Gln
145                 150                 155                 160

Asp Val Pro Arg Tyr Tyr Val Gln
                165

<210> SEQ ID NO 26
<211> LENGTH: 13
<212> TYPE: PRT
<213> ORGANISM: Artificial Sequence
<220> FEATURE:
<223> OTHER INFORMATION: Sythetic peptide

<400> SEQUENCE: 26

Gln Val Tyr Tyr Arg Pro Val Asp Gln Tyr Ser Asn Gln
1               5                   10

<210> SEQ ID NO 27
<211> LENGTH: 156
<212> TYPE: PRT
<213> ORGANISM: Artificial Sequence
<220> FEATURE:
<223> OTHER INFORMATION: Sythetic peptide

<400> SEQUENCE: 27

```
Gln Val Tyr Tyr Arg Pro Val Asp Gln Tyr Ser Asn Gln Gln Asn Ser
1               5                   10                  15

Tyr Gln Asp Val Pro Arg Tyr Val Gln Gln Asn Ser Tyr Gln Asp
            20                  25                  30

Val Pro Arg Tyr Val Gln Val Tyr Tyr Arg Pro Val Asp Gln
            35                  40                  45

Tyr Ser Asn Gln Gln Asn Ser Tyr Gln Asp Val Pro Arg Tyr Val
    50                  55                  60

Gln Gln Asn Ser Tyr Gln Asp Val Pro Arg Tyr Tyr Val Gln Val
65                  70                  75                  80

Tyr Tyr Arg Pro Val Asp Gln Tyr Ser Asn Gln Gln Asn Ser Tyr Gln
                85                  90                  95

Asp Val Pro Arg Tyr Tyr Val Gln Asn Ser Tyr Gln Asp Val Pro
                100                 105                 110

Arg Tyr Tyr Val Gln Val Tyr Tyr Arg Pro Val Asp Gln Tyr Ser
            115                 120                 125

Asn Gln Gln Asn Ser Tyr Gln Asp Val Pro Arg Tyr Tyr Val Gln Gln
    130                 135                 140

Asn Ser Tyr Gln Asp Val Pro Arg Tyr Tyr Val Gln
145                 150                 155
```

<210> SEQ ID NO 28
<211> LENGTH: 12
<212> TYPE: PRT
<213> ORGANISM: Artificial Sequence
<220> FEATURE:
<223> OTHER INFORMATION: Sythetic peptide

<400> SEQUENCE: 28

```
Gln Val Tyr Tyr Arg Pro Val Asp Gln Tyr Ser Asn
1               5                   10
```

<210> SEQ ID NO 29
<211> LENGTH: 144
<212> TYPE: PRT
<213> ORGANISM: Artificial Sequence
<220> FEATURE:
<223> OTHER INFORMATION: Sythetic peptide

<400> SEQUENCE: 29

```
Gln Val Tyr Tyr Arg Pro Val Asp Gln Tyr Ser Asn Asn Ser Tyr Gln
1               5                   10                  15

Asp Val Pro Arg Tyr Tyr Val Gln Asn Ser Tyr Gln Asp Val Pro Arg
            20                  25                  30

Tyr Tyr Val Gln Gln Val Tyr Tyr Arg Pro Val Asp Gln Tyr Ser Asn
        35                  40                  45

Asn Ser Tyr Gln Asp Val Pro Arg Tyr Tyr Val Gln Asn Ser Tyr Gln
    50                  55                  60

Asp Val Pro Arg Tyr Tyr Val Gln Gln Val Tyr Tyr Arg Pro Val Asp
65                  70                  75                  80

Gln Tyr Ser Asn Asn Ser Tyr Gln Asp Val Pro Arg Tyr Tyr Val Gln
```

```
                 85                  90                  95
Asn Ser Tyr Gln Asp Val Pro Arg Tyr Tyr Val Gln Val Tyr Tyr
                100                 105                 110
Arg Pro Val Asp Gln Tyr Ser Asn Asn Ser Tyr Gln Asp Val Pro Arg
        115                 120                 125
Tyr Tyr Val Gln Asn Ser Tyr Gln Asp Val Pro Arg Tyr Tyr Val Gln
    130                 135                 140

<210> SEQ ID NO 30
<211> LENGTH: 11
<212> TYPE: PRT
<213> ORGANISM: Artificial Sequence
<220> FEATURE:
<223> OTHER INFORMATION: Sythetic peptide

<400> SEQUENCE: 30

Gln Val Tyr Tyr Arg Pro Val Asp Gln Tyr Ser
1               5                   10

<210> SEQ ID NO 31
<211> LENGTH: 132
<212> TYPE: PRT
<213> ORGANISM: Artificial Sequence
<220> FEATURE:
<223> OTHER INFORMATION: Sythetic peptide

<400> SEQUENCE: 31

Gln Val Tyr Tyr Arg Pro Val Asp Gln Tyr Ser Ser Tyr Gln Asp Val
1               5                   10                  15
Pro Arg Tyr Tyr Val Gln Ser Tyr Gln Asp Val Pro Arg Tyr Tyr Val
            20                  25                  30
Gln Gln Val Tyr Tyr Arg Pro Val Asp Gln Tyr Ser Ser Tyr Gln Asp
        35                  40                  45
Val Pro Arg Tyr Tyr Val Gln Ser Tyr Gln Asp Val Pro Arg Tyr Tyr
    50                  55                  60
Val Gln Gln Val Tyr Tyr Arg Pro Val Asp Gln Tyr Ser Ser Tyr Gln
65                  70                  75                  80
Asp Val Pro Arg Tyr Tyr Val Gln Ser Tyr Gln Asp Val Pro Arg Tyr
                85                  90                  95
Tyr Val Gln Gln Val Tyr Tyr Arg Pro Val Asp Gln Tyr Ser Ser Tyr
                100                 105                 110
Gln Asp Val Pro Arg Tyr Tyr Val Gln Ser Tyr Gln Asp Val Pro Arg
            115                 120                 125
Tyr Tyr Val Gln
    130

<210> SEQ ID NO 32
<211> LENGTH: 10
<212> TYPE: PRT
<213> ORGANISM: Artificial Sequence
<220> FEATURE:
<223> OTHER INFORMATION: Sythetic peptide

<400> SEQUENCE: 32

Gln Val Tyr Tyr Arg Pro Val Asp Gln Tyr
1               5                   10

<210> SEQ ID NO 33
<211> LENGTH: 120
<212> TYPE: PRT
<213> ORGANISM: Artificial Sequence
```

-continued

```
<220> FEATURE:
<223> OTHER INFORMATION: Sythetic peptide

<400> SEQUENCE: 33

Gln Val Tyr Tyr Arg Pro Val Asp Gln Tyr Tyr Gln Asp Val Pro Arg
1               5                   10                  15

Tyr Tyr Val Gln Tyr Gln Asp Val Pro Arg Tyr Tyr Val Gln Gln Val
            20                  25                  30

Tyr Tyr Arg Pro Val Asp Gln Tyr Tyr Gln Asp Val Pro Arg Tyr Tyr
        35                  40                  45

Val Gln Tyr Gln Asp Val Pro Arg Tyr Tyr Val Gln Gln Val Tyr Tyr
    50                  55                  60

Arg Pro Val Asp Gln Tyr Tyr Gln Asp Val Pro Arg Tyr Tyr Val Gln
65                  70                  75                  80

Tyr Gln Asp Val Pro Arg Tyr Tyr Val Gln Gln Val Tyr Tyr Arg Pro
                85                  90                  95

Val Asp Gln Tyr Tyr Gln Asp Val Pro Arg Tyr Tyr Val Gln Tyr Gln
            100                 105                 110

Asp Val Pro Arg Tyr Tyr Val Gln
        115                 120

<210> SEQ ID NO 34
<211> LENGTH: 9
<212> TYPE: PRT
<213> ORGANISM: Artificial Sequence
<220> FEATURE:
<223> OTHER INFORMATION: Sythetic peptide

<400> SEQUENCE: 34

Gln Val Tyr Tyr Arg Pro Val Asp Gln
1               5

<210> SEQ ID NO 35
<211> LENGTH: 108
<212> TYPE: PRT
<213> ORGANISM: Artificial Sequence
<220> FEATURE:
<223> OTHER INFORMATION: Sythetic peptide

<400> SEQUENCE: 35

Gln Val Tyr Tyr Arg Pro Val Asp Gln Asp Val Pro Arg Tyr Tyr
1               5                   10                  15

Val Gln Gln Asp Val Pro Arg Tyr Tyr Val Gln Gln Val Tyr Tyr Arg
            20                  25                  30

Pro Val Asp Gln Gln Asp Val Pro Arg Tyr Tyr Val Gln Gln Asp Val
        35                  40                  45

Pro Arg Tyr Tyr Val Gln Gln Val Tyr Tyr Arg Pro Val Asp Gln Gln
    50                  55                  60

Asp Val Pro Arg Tyr Tyr Val Gln Gln Asp Val Pro Arg Tyr Tyr Val
65                  70                  75                  80

Gln Gln Val Tyr Tyr Arg Pro Val Asp Gln Gln Asp Val Pro Arg Tyr
                85                  90                  95

Tyr Val Gln Gln Asp Val Pro Arg Tyr Tyr Val Gln
            100                 105

<210> SEQ ID NO 36
<211> LENGTH: 8
<212> TYPE: PRT
<213> ORGANISM: Artificial Sequence
<220> FEATURE:
```

<223> OTHER INFORMATION: Sythetic peptide

<400> SEQUENCE: 36

Gln Val Tyr Tyr Arg Pro Val Asp
1               5

<210> SEQ ID NO 37
<211> LENGTH: 96
<212> TYPE: PRT
<213> ORGANISM: Artificial Sequence
<220> FEATURE:
<223> OTHER INFORMATION: Sythetic peptide

<400> SEQUENCE: 37

Gln Val Tyr Tyr Arg Pro Val Asp Asp Val Pro Arg Tyr Tyr Val Gln
1               5                   10                  15

Asp Val Pro Arg Tyr Tyr Val Gln Gln Val Tyr Tyr Arg Pro Val Asp
            20                  25                  30

Asp Val Pro Arg Tyr Tyr Val Gln Asp Val Pro Arg Tyr Tyr Val Gln
        35                  40                  45

Gln Val Tyr Tyr Arg Pro Val Asp Asp Val Pro Arg Tyr Tyr Val Gln
    50                  55                  60

Asp Val Pro Arg Tyr Tyr Val Gln Gln Val Tyr Tyr Arg Pro Val Asp
65                  70                  75                  80

Asp Val Pro Arg Tyr Tyr Val Gln Asp Val Pro Arg Tyr Tyr Val Gln
                85                  90                  95

<210> SEQ ID NO 38
<211> LENGTH: 132
<212> TYPE: PRT
<213> ORGANISM: Artificial Sequence
<220> FEATURE:
<223> OTHER INFORMATION: Sythetic peptide

<400> SEQUENCE: 38

Gly Tyr Met Leu Gly Ser Ala Met Ser Arg Pro Pro Arg Ser Met Ala
1               5                   10                  15

Ser Gly Leu Met Tyr Gly Pro Arg Ser Met Ala Ser Gly Leu Met Tyr
            20                  25                  30

Gly Gly Tyr Met Leu Gly Ser Ala Met Ser Arg Pro Pro Arg Ser Met
        35                  40                  45

Ala Ser Gly Leu Met Tyr Gly Pro Arg Ser Met Ala Ser Gly Leu Met
    50                  55                  60

Tyr Gly Gly Tyr Met Leu Gly Ser Ala Met Ser Arg Pro Pro Arg Ser
65                  70                  75                  80

Met Ala Ser Gly Leu Met Tyr Gly Pro Arg Ser Met Ala Ser Gly Leu
                85                  90                  95

Met Tyr Gly Gly Tyr Met Leu Gly Ser Ala Met Ser Arg Pro Pro Arg
                100                 105                 110

Ser Met Ala Ser Gly Leu Met Tyr Gly Pro Arg Ser Met Ala Ser Gly
            115                 120                 125

Leu Met Tyr Gly
    130

<210> SEQ ID NO 39
<211> LENGTH: 14
<212> TYPE: PRT
<213> ORGANISM: Artificial Sequence
<220> FEATURE:
<223> OTHER INFORMATION: Sythetic peptide

<400> SEQUENCE: 39

Gly Gly Tyr Met Leu Gly Ser Ala Met Ser Arg Pro Leu Ile
1               5                   10

<210> SEQ ID NO 40
<211> LENGTH: 14
<212> TYPE: PRT
<213> ORGANISM: Artificial Sequence
<220> FEATURE:
<223> OTHER INFORMATION: Sythetic peptide

<400> SEQUENCE: 40

Gly Ala Val Val Gly Gly Leu Gly Gly Tyr Met Leu Gly Ser
1               5                   10

<210> SEQ ID NO 41
<211> LENGTH: 112
<212> TYPE: PRT
<213> ORGANISM: Artificial Sequence
<220> FEATURE:
<223> OTHER INFORMATION: Sythetic peptide

<400> SEQUENCE: 41

Gly Gly Tyr Met Leu Gly Ser Ala Met Ser Arg Pro Leu Ile Ile Leu
1               5                   10                  15

Pro Arg Ser Met Ala Ser Gly Leu Met Tyr Gly Gly Gly Gly Tyr Met
                20                  25                  30

Leu Gly Ser Ala Met Ser Arg Pro Leu Ile Ile Leu Pro Arg Ser Met
            35                  40                  45

Ala Ser Gly Leu Met Tyr Gly Gly Gly Tyr Met Leu Gly Ser Ala
        50                  55                  60

Met Ser Arg Pro Leu Ile Ile Leu Pro Arg Ser Met Ala Ser Gly Leu
65                  70                  75                  80

Met Tyr Gly Gly Gly Tyr Met Leu Gly Ser Ala Met Ser Arg Pro
                85                  90                  95

Leu Ile Ile Leu Pro Arg Ser Met Ala Ser Gly Leu Met Tyr Gly Gly
                100                 105                 110

<210> SEQ ID NO 42
<211> LENGTH: 112
<212> TYPE: PRT
<213> ORGANISM: Artificial Sequence
<220> FEATURE:
<223> OTHER INFORMATION: Sythetic peptide

<400> SEQUENCE: 42

Gly Ala Val Val Gly Gly Leu Gly Gly Tyr Met Leu Gly Ser Ser Gly
1               5                   10                  15

Leu Met Tyr Gly Gly Leu Gly Gly Val Val Ala Gly Gly Ala Val Val
                20                  25                  30

Gly Gly Leu Gly Gly Tyr Met Leu Gly Ser Ser Gly Leu Met Tyr Gly
            35                  40                  45

Gly Leu Gly Gly Val Val Ala Gly Gly Ala Val Val Gly Gly Leu Gly
        50                  55                  60

Gly Tyr Met Leu Gly Ser Ser Gly Leu Met Tyr Gly Gly Leu Gly Gly
65                  70                  75                  80

Val Val Ala Gly Gly Ala Val Val Gly Gly Leu Gly Gly Tyr Met Leu
                85                  90                  95

Gly Ser Ser Gly Leu Met Tyr Gly Gly Leu Gly Gly Val Val Ala Gly

<210> SEQ ID NO 43
<211> LENGTH: 80
<212> TYPE: PRT
<213> ORGANISM: Artificial Sequence
<220> FEATURE:
<223> OTHER INFORMATION: Sythetic peptide

<400> SEQUENCE: 43

Val Asp Gln Tyr Ser Asn Gln Asn Asn Phe Phe Asn Asn Gln Asn Ser
1               5                   10                  15
Tyr Gln Asp Val Val Asp Gln Tyr Ser Asn Gln Asn Asn Phe Phe Asn
            20                  25                  30
Asn Gln Asn Ser Tyr Gln Asp Val Val Asp Gln Tyr Ser Asn Gln Asn
        35                  40                  45
Asn Phe Phe Asn Asn Gln Asn Ser Tyr Gln Asp Val Val Asp Gln Tyr
    50                  55                  60
Ser Asn Gln Asn Asn Phe Phe Asn Asn Gln Asn Ser Tyr Gln Asp Val
65                  70                  75                  80

<210> SEQ ID NO 44
<211> LENGTH: 8
<212> TYPE: PRT
<213> ORGANISM: Artificial Sequence
<220> FEATURE:
<223> OTHER INFORMATION: Sythetic peptide

<400> SEQUENCE: 44

Gly Tyr Val Leu Gly Ser Ala Met
1               5

<210> SEQ ID NO 45
<211> LENGTH: 9
<212> TYPE: PRT
<213> ORGANISM: Artificial Sequence
<220> FEATURE:
<223> OTHER INFORMATION: Sythetic peptide

<400> SEQUENCE: 45

Gly Tyr Val Leu Gly Ser Ala Met Ser
1               5

<210> SEQ ID NO 46
<211> LENGTH: 10
<212> TYPE: PRT
<213> ORGANISM: Artificial Sequence
<220> FEATURE:
<223> OTHER INFORMATION: Sythetic peptide

<400> SEQUENCE: 46

Gly Tyr Val Leu Gly Ser Ala Met Ser Arg
1               5                   10

<210> SEQ ID NO 47
<211> LENGTH: 11
<212> TYPE: PRT
<213> ORGANISM: Artificial Sequence
<220> FEATURE:
<223> OTHER INFORMATION: Sythetic peptide

<400> SEQUENCE: 47

Gly Tyr Val Leu Gly Ser Ala Met Ser Arg Pro
1               5                   10

<210> SEQ ID NO 48
<211> LENGTH: 134
<212> TYPE: PRT
<213> ORGANISM: Artificial Sequence
<220> FEATURE:
<223> OTHER INFORMATION: Sythetic peptide

<400> SEQUENCE: 48

```
Gly Ser Val Asp Gln Tyr Ser Asn Gln Asn Asn Phe Phe Asn Gln
1               5                   10                  15

Asn Ser Tyr Gln Asp Val Phe Asn Asn Gln Asn Ser Tyr Gln Asp Val
            20                  25                  30

Ser Gly Ser Val Asp Gln Tyr Ser Asn Gln Asn Asn Phe Phe Asn Asn
        35                  40                  45

Gln Asn Ser Tyr Gln Asp Val Phe Asn Asn Gln Asn Ser Tyr Gln Asp
    50                  55                  60

Val Gly Ser Ser Val Asp Gln Tyr Ser Asn Gln Asn Asn Phe Phe Asn
65                  70                  75                  80

Asn Gln Asn Ser Tyr Gln Asp Val Phe Asn Asn Gln Asn Ser Tyr Gln
                85                  90                  95

Asp Val Ser Gly Ser Val Asp Gln Tyr Ser Asn Gln Asn Asn Phe Phe
            100                 105                 110

Asn Asn Gln Asn Ser Tyr Gln Asp Val Phe Asn Asn Gln Asn Ser Tyr
        115                 120                 125

Gln Asp Val Ser Gly Ser
    130
```

<210> SEQ ID NO 49
<211> LENGTH: 457
<212> TYPE: PRT
<213> ORGANISM: Artificial Sequence
<220> FEATURE:
<223> OTHER INFORMATION: Synthetic peptide

<400> SEQUENCE: 49

```
Met Val Pro Gln Ala Leu Leu Phe Val Pro Leu Leu Ala Phe Pro Met
1               5                   10                  15

Cys Phe Gly Lys Phe Pro Ile Tyr Thr Ile Pro Asp Lys Leu Gly Pro
            20                  25                  30

Trp Ser Pro Ile Asp Ile His His Leu Ser Cys Pro Asn Asn Leu Val
        35                  40                  45

Val Glu Asp Glu Gly Cys Thr Asn Leu Ser Gly Phe Ser Tyr Met Glu
    50                  55                  60

Leu Lys Val Gly Tyr Ile Ser Ala Ile Lys Val Asn Gly Phe Thr Cys
65                  70                  75                  80

Thr Gly Val Val Thr Glu Ala Glu Thr Tyr Thr Asn Phe Val Gly Tyr
                85                  90                  95

Val Thr Thr Thr Phe Lys Arg Lys His Phe Arg Pro Thr Pro Asp Ala
            100                 105                 110

Cys Arg Ala Ala Tyr Asn Trp Lys Met Ala Gly Asp Pro Arg Tyr Glu
        115                 120                 125

Glu Ser Leu His Asn Pro Tyr Pro Asp Tyr His Trp Leu Arg Thr Val
    130                 135                 140

Lys Thr Thr Lys Glu Ser Leu Ile Ile Ile Ser Pro Ser Val Ala Asp
145                 150                 155                 160

Leu Asp Pro Tyr Asp Lys Ser Leu His Ser Arg Val Phe Pro Ser Gly
                165                 170                 175
```

-continued

```
Lys Cys Leu Gly Ile Thr Ile Ser Ser Thr Tyr Cys Ser Thr Asn His
            180             185             190

Asp Tyr Thr Ile Trp Met Pro Glu Asn Val Arg Leu Gly Thr Ser Cys
        195             200             205

Asp Ile Phe Thr Asn Ser Arg Gly Lys Arg Ala Ser Lys Gly Ser Lys
    210             215             220

Thr Cys Gly Phe Val Asp Glu Arg Gly Leu Tyr Lys Ser Leu Lys Gly
225             230             235                         240

Ala Cys Lys Leu Lys Leu Cys Gly Val Leu Gly Leu Arg Leu Met Asp
                245             250             255

Gly Thr Trp Val Ala Met Pro Thr Ser Asp Glu Thr Lys Trp Cys Pro
            260             265             270

Pro Asp Gln Leu Val Asn Leu His Asp Phe Arg Ser Asp Glu Ile Glu
        275             280             285

His Leu Val Val Glu Glu Leu Val Arg Lys Arg Glu Glu Cys Leu Asp
    290             295             300

Ala Leu Glu Ser Ile Met Thr Thr Lys Ser Val Ser Phe Arg Arg Leu
305             310             315                         320

Ser His Leu Arg Lys Leu Val Pro Gly Phe Gly Lys Ala Tyr Thr Ile
                325             330             335

Phe Asn Lys Thr Leu Met Glu Ala Asp Ala His Tyr Lys Ser Val Arg
            340             345             350

Thr Trp Asn Glu Ile Ile Pro Ser Lys Gly Cys Leu Arg Val Gly Gly
        355             360             365

Arg Cys His Pro His Val Asn Gly Val Phe Phe Asn Gly Ile Ile Leu
    370             375             380

Gly Pro Asp Gly His Val Leu Ile Pro Glu Met Gln Ser Ser Leu Leu
385             390             395                         400

Gln Gln His Met Glu Leu Leu Glu Ser Ser Val Ile Pro Leu Met His
                405             410             415

Pro Leu Ala Asp Pro Ser Thr Val Phe Lys Asp Gly Asp Glu Ala Glu
            420             425             430

Asp Phe Val Glu Val His Leu Pro Asp Val His Lys Gln Ile Ser Gly
        435             440             445

Val Asp Leu Gly Leu Pro Asn Trp Gly
    450             455
```

PRION DISEASE-SPECIFIC EPITOPES AND METHODS OF USE THEREOF

CROSS-REFERENCE TO RELATED APPLICATION

This application claims the benefit under 35 U.S.C. §119 (e)(1) of U.S. Provisional Application No. 61/817,827, filed Apr. 30, 2013 and U.S. Provisional Application No. 61/899,989, filed Nov. 5, 2013, which applications are incorporated herein by reference in their entireties.

TECHNICAL FIELD

The present invention pertains generally to prion diseases and immunogenic compositions and methods for treating, preventing and diagnosing prion infection. In particular, the invention relates to particular prion disease-specific epitopes that display enhanced immunogenicity, and uses thereof.

BACKGROUND

Transmissible spongiform encephalopathies (TSEs), or prion diseases, represent a novel molecular mechanism of infectivity, based on the misfolding of a self-protein designated $PrP^C$ into a pathological, infectious conformation termed $PrP^{Sc}$. Through this model, $PrP^{Sc}$ serves as a template to convert the normal cellular protein ($PrP^C$) into the infectious conformation ($PrP^{Sc}$) in an autocatalytic, self-propagating manner (Aguzzi et al., Annu. Rev. Pathol. (2008) 3:11-40).

Prion diseases affect a number of domestic species causing scrapie in sheep, bovine spongiform encephalopathy (BSE) in cattle and chronic wasting disease (CWD) in cervids such as deer and elk (Silveira et al., Curr. Top. Microbiol. Immunol. (2004) 284:1-50). Human manifestations of the prion diseases include Creutzfeldt-Jakob disease (CJD), Gerstmann-Straussler-Sheinker syndrome, and fatal familial insomnia (Collinge, Ann. Rev. Neurosci. (2001) 24:519-550). In the absence of any effective therapies, prion diseases currently have a fatal outcome in all species (Geshwind, Lancet Neurol. (2009) 8:304-306). The infectious component of prion disease ($PrP^{Sc}$) is characterized by increased β-sheet content and extreme structural stability. The unique persistence of this infectious conformation in the environment has severe implications on both disease dynamics and strategies for disease control (Wiggins, Neurochem. Res. (2009) 34:158-68).

Natural transmission of $PrP^{Sc}$ within populations often occurs following ingestion of contaminated environmental material (Williams, Veterinary Pathology (2005) 42:530-549). The recycling of contaminated animal materials in feed provides an additional mechanism of transmission specific to livestock (Bradley, Livestock Production Science (1994) 38:5-16). Accordingly, efforts to control prion transmission in livestock have focused on removal of these high-risk animal-based components of feed, thereby reducing animal exposure to infectious $PrP^{Sc}$ (Smith et al., Br. Med. Bull. (2003) 66:185-198). While this approach enabled prion diseases of livestock to be sufficiently controlled, environmental contamination and spontaneous disease still enable BSE to persist, albeit at low levels. This highlights the inability of current management tools and practices to completely eliminate the threat of BSE in the food supply.

Although BSE infection of cattle has been the most publicized TSE, chronic wasting disease of cervids has recently emerged as the prion disease of most concern in livestock. CWD first surfaced in Colorado in the 1960s and was later classified as a prion disease in 1978 (Williams, J. Wildl. Dis. (1980) 16:89-98). At the time of initial identification of CWD in wild cervids, the disease was believed to be confined to a small demographic. Since then, CWD endemic areas have undergone dramatic geographical expansion, to include extensive regions of both the United States and Canada. The presence of CWD in both farmed and wild cervids, coupled with the large geographic spread, and uncontrolled transmission of this disease, suggests CWD may be one of the most contagious TSEs (Williams, Veterinary Pathology (2005) 42:530-549). The management of CWD in the wild is also complicated by the free-ranging dynamic of infected populations and the opportunity to overcome species barriers through intermediate species such as crows (verCauteren et al., PLoS one (2012) 7:e45774), rodents (Heisey et al., J. Virol. (2010) 84:210-215), and voles (Nonno et al., PLoS pathogens (2006) 2:e12).

Due to the importance of cervids in the hunting, tourism, and agricultural industries, CWD has the potential for severe economic and human health implications (Saunders et al., Emerg. Infect. Dis. (March 2012) 18(3). There are no confirmed cases of human infection with CWD. This could, however, reflect low transmissibility across species to humans, extensive latency periods, and relatively low levels of human consumption of CWD-infected animals. Importantly, transmission of CWD to humans could occur either through direct transmission to humans through consumption of infected cervid meat or indirectly through infection of a secondary species such as cattle. The potential for disease transmission between cervids and cattle is a possibility, due to the close ecological and phylogenetic relationship of these species (Sigurdson and Agguzi, Biochimica et Biophysica Acta (2007) 772:610-618). Cerebral inoculation of cattle with CWD material results in the development of a TSE (Hamir et al., J. Vet. Diagn. Invest. (2001) 13:91-96). Although this method of infection is quite extreme, the potential for CWD to overcome this species barrier is still a possibility.

Thus, there is a clear need for strategies to prevent and treat prion diseases of humans and animals. There have been numerous studies examining the use of immunotherapy for prion diseases. In this regard, several studies have demonstrated the ability of antibodies against $PrP^C$, or specific fragments of the protein, to offer protection in both in vitro and in vivo models (Enari et al., Proc. Natl. Acad. Sci. USA (2001) 98:9295-9299; Perrier et al., J. Neurochem. (2004) 89:454-463). This includes passive and active immunization as well as engineered expression of $PrP^C$ binding fragments (White et al., Nature (2003) 422:80-83; Sigurdsson et al., Neurosci. Lett. (2003) 336:185-187; Sigurdsson et al., Am. J. Pathol. (2002) 161:13-17; Peretz et al., Nature (2001) 412:739-743). However, these studies fell short of providing either a prophylactic or therapeutic prion vaccine.

While these findings are encouraging, a number of practical considerations must be addressed prior to the development of a real-world prion vaccine. One of the main challenges for prion vaccine development is overcoming tolerance to $PrP^C$. There have been a number of investigations that attempted, with varying degrees of success, to overcome self-tolerance and induce strong antibody responses to $PrP^C$ protein. These investigations have employed a variety of different carrier systems and adjuvants to induce antibody responses (Hanan et al., Biochem. Biophys. Res. Commun. (2001) 280: 115-120; Koller et al., J. Neuroimmunol. (2002) 132:113-116; Sigurdsson et al., Am. J. Pathol. (2002) 161:13-17; Rosset et al., J. Immunol.

(2004) 172: 5168-5174; Polymenidou et al., *Proc. Natl. Acad. Sci. USA* (2004) 101 Suppl 2:14670-14676; Schwarz et al., *Neurosci. Lett.* (2003) 350:187-189; Gilch et al., *J. Biol. Chem.* (2003) 278:18524-18531). Notably, however, many of these investigations resort to harsh adjuvants and vaccination regimens that are impractical for either humans or livestock.

Importantly, the strategy for overcoming self-tolerance must also incorporate a method for limiting antibody reactivity with non-pathogenic conformations of $PrP^C$. Due to the ubiquitous expression of this cell surface protein, the generation of circulating $PrP^C$ antibodies may result in a variety of adverse consequences in vivo, both functional and immunological. For example, antibody binding may initiate improper activation of $PrP^C$-based cell signaling cascades (Cashman et al., *Cell* (1990) 61:185-192; Schneider et al., *Proc. Natl. Acad. Sci. USA* (2003) 100:13326-13331; Arsenault et al., *Prion* (2012) 6:477-488), or trigger apoptosis in neurons (Solforosi et al., *Science* (2004) 303:1514-1516). The activation of a non-discriminating antibody response to $PrP^C$ may result in the subsequent activation of complement-dependent cell lysis, facilitated by antibody binding to $PrP^C$ at the cell surface, or may facilitate the development of autoimmune disease, by breaking $PrP^C$ tolerance. Although the exact physiological role of $PrP^C$ has yet to be fully elucidated, ideally, an effective prion vaccine would be specific to $PrP^{Sc}$. The strategy for conformation specific targeting of $PrP^{Sc}$ requires the identification of epitope regions that are surface exposed in the infectious misfolded conformation, yet remain concealed in the non-pathogenic isoform.

It has been reported that a YYR motif was specifically exposed upon experimental misfolding of $PrP^C$ (Paramithiotis et al., *Nature Medicine* (2003) 9:893-899). U.S. Pat. No. 7,041,807 describes rabbit polyclonal antisera raised against the YYR peptide and immunoprecipitation of $PrP^{Sc}$ from scrapie-infected mouse brain but did not $PrP^C$ from uninfected brains. However, the opportunity to translate this epitope into a vaccine was restricted by the minimal immunogenicity of this motif; $PrP^{Sc}$-specific monoclonal antibodies (mAbs) were restricted to IgM isotype after multiple immunizations with Freunds complete adjuvant (Paramithiotis et al., *Nature Medicine* (2003) 9:893-899). Strategies of formulation and delivery, including presenting the peptide in the context of a potent carrier system designed to facilitate antibody responses to self peptides, still failed to generate epitope specific immune responses. Sequence optimization of the core epitope was essential to generate more immunogenic peptides.

U.S. Patent Publ. 2009/0280125 describes chimeric vaccines representing various expansions around the YYR core. Screening of these vaccines in animals identified expansions that satisfied the criteria of increased immunogenicity while retaining $PrP^{Sc}$ specificity. As such, this approach was successful but time consuming and labor intensive.

U.S. Patent Publ. 2012/0107321 describes a second prion disease-specific epitope designated YML. The YML epitope also shows prion-specific exposure, and is not present at the surface of normal cells when probed with antibody and analyzed by flow cytometry.

Despite the above advances, there remains a need for the development of effective strategies for the treatment, prevention and diagnosis of prion infection.

SUMMARY OF THE INVENTION

The present invention is based on the production of peptides comprising prion disease-specific epitopes (DSEs) derived from the YML region of β-sheet 1 and from the rigid loop (RL) linking β-sheet 2 to α-helix 2. In particular, the inventors herein, have expanded these sequences to include B cell epitopes. This strategy involved creation of a comprehensive panel of expansions of the $PrP^{Sc}$ specific core epitopes, followed by in silico analysis using an algorithm that identified sequence signatures associated with B cell epitopes. From this approach, proposed DSEs were rapidly translated into immunogenic vaccines capable of inducing $PrP^{Sc}$-specific immune responses. These vaccines, individually or combined as a multivalent vaccine, can be used for immunotherapy and immunoprophylaxis of prion diseases. This DSE expansion strategy enables the rapid identification of highly immunogenic peptide-epitopes, which can easily be incorporated into established strategies for vaccine formulation and delivery, accelerating the production of effective peptide-based vaccines.

Thus, the invention relates to peptides comprising prion disease-specific epitopes, polynucleotides encoding these peptides, and antibodies generated using these peptides. The peptides induce robust, $PrP^{Sc}$-specific antibody responses. Thus, the peptides, polynucleotides and/or antibodies described herein are useful in compositions and methods for treating and preventing prion diseases, as well as for detecting the presence of pathogenic prions, for example in a biological sample.

Due to the specificity of the antibodies directed against peptides of the invention, the risk of adverse effects that may occur using $PrP^c$-specific immunoprophylaxis is reduced. Moreover, the uptake and destruction of infectious prions by cells, such as tingible body macrophages may be enhanced, before they become completely resistant to proteases. Furthermore, $PrP^{Sc}$-specific antibodies may impair the interaction between $PrP^c$ and $PrP^{Sc}$ which is a prerequisite for the recruitment process to form prion protein.

Accordingly, in one embodiment, the invention is directed to an isolated immunogenic peptide selected from a peptide comprising (a) the sequence GYMLGSAMSRP (SEQ ID NO:17); (b) the sequence VDQYSNQNNF (SEQ ID NO:19); or (c) a sequence corresponding to (a) or (b) from another species. In certain embodiments, the peptide is present in a fusion peptide comprising two or more repeats of the above peptides in a linear or an inverted orientation. Linker amino acids may be present between the repeats.

In further embodiments, the peptide comprises two or more repeats of the amino acid sequence GYMLGSAMSRP (SEQ ID NO:17) and/or two or more repeats of the amino acid sequence VDQYSNQNNF (SEQ ID NO:19), in a linear or an inverted orientation. Linker amino acids may be present between the repeats.

In additional embodiments, the fusion peptide comprises the amino acid sequence of SEQ ID NO:38, SEQ ID NO:43 or SEQ ID NO:48.

In yet further embodiments, the invention is directed to an immunogenic peptide comprising the amino acid sequence of SEQ ID NO:37.

In certain embodiments, the immunogenic peptides of above are linked to a carrier molecule.

In additional embodiments, the carrier molecule is capable of enhancing the immunogenicity of the immunogenic peptide. In further embodiments, the carrier molecule is an RTX toxin, such as a leukotoxin peptide, such as LKT 352, or a lyssavirus G protein, or a portion thereof, such as a lyssavirus G protein lacking all or a portion of the C-terminal cytoplasmic and transmembrane domains.

In further embodiments, the invention is directed to a composition comprising one or more of the immunogenic peptides above and a pharmaceutically acceptable vehicle. In certain embodiments, the composition comprises an immunogenic peptide with the amino acid sequence of SEQ ID NO:38 and an immunogenic peptide with the amino acid sequence of SEQ ID NO:43. In additional embodiments, the composition further comprises an immungenic peptide with the amino acid sequence of SEQ ID NO:37.

In additional embodiments, the invention is directed to a method of producing a composition comprising combining any one of the immunogenic peptides above with a pharmaceutically acceptable vehicle.

In further embodiments, the invention is directed to a polynucleotide comprising a coding sequence encoding an immunogenic peptide described above. In additional embodiments, the invention is directed to a recombinant vector comprising: (a) the polynucleotide; and (b) control elements that are operably linked to the polynucleotide whereby said coding sequence can be transcribed and translated in a host cell. In certain embodiments, the invention is directed to a host cell transformed with the recombinant vector.

In additional embodiments, the invention is directed to a method of producing an immunogenic peptide comprising: (a) providing a population of host cells as above; and (b) culturing the population of cells under conditions whereby the peptide encoded by the coding sequence present in said recombinant vector is expressed.

In further embodiments, the invention is directed to a composition comprising the polynucleotide above and a pharmaceutically acceptable vehicle. In additional embodiments, the invention is directed to a method of producing a composition comprising combining the polynucleotide with a pharmaceutically acceptable vehicle.

In yet additional embodiments, the invention is directed to antibodies specific for an immunogenic peptide above, such as polyclonal or monoclonal antibodies. In certain embodiments, the antibodies are present in a composition which comprises a pharmaceutically acceptable vehicle. In additional embodiments, the invention is directed to a method of producing a composition comprising combining the antibodies with a pharmaceutically acceptable vehicle.

In further embodiments, the invention is directed to a method of treating or preventing a prion disease comprising administering a therapeutic amount of any one of the compositions above to a subject in need thereof.

In additional embodiments, the invention is directed to a method of detecting prion antibodies in a biological sample comprising: (a) providing a biological sample; (b) reacting the biological sample with an immunogenic peptide as described above under conditions which allow prion antibodies, when present in the biological sample, to bind to the immunogenic peptide to form an antibody/antigen complex; and (c) detecting the presence or absence of the complex, thereby detecting the presence or absence of prion antibodies in said sample.

In further embodiments, the invention is directed to an immunodiagnostic test kit for detecting prion infection, the test kit comprising any one of the immunogenic peptides above, and instructions for conducting the immunodiagnostic test.

These and other embodiments of the subject invention will readily occur to those of skill in the art in view of the disclosure herein.

BRIEF DESCRIPTION OF THE FIGURES

FIG. 1 shows an alignment of the PrP protein from sheep (SEQ ID NO:1), bovine (SEQ ID NO:2), human (SEQ ID NO:3), mouse (SEQ ID NO:4), elk (SEQ ID NO:5), mule deer (SEQ ID NO:6), and whitetail deer (SEQ ID NO:7). The YYR DSE, as well as the YML and RL DSEs are bolded.

FIG. 2 depicts the structure of Plasmid pAA352 wherein tac is the hybrid trp::lac promoter from *E. coli*; bla represents the β-lactamase gene (ampicillin resistance); on is the ColE1-based plasmid origin of replication; lktA is the *P. haemolytica* leukotoxin structural gene; and lacl is the *E. coli* lac operon repressor. The direction of transcription/translation of the leukotoxin gene is indicated by the arrow. The size of each component is not drawn to scale.

FIGS. 3A-3F (SEQ ID NOS:8, 9 and 10) show the nucleotide sequence and predicted amino acid sequence of leukotoxin 352 (LKT 352) from plasmid pAA352. Both the structural gene for LKT 352 and the sequences of the flanking vector regions are shown.

FIGS. 4A-4B show immunogenicity of serial expansions of the YYR epitope. FIG. 4A shows serum antibody titres, determined by peptide-capture ELISAs. Data is presented as median values. The dashed line indicates the threshold for a positive titre as greater than 1000. FIG. 4B shows individual animal responses, presented for week 7 which was the time of peak antibody. Significant differences ($p<0.01$) among the treatment groups are indicated. Peak carrier specific immune responses are presented for week 7.

FIGS. 5A-5B show that in silico expansion improves the immunogenicity of the YML DSE. Serum epitope specific antibody titres were determined using peptide-capture ELISAs. The dashed line indicates the threshold for a positive response, at a titre of 1000. Comparison of median serum antibody titres throughout the 10-week time-course (FIG. 5A) and peak serum antibody titres (FIG. 5B) are shown for each vaccine construct.

FIGS. 6A-6D show the immunogenicity of the expanded DSE-based vaccines in mice. FIG. 6A shows individual animal antibody titres for YYR. FIG. 6B shows individual antibody titres for YML, and FIG. 6C shows individual antibody titres for RL. Median titres for each DSE vaccine are compared in FIG. 6D. The dashed line indicates the threshold for a positive response, at a titre of 1000.

FIGS. 7A-7C show the immunogenicity of various DSE-based vaccines administered alone, co-Administered and co-Formulated. FIG. 7A shows individual peptide-specific serum antibody titres FIG. 7B is a comparison of median titres specific for each peptide antigen when using different vaccine delivery and formulation formats. FIG. 7C shows the effect of vaccine formulation and delivery on peptide-specific antibody titres specific for each DSE.

FIGS. 8A-8B show immune responses in mucosal secretions in sheep immunized with the expanded DSEs in univalent, multivalent co-administered, and multivalent co-formulated formats. FIG. 8A shows epitope specific mucosal IgA antibody titres. FIG. 8B shows regression analysis of log transformed mucosal IgA vs serum IgG antibody titres. ($R2=0.4494$, $P<0.0001$, Pearson $r=0.6704$).

FIG. 9 shows the conformational specificity of the antibodies generated against the YML, YYR, and RL epitopes by immunoprecipitation of $PrP^{C}$ from non-infected and $PrP^{Sc}$ from infected brain homogenates.

FIG. 10 shows a representative amino acid sequence (SEQ ID NO:49) of a lyssavirus G protein for use as a carrier with the present invention. The sequence includes a truncation of the C-terminal transmembrane and cytoplasmic domains.

FIGS. 11A and 11B show the magnitude and duration of antibody responses to RL PrP DSE (SEQ ID NO:48) following immunizations with tgG-RL (tgG) or Lkt-RL (Lkt). C57/BL6 (n=6) mice were injected subcutaneously with either 10 μg tgG-RL or Lkt-RL formulated in 30% EMULSIGEN D. Animals were immunized (arrow) twice with a three-week interval (FIG. 11A) or received a single immunization (arrow) on day 0 (FIG. 11B). Antibody titers were quantified by capture ELISA using the DSE peptide, and are reported as mean values±1 SD.

FIGS. 12A and 12B show the isotype of DSE IgG antibodies as analyzed 9 weeks following a single subcutaneous immunization with either 10 μg tgG-RL (FIG. 12A) or Lkt-RL (FIG. 12B) formulated in 30% EMULSIGEN D. Data presented are values for individual C57BL/6 mice (n=6) and the horizontal bar represents the mean value for each treatment group. $IgG_1$ and $IgG_{2c}$ DSE-specific serum antibodies were quantified by capture ELISA using DSE peptides.

FIGS. 13A and 13B show the cytokine secretion profile of splenocytes isolated from BALB/c mice 5 weeks after a single subcutaneous injection n of either 10 μg tgG-RL (13A) or Lkt-RL (13B) formulated in 30% EMULSIGEN D. Results are expressed as number of cytokine-secreting cells per million cells re-stimulated with either RL peptide (peptide), tgG carrier protein (tgG), or Lkt carrier protein (Lkt). Data presented are the mean±1SD of values from 6 mice per group.

DETAILED DESCRIPTION OF THE INVENTION

Figure 2:
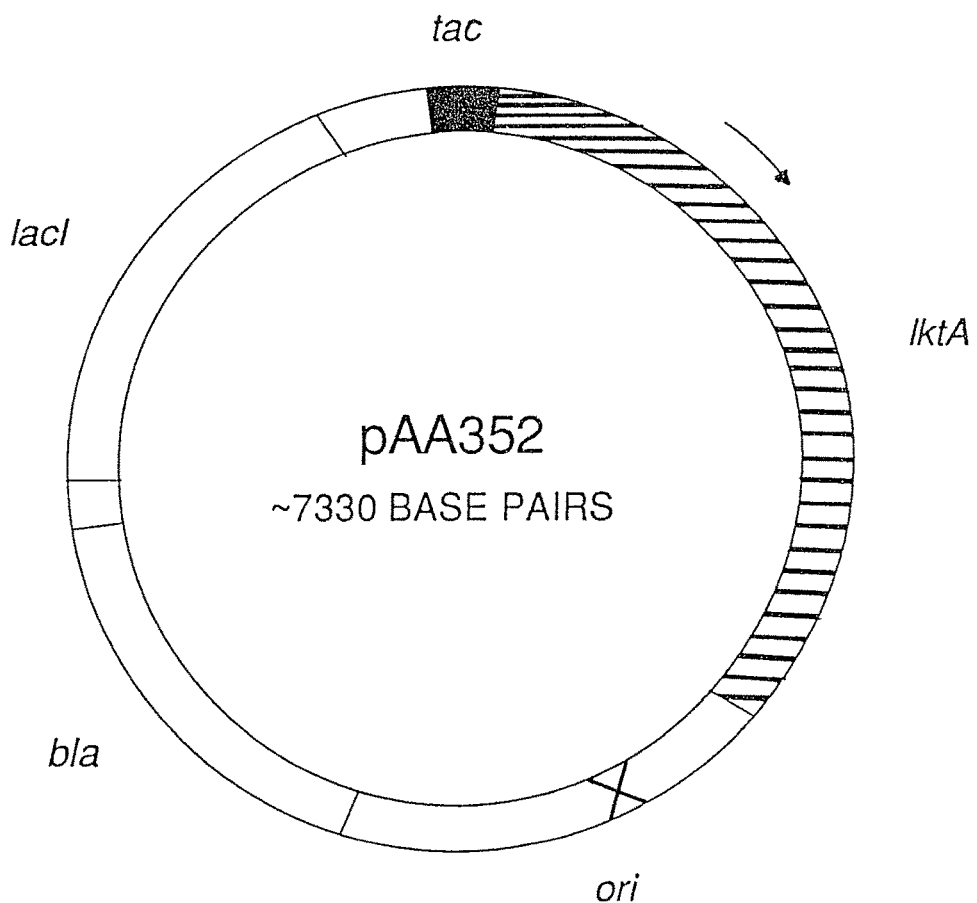

The practice of the present invention will employ, unless otherwise indicated, conventional methods of chemistry, biochemistry, recombinant DNA techniques and immunology, within the skill of the art. Such techniques are explained fully in the literature. See, e.g., *Handbook of Experimental Immunology*, Vols. I-IV (D. M. Weir and C. C. Blackwell eds., Blackwell Scientific Publications); T. E. Creighton, *Proteins: Structures and Molecular Properties* (W.H. Freeman and Company); A. L. Lehninger, *Biochemistry* (Worth Publishers, Inc.); Sambrook, et al., *Molecular Cloning: A Laboratory Manual; Methods In Enzymology* (S. Colowick and N. Kaplan eds., Academic Press, Inc.); *Remington's Pharmaceutical Sciences*, (Easton, Pa.: Mack Publishing Company; *Methods In Enzymology* (S. Colowick and N. Kaplan, eds., Academic Press, Inc.

All publications, patents and patent applications cited herein, whether supra or infra, are hereby incorporated by reference in their entireties.

The following amino acid abbreviations are used throughout the text:

| | |
|---|---|
| Alanine: Ala (A) | Arginine: Arg (R) |
| Asparagine: Asn (N) | Aspartic acid: Asp (D) |
| Cysteine: Cys (C) | Glutamine: Gln (Q) |
| Glutamic acid: Glu (E) | Glycine: Gly (G) |
| Histidine: His (H) | Isoleucine: Ile (I) |
| Leucine: Leu (L) | Lysine: Lys (K) |
| Methionine: Met (M) | Phenylalanine: Phe (F) |
| Proline: Pro (P) | Serine: Ser (S) |
| Threonine: Thr (T) | Tryptophan: Trp (W) |
| Tyrosine: Tyr (Y) | Valine: Val (V) |

1. Definitions

In describing the present invention, the following terms will be employed, and are intended to be defined as indicated below.

It must be noted that, as used in this specification and the appended claims, the singular forms "a", "an" and "the" include plural referents unless the content clearly dictates otherwise. Thus, for example, reference to "a peptide" includes a mixture of two or more such peptides, and the like.

As used herein, the term "prion" refers to a proteinaceous infectious agent that lacks nucleic acid. (See, e.g., Bolton, et al., *Science* (1982) 218:1309-1311; Prusiner, et al., *Biochemistry* (1982) 21:6942-6950; McKinley, et al. *Cell* (1983) 35:57-62; and Prusiner, *Proc. Natl. Acad. Sci. USA* (1998) 95:13363-13383. As explained above, the prion protein occurs normally in the nonpathogenic $PrP^C$ form and under appropriate conditions, is folded into the pathogenic $PrP^{Sc}$ form. The pathogenic conformation of the prion protein typically includes at least one region that can adapt a β-helical conformation (referred to as a "β-helical region"). Prions are naturally produced in a wide variety of mammalian species, including human, sheep, cattle, mice, deer, elk, among others.

By "prion disease" is meant a disease caused in whole or in part by a pathogenic prion particle ($PrP^{Sc}$). In humans these diseases include Creutzfeldt-Jakob disease (CJD), Gerstmann-Straussler-Scheinker syndrome (GSS), Fatal Familial Insomnia (FFI), and Kuru (see, e.g., Harrison's Principles of Internal Medicine, Isselbacher et al., eds., McGraw-Hill, Inc. New York, (1994); Medori et al., *N. Engl. J. Med.* (1992) 326: 444-449.). In non-human mammals, the diseases include sheep scrapie, bovine spongiform encephalopathy (BSE), transmissible mink encephalopathy, and chronic wasting disease of captive mule deer and elk (Gajdusek, (1990) Subacute Spongiform Encephalopathies: Transmissible Cerebral Amyloidoses Caused by Unconventional Viruses. Pp. 2289-2324 In: Virology, Fields, ed. New York: Raven Press, Ltd.).

The terms "polypeptide" and "protein" refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include postexpression modifications of the polypeptide, for example, glycosylation, acetylation, phosphorylation and the like. Furthermore, for purposes of the present invention, a "polypeptide" refers to a protein which includes modifications, such as deletions, additions and substitutions, to the native sequence, so long as the protein maintains the desired activity. These modifications may be deliberate, as through site-directed mutagenesis, or may be accidental, such as through mutations of hosts which produce the proteins or errors due to PCR amplification.

The term "peptide" as used herein refers to a fragment of a polypeptide. Thus, a peptide can include a C-terminal deletion, an N-terminal deletion and/or an internal deletion of the native polypeptide, so long as the entire protein sequence is not present. A peptide will generally include at least about 3-10 contiguous amino acid residues of the full-length molecule, and can include at least about 15-25 contiguous amino acid residues of the full-length molecule, or at least about 20-50 or more contiguous amino acid residues of the full-length molecule, or any integer between 3 amino acids and the number of amino acids in the full-length sequence, provided that the peptide in question retains the ability to elicit the desired biological response.

A prion "peptide" is a polypeptide that includes less than the full-length sequence of a prion protein. Moreover, a prion peptide will include at least one epitope such that an immunologic response can be generated. A prion peptide can be derived from any species, such as, but not limited to, any of the PrP sequences shown in FIG. 1. A prion peptide can include a portion of the native PrP sequence, repeats of a portion of the native sequence as linear repeats or inverted repeats in a symmetrical or asymmetrical orientation (discussed more fully below), or can include amino acid sequences from multiple species, or even non-prion sequences.

By "immunogenic" protein, polypeptide or peptide is meant a molecule which includes one or more epitopes and thus can modulate an immune response. Such peptides can be identified using any number of epitope mapping techniques, well known in the art. See, e.g., *Epitope Mapping Protocols* in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) *Proc. Natl. Acad. Sci. USA* 81:3998-4002; Geysen et al. (1986) *Molec. Immunol.* 23:709-715, all incorporated herein by reference in their entireties. Similarly, conformational epitopes are readily identified by determining spatial conformation of amino acids such as by, e.g., x-ray crystallography and 2-dimensional nuclear magnetic resonance. See, e.g., *Epitope Mapping Protocols*, supra. Antigenic regions of proteins can also be identified using standard antigenicity and hydropathy plots, such as those calculated using, e.g., the Omiga version 1.0 software program available from the Oxford Molecular Group. This computer program employs the Hopp/Woods method, Hopp et al., *Proc. Natl. Acad. Sci. USA* (1981) 78:3824-3828 for determining antigenicity profiles, and the Kyte-Doolittle technique, Kyte et al., *J. Mol. Biol.* (1982) 157:105-132 for hydropathy plots.

Immunogenic peptides, for purposes of the present invention, will usually be at least about 2 amino acids in length, more preferably about 5 amino acids in length, and even at least about 10 to about 15 amino acids in length. There is no critical upper limit to the length of the peptide, which can comprise nearly the full-length of the protein sequence, or even a fusion protein comprising two or more epitopes.

As used herein, the term "epitope" generally refers to the site on an antigen which is recognized by a T-cell receptor and/or an antibody. Preferably it is a short peptide derived from or as part of a protein antigen. Several different epitopes may be carried by a single antigenic molecule. The term "epitope" also includes modified sequences of amino acids which stimulate responses which recognize the whole organism. The epitope can be generated from knowledge of the amino acid and corresponding DNA sequences of the peptide or polypeptide, as well as from the nature of particular amino acids (e.g., size, charge, etc.) and the codon dictionary, without undue experimentation. See, e.g., Ivan Roitt, Essential Immunology, 1988; Kendrew, supra; Janis Kuby, Immunology, 1992 e.g., pp. 79-81.

An "immunological response" to an antigen or composition is the development in a subject of a humoral and/or a cellular immune response to an antigen present in the composition of interest. For purposes of the present invention, a "humoral immune response" refers to an immune response mediated by antibody molecules, while a "cellular immune response" is one mediated by T-lymphocytes and/or other white blood cells. One important aspect of cellular immunity involves an antigen-specific response by cytolytic T-cells ("CTL"s). CTLs have specificity for peptide antigens that are presented in association with proteins encoded by the major histocompatibility complex (MHC) and expressed on the surfaces of cells. CTLs help induce and promote the destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells.

Thus, an immunological response as used herein may be one that stimulates the production of antibodies. The antigen of interest may also elicit production of CTLs. Hence, an immunological response may include one or more of the following effects: the production of antibodies by B-cells; and/or the activation of suppressor T-cells and/or memory/effector T-cells directed specifically to an antigen or antigens present in the composition or vaccine of interest. These responses may serve to neutralize infectivity, and/or mediate antibody-complement, or antibody dependent cell cytotoxicity (ADCC) to provide protection to an immunized host. Such responses can be determined using standard immunoassays and neutralization assays, well known in the art. (See, e.g., Montefiori et al. (1988) *J. Clin Microbiol.* 26:231-235; Dreyer et al. (1999) *AIDS Res Hum Retroviruses* (1999) 15(17):1563-1571). The innate immune system of mammals also recognizes and responds to molecular features of pathogenic organisms via activation of Toll-like receptors and similar receptor molecules on immune cells. Upon activation of the innate immune system, various non-adaptive immune response cells, are activated to, e.g., produce various cytokines, lymphokines and chemokines. Cells activated by an innate immune response include immature and mature Dendritic cells of the monocyte and plasmacytoid lineage (MDC, PDC), as well as gamma, delta, alpha and beta T cells and B cells and the like. Thus, the present invention also contemplates an immune response wherein the immune response involves both an innate and adaptive response.

An "immunogenic composition" is a composition that comprises an immunogenic molecule where administration of the composition to a subject results in the development in the subject of a humoral and/or a cellular immune response to the molecule of interest.

An "antigen" refers to a molecule, such as a protein, polypeptide, or fragment thereof, containing one or more epitopes (either linear, conformational or both) that will stimulate a host's immune-system to make a humoral and/or cellular antigen-specific response. The term is used interchangeably with the term "immunogen." Antibodies such as anti-idiotype antibodies, or fragments thereof, and synthetic peptide mimotopes, which can mimic an antigen or antigenic determinant, are also captured under the definition of antigen as used herein. Similarly, an oligonucleotide or polynucleotide which expresses an antigen or antigenic determinant in vivo, such as in DNA immunization applications, is also included in the definition of antigen herein.

By "carrier" is meant any molecule which when associated with an antigen of interest, imparts increased immunogenicity to the antigen.

The term "RTX" toxin, as used herein refers to a protein belonging to the family of molecules characterized by the carboxy-terminus consensus amino acid sequence Gly-Gly-X-Gly-X-Asp (SEQ ID NO:11, Highlander et al., *DNA* (1989) 8:15-28), where X is Lys, Asp, Val or Asn. Such proteins include, among others, leukotoxins derived from *P. haemolytica* and *Actinobacillus pleuropneumoniae*, as well as *E. coli* alpha hemolysin (Strathdee et al., *Infect. Immun.* (1987) 55:3233-3236; Lo, *Can. J. Vet. Res.* (1990) 54:S33-S35; Welch, *Mol. Microbiol.* (1991) 5:521-528). This family of toxins is known as the "RTX" family of toxins (Lo, *Can. J. Vet. Res.* (1990) 54:S33-S35). In addition, the term "RTX toxin" refers to a member of the RTX family which is chemically synthesized, isolated from an organism expressing the same, or recombinantly produced. Furthermore, the term intends an immunogenic protein having an amino acid sequence substantially homologous to a contiguous amino acid sequence found in the particular native RTX molecule. Thus, the term includes both full-length and partial sequences, as well as analogues. Although native full-length RTX toxins display cytotoxic activity, the term "RTX toxin" also intends molecules which remain immunogenic yet lack the cytotoxic character of native molecules. In the chimeras produced according to the present invention, a selected RTX polypeptide sequence imparts enhanced immunogenicity to a fused prion peptide.

The term "leukotoxin polypeptide" or "LKT polypeptide" intends an RTX toxin derived from *P. haemolytica, Actinobacillus pleuropneumoniae*, among others, as defined above. The nucleotide sequences and corresponding amino acid sequences for several leukotoxins are known. See, e.g., U.S. Pat. Nos. 4,957,739 and 5,055,400; Lo et al., *Infect. Immun.* (1985) 50:667-67; Lo et al., *Infect. Immun.* (1987) 55:1987-1996; Strathdee et al., *Infect. Immun.* (1987) 55:3233-3236; Highlander et al., *DNA* (1989) 8:15-28; Welch, *Mol. Microbiol.* (1991) 5:521-528. A selected leukotoxin polypeptide sequence imparts enhanced immunogenicity to a fused prion peptide.

A prion peptide that is linked to a carrier displays "enhanced immunogenicity" when it possesses a greater capacity to elicit an immune response than the corresponding prion peptide alone. Such enhanced immunogenicity can be determined by administering the particular prion peptide/carrier complex and prion peptide controls to animals and comparing antibody titers against the two using standard assays such as radioimmunoassays and ELISAs, well known in the art.

"Substantially purified" generally refers to isolation of a substance (compound, polynucleotide, protein, polypeptide, polypeptide composition) such that the substance comprises the majority percent of the sample in which it resides. Typically in a sample, a substantially purified component comprises 50%, preferably 80%-85%, more preferably 90-95% of the sample. Techniques for purifying polynucleotides and polypeptides of interest are well-known in the art and include, for example, ion-exchange chromatography, affinity chromatography and sedimentation according to density.

By "isolated" is meant, when referring to a polypeptide, that the indicated molecule is separate and discrete from the whole organism with which the molecule is found in nature or is present in the substantial absence of other biological macro-molecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

An "antibody" intends a molecule that "recognizes," i.e., specifically binds to an epitope of interest present in an antigen. By "specifically binds" is meant that the antibody interacts with the epitope in a "lock and key" type of interaction to form a complex between the antigen and antibody, as opposed to non-specific binding that might occur between the antibody and, for instance, components in a mixture that includes the test substance with which the antibody is reacted. Thus, an anti-prion peptide antibody is a molecule that specifically binds to an epitope of the prion peptide in question. The term "antibody" as used herein includes antibodies obtained from both polyclonal and monoclonal preparations, as well as, the following: hybrid (chimeric) antibody molecules (see, for example, Winter et al., *Nature* (1991) 349:293-299; and U.S. Pat. No. 4,816,567); F(ab')2 and F(ab) fragments; Fv molecules (non-covalent heterodimers, see, for example, Inbar et al., *Proc Natl Acad Sci USA* (1972) 69:2659-2662; and Ehrlich et al., *Biochem* (1980) 19:4091-4096); single-chain Fv molecules (sFv) (see, for example, Huston et al., *Proc Natl Acad Sci USA* (1988) 85:5879-5883); dimeric and trimeric antibody fragment constructs; minibodies (see, e.g., Pack et al., *Biochem* (1992) 31:1579-1584; Cumber et al., *J Immunology* (1992) 149B:120-126); humanized antibody molecules (see, for example, Riechmann et al., *Nature* (1988) 332:323-327; Verhoeyan et al., *Science* (1988) 239:1534-1536; and U.K. Patent Publication No. GB 2,276,169, published 21 Sep. 1994); and, any functional fragments obtained from such molecules, wherein such fragments retain immunological binding properties of the parent antibody molecule.

As used herein, the term "monoclonal antibody" refers to an antibody composition having a homogeneous antibody population. The term is not limited regarding the species or source of the antibody, nor is it intended to be limited by the manner in which it is made. The term encompasses whole immunoglobulins as well as fragments such as Fab, $F(ab')_2$, Fv, and other fragments, as well as chimeric and humanized homogeneous antibody populations, that exhibit immunological binding properties of the parent monoclonal antibody molecule.

"Homology" refers to the percent identity between two polynucleotide or two polypeptide moieties. Two nucleic acid, or two polypeptide sequences are "substantially homologous" to each other when the sequences exhibit at least about 50% sequence identity, preferably at least about 75% sequence identity, more preferably at least about 80%-85% sequence identity, more preferably at least about 90% sequence identity, and most preferably at least about 95%-98% sequence identity over a defined length of the molecules. As used herein, substantially homologous also refers to sequences showing complete identity to the specified sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in *Atlas of Protein Sequence and Structure* M. O. Dayhoff ed., 5 Suppl. 3:353-358, National biomedical Research Foundation, Washington, D.C., which adapts the local homology algorithm of Smith and Waterman *Advances in Appl. Math*. 2:482-489, 1981 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one; and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+ PDB+GenBank CDS translations+Swiss protein+Spupdate+ PIR. Details of these programs are readily available.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, supra; *Nucleic Acid Hybridization*, supra.

The terms "polynucleotide," "oligonucleotide," "nucleic acid" and "nucleic acid molecule" are used herein to include a polymeric form of nucleotides of any length, either ribonucleotides or deoxyribonucleotides. This term refers only to the primary structure of the molecule. Thus, the term includes triple-, double- and single-stranded DNA, as well as triple-, double- and single-stranded RNA. It also includes modifications, such as by methylation and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), any other type of polynucleotide which is an N- or C-glycoside of a purine or pyrimidine base, and other polymers containing nonnucleotidic backbones, for example, polyamide (e.g., peptide nucleic acids (PNAs)) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. There is no intended distinction in length between the terms "polynucleotide," "oligonucleotide," "nucleic acid" and "nucleic acid molecule," and these terms will be used interchangeably. Thus, these terms include, for example, 3'-deoxy-2',5'-DNA, oligodeoxyribonucleotide N3' P5' phosphoramidates, 2'-O-alkyl-substituted RNA, double- and single-stranded DNA, as well as double- and single-stranded RNA, DNA:RNA hybrids, and hybrids between PNAs and DNA or RNA, and also include known types of modifications, for example, labels which are known in the art, methylation, "caps," substitution of one or more of the naturally occurring nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalklyphosphoramidates, aminoalkylphosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide. In particular, DNA is deoxyribonucleic acid.

The term "derived from" is used herein to identify the original source of a molecule but is not meant to limit the method by which the molecule is made which can be, for example, by chemical synthesis or recombinant means.

"Recombinant" as used herein to describe a nucleic acid molecule means a polynucleotide of genomic, cDNA, viral, semisynthetic, or synthetic origin which, by virtue of its origin or manipulation is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

"Recombinant host cells", "host cells," "cells", "cell lines," "cell cultures", and other such terms denoting microorganisms or higher eukaryotic cell lines cultured as unicellular entities refer to cells which can be, or have been, used as recipients for recombinant vector or other transferred DNA, and include the original progeny of the original cell which has been transfected.

A "coding sequence" or a sequence which "encodes" a selected polypeptide, is a nucleic acid molecule which is transcribed (in the case of DNA) and translated (in the case of mRNA) into a polypeptide in vivo when placed under the control of appropriate regulatory sequences (or "control elements"). The boundaries of the coding sequence can be determined by a start codon at the 5' (amino) terminus and a translation stop codon at the 3' (carboxy) terminus. A coding sequence can include, but is not limited to, cDNA from viral, procaryotic or eucaryotic mRNA, genomic DNA sequences from viral or procaryotic DNA, and even synthetic DNA sequences. A transcription termination sequence may be located 3' to the coding sequence.

Typical "control elements," include, but are not limited to, transcription promoters, transcription enhancer elements, transcription termination signals, polyadenylation sequences (located 3' to the translation stop codon), sequences for optimization of initiation of translation (located 5' to the coding sequence), and translation termination sequences. "Operably linked" refers to an arrangement of elements wherein the components so described are configured so as to perform their usual function. Thus, a given promoter operably linked to a coding sequence is capable of effecting the expression of the coding sequence when the proper enzymes are present. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered "operably linked" to the coding sequence.

"Encoded by" refers to a nucleic acid sequence which codes for a polypeptide sequence, wherein the polypeptide sequence or a portion thereof contains an amino acid sequence of at least 3 to 5 amino acids, more preferably at least 8 to 10 amino acids, and even more preferably at least 15 to 20 or more amino acids from a polypeptide encoded by the nucleic acid sequence.

"Expression cassette" or "expression construct" refers to an assembly which is capable of directing the expression of the sequence(s) or gene(s) of interest. An expression cassette generally includes control elements, as described above, such as a promoter which is operably linked to (so as to direct transcription of) the sequence(s) or gene(s) of interest, and often includes a polyadenylation sequence as well. Within certain embodiments of the invention, the expression cassette described herein may be contained within a plasmid construct. In addition to the components of the expression cassette, the plasmid construct may also include, one or more selectable markers, a signal which allows the plasmid construct to exist as single-stranded DNA (e.g., a M13 origin of replication), at least one multiple cloning site, and a "mammalian" origin of replication (e.g., a SV40 or adenovirus origin of replication).

The term "transfection" is used to refer to the uptake of foreign DNA by a cell. A cell has been "transfected" when exogenous DNA has been introduced inside the cell membrane. A number of transfection techniques are generally known in the art. See, e.g., Graham et al. (1973) *Virology*, 52:456, Sambrook et al. (1989) *Molecular Cloning, a laboratory manual*, Cold Spring Harbor Laboratories, New York, Davis et al. (1986) *Basic Methods in Molecular Biology*, Elsevier, and Chu et al. (1981) *Gene* 13:197. Such techniques can be used to introduce one or more exogenous DNA moieties into suitable host cells. The term refers to both stable and transient uptake of the genetic material, and includes uptake of peptide- or antibody-linked DNAs.

A "vector" is capable of transferring nucleic acid sequences to target cells (e.g., viral vectors, non-viral vectors, particulate carriers, and liposomes). Typically, "vector construct," "expression vector," and "gene transfer vector," mean any nucleic acid construct capable of directing the expression of a nucleic acid of interest and which can transfer nucleic acid sequences to target cells. Thus, the term includes cloning and expression vehicles, as well as viral vectors.

"Gene transfer" or "gene delivery" refers to methods or systems for reliably inserting DNA or RNA of interest into a host cell. Such methods can result in transient expression of non-integrated transferred DNA, extrachromosomal replication and expression of transferred replicons (e.g., episomes), or integration of transferred genetic material into the genomic DNA of host cells. Gene delivery expression vectors include, but are not limited to, vectors derived from bacterial plasmid vectors, viral vectors, non-viral vectors, alphaviruses, pox viruses and vaccinia viruses. When used for immunization, such gene delivery expression vectors may be referred to as vaccines or vaccine vectors.

As used herein, a "biological sample" refers to a sample of tissue or fluid isolated from a subject, including but not limited to, for example, blood, plasma, serum, fecal matter, urine, bone marrow, bile, spinal fluid, lymph fluid, samples of the skin, external secretions of the skin, respiratory, intestinal, and genitourinary tracts, tears, saliva, milk, blood cells, organs, biopsies and also samples of in vitro cell culture constituents including but not limited to conditioned media resulting from the growth of cells and tissues in culture medium, e.g., recombinant cells, and cell components.

By "vertebrate subject" is meant any member of the subphylum chordata, including, without limitation, humans and other primates, including non-human primates such as chimpanzees and other apes and monkey species; farm animals such as cattle, sheep, pigs, goats and horses; domestic mammals such as dogs and cats; non-domestic animals such as elk, deer, mink and feral cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered.

By "therapeutically effective amount" in the context of the immunogenic compositions is meant an amount of an immunogen (e.g., a prion peptide) which will induce an immunological response, either for antibody production or for treatment or prevention of infection.

For purposes of the present invention, an "effective amount" of a carrier will be that amount which enhances an immunological response to a prion peptide.

As used herein, "treatment" refers to any of (i) the prevention of infection or reinfection, as in a traditional vaccine, or (ii) the reduction or elimination of symptoms from an infected individual. Treatment may be effected prophylactically (prior to infection) or therapeutically (following infection).

2. Modes of Carrying Out the Invention

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

Prion isoform conversion occurs at the cell surface or a compartment close to the cell surface (Caughey et al., *J. Biol. Chem.* (1991) 27:18217-23; Borchelt et al., *J. Cell Biol.* (1990) 110:743-52) which ensures that antibodies are able to interfere in this process. Thus, immunoprophylaxis can be used to prevent the infection of animals exposed to $PrP^{Sc}$. Alternatively, immunoprophylaxis following exposure of animals to feed or an environment contaminated with $PrP^{Sc}$ may effectively reduce the production of $PrP^{Sc}$ or increase its destruction within infected animals. In this way the shedding of PrP$^{Sc}$ by infected animals can be reduced or eliminated and the cycle of disease transmission can be broken.

The present invention thus provides immunological compositions and methods for treating and/or preventing prion disease. The invention is based on the discovery of YML and RL DSEs which are uniquely exposed upon misfolding. These DSEs can be used in vaccine compositions using both univalent and multivalent vaccination strategies. The YML and RL epitopes induce strong PrP$^{Sc}$-specific serum and mucosal antibody responses and retain their properties of immunogenicity, specificity, and safety when delivered individually. When administered in combination, antibodies were successfully generated against each immunizing DSE. Thus, the peptides, polynucleotides and/or antibodies described herein are useful in compositions and methods for treating and preventing prion diseases. Immunization can be achieved by any of the methods known in the art including, but not limited to, use of peptide vaccines or DNA immunization. Such methods are described in detail below. Moreover, the peptides described herein can be used for detecting the presence of pathogenic prions, for example in a biological sample.

In order to further an understanding of the invention, a more detailed discussion is provided below regarding the prion peptides, production thereof, compositions comprising the same, and methods of using such compositions in the treatment or prevention of prion infection, as well as in the diagnosis of infection.

A. Prion Peptides

The prion peptides of the invention include at least one prion DSE that is exposed only upon misfolding of the normal cellular protein (PrP$^C$) into the infectious conformation (PrP$^{Sc}$). In particular, DSEs are derived from the YML region of β-sheet 1 and from the rigid loop (RL) that links β-sheet 2 to α-helix 2 (see, the first and third bolded regions in FIG. 1). The inventors herein have expanded these sequences to include B cell epitopes. Accordingly, the peptides are expansions and preferably fusions of these regions.

If a YML epitope is desired, the peptide will include YML and additional flanking amino acids from the β-sheet 1 YML region, such as 1, 2, 3, 4, 5, 6, 7, 8, 9, 10 . . . 15 . . . 20 or more flanking amino acids, but less than the full-length of the PrP protein. Similarly, the RL DSEs will typically include QYSN (SEQ ID NO:12) and additional flanking amino acids from the RL region. The expansions can be symmetrical, i.e., equal numbers of flanking amino acids, or asymmetrical, i.e., unequal numbers of flanking amino acids.

Thus, for example, with reference to the bovine sequence in FIG. 1, the YML peptides of the present invention can include sequences corresponding to GYMLGSA (SEQ ID NO:13), GYMLGSAM (SEQ ID NO:14); GYMLGSAMS (SEQ ID NO:15); GYMLGSAMSR (SEQ ID NO:16); GYMLGSAMSRP (SEQ ID NO:17), etc. The foregoing sequences are merely illustrative and prion peptides of the present invention can include additional flanking sequences from the YML region shown in FIG. 1, and/or additional flanking amino acids that are not from the YML region.

The amino acids will be determined in part by the species of interest. Thus, for example, in humans, the peptides above may include GYVLGSAM (SEQ ID NO:44); GYVLGSAMS (SEQ ID NO:45); GYVLGSAMSR (SEQ ID NO:46); GYVLGSAMSRP (SEQ ID NO:47), rather than GYMLGSA (SEQ ID NO:13), GYMLGSAM (SEQ ID NO:14); GYMLGSAMS (SEQ ID NO:15); GYMLG-SAMSR (SEQ ID NO:16); GYMLGSAMSRP (SEQ ID NO:17), respectively. According to the present invention, then, GYVLGSAMSRP (SEQ ID NO:47) is a sequence "corresponding to" GYMLGSAMSRP (SEQ ID NO:17), and the like.

Similarly, with reference to the bovine sequence in FIG. 1, the RL peptides of the present invention can include sequences corresponding to, for example, DQYSNQNNF (SEQ ID NO:18) and VDQYSNQNNF (SEQ ID NO:19). The foregoing sequences are merely illustrative and prion peptides of the present invention can include additional flanking sequences from the RL region shown in FIG. 1 and/or additional flanking amino acids that are not from the RL region.

The amino acids will be determined in part by the species of interest. Thus, for example, in humans, the peptides above may include DEYSNQNNF (SEQ ID NO:20) and MDEYSNQNNF (SEQ ID NO:21) rather than DQYSNQNNF (SEQ ID NO:18) and VDQYSNQNNF (SEQ ID NO:19), respectively. Similarly, in deer, the peptides above may include DQYNNQNTF (SEQ ID NO:22) and VDQYNNQNTF (SEQ ID NO:23) rather than DQYSNQNNF (SEQ ID NO:18) and VDQYSNQNNF (SEQ ID NO:19), and so on. According to the present invention, then, MDEYSNQNNF (SEQ ID NO:21) is a sequence "corresponding to" VDQYSNQNNF (SEQ. ID NO:19), and the like.

These peptides can be used alone or in combination. Additional DSEs can also be used with the above peptides, including, without limitation, peptides derived from the YYR region of the prion PrP protein, and particularly, epitopes derived from the β-strand two YYR region, i.e., the region represented by the second bolded region in FIG. 1. Representative peptides are shown in Table 1 herein and include, without limitation, peptides with SEQ ID NOS:24, 26, 28, 30, 32, 34 and 36. As with those peptides above, these peptides are preferably expansions and fusions of this region. Such peptides are described in detail below and in U.S. Patent Publ. 2009/0280125, incorporated herein by reference in its entirety.

As explained above, the peptides of the invention may include fusions of more than one prion peptide and the fusions may include the peptides present as linear repeats, in the same orientation, i.e., the C-terminal amino acid of the first prion peptide is fused to the N-terminal amino acid of the repeat of the prion peptide, the C-terminal amino acid of this repeat is fused to the N-terminal amino acid of the next repeat, etc. Alternatively, one or more of the repeats can be present in an inverted orientation, i.e., the C-terminal amino acid of the first prion peptide is fused to the C-terminal amino acid of the repeat of the prion peptide, etc.

Additionally, linking amino acids may be present between the prion peptide components of the fusions. Such linkers are generally formed from small hydrophilic amino acid residues that do not tend to coil or form secondary structures. Suitable linkers may for example comprise glycine and/or serine residues. Such residues may also be found at the N- and C-terminus of the molecules.

For example, YML fusions of the present invention may be fusions and repeats of GYMLGSA (SEQ ID NO:13), GYMLGSAM (SEQ ID NO:14); GYMLGSAMS (SEQ ID NO:15); GYMLGSAMSR (SEQ ID NO:16); GYMLG-SAMSRP (SEQ ID NO:17), and the like, and fusions and repeats of peptides corresponding thereto from other species. Such fusions include but are not limited to a fusion of SEQ ID NO:17 with the epitope presentation of $(\rightarrow\leftarrow\leftarrow)_4$, having the sequence GYMLGSAMSRPPRSMASGLMYG-PRSMASGLMYG GYMLGSAMSRPPRSMASGLMYG- PRSMASGLMYGGYMLGSAMSRPPRSMASGLMY
GPRSMASGLMYGGYMLGSAMSRPPRSMASGLMYG-
PRSMASGLMYG (SEQ ID NO:38). Similar fusions of SEQ ID NOS:13, 14, 15 and 16 will also find use herein.

Similarly, RL fusions of the present invention can be fusions and repeats of DQYSNQNNF (SEQ ID NO:18) and VDQYSNQNNF (SEQ ID NO:19), and fusions and repeats of peptides corresponding thereto from other species. Such fusions include but are not limited to a fusion of SEQ ID NO:19 with the epitope presentation of (→←←)$_4$, having the sequence: VDQYSNQNNFFNNQNSYQDVVDQYSN-QNNFFNNQNSYQDVVDQYSNQNNFFNNQ NSYQDV-VDQYSNQNNFFNNQNSYQDV (SEQ ID NO:43). Another illustrative fusion includes a fusion of SEQ ID NO:19 with the epitope presentation of (→←←)$_4$ that includes flanking and linking Gly and Ser amino acid residues (bolded), having the sequence: GSVDQYSNQN-NFFNNQNSYQDVFNNQNSYQDVSGSVDQYSNQN-NFFNNQNSYQDV FNNQNSYQDVGSSVDQYSNQN-NFFNNQNSYQDVFNNQNSYQDVSGSVDQYSNQNNF FNNQNSYQDVFNNQNSYQDVSGS (SEQ ID NO:48).

The above YML and RL fusions can be used alone or in combination. Additional DSEs can also be used in the fusions, including, without limitation, fusions derived from peptides from the YYR region of the prion PrP protein, such as fusions using peptides shown in Table 1. Such fusions include, without limitation, those shown as SEQ ID NOS: 25, 27, 29, 31, 33, 35 and 37 in Table 1.

The prion peptides above are representative and it is to be understood that other fusions will find use in the present invention so long as the fusions are immunogenic, as described above.

The repeats present in the fusions can be derived from the same species or from different species in which prions are present. Moreover, there can be 2 or more repeats, such as 3, 4, 5, 6, 7, 8, 9, 10 . . . 15 . . . 20 . . . 25 or more repeats present.

Thus, the prion peptides may also correspond to a molecule of the general formula prion epitope-X-prion epitope, wherein X is selected from the group consisting of a peptide linkage, an amino acid spacer group and [prion epitope]$_n$, where n is greater than or equal to 1. Spacer sequences can be used between selected prion epitopes in order to confer increased immunogenicity on the subject constructs. Accordingly, a selected spacer sequence may encode a wide variety of moieties of one or more amino acids in length. Selected spacer groups may preferably provide enzyme cleavage sites so that the expressed fusions can be processed by proteolytic enzymes in vivo (by APC's or the like) to yield a number of peptides—each of which contain at least one epitope. Further, spacer groups may be constructed so that the junction region between selected prion epitopes comprises a clearly foreign sequence to the immunized subject, thereby conferring enhanced immunogenicity upon the associated prion epitopes. Additionally, spacer sequences may be constructed so as to provide T-cell antigenicity, such as sequences which encode amphipathic and/ or α-helical peptide sequences which are generally regarded in the art as providing immunogenic helper T-cell epitopes. In this regard, the choice of particular T-cell epitopes to be provided by such spacer sequences may vary depending on the particular vertebrate species to be vaccinated.

The prion peptides can be conjugated with a carrier molecule as discussed more fully below.

B. Prion Peptide Conjugates

In order to enhance immunogenicity of the prion peptides, the peptides may be conjugated with a carrier. By "carrier" is meant any molecule which when associated with an antigen of interest, imparts immunogenicity to the antigen. Examples of suitable carriers include large, slowly metabolized macromolecules such as: proteins; polysaccharides, such as sepharose, agarose, cellulose, cellulose beads and the like; polymeric amino acids such as polyglutamic acid, polylysine, and the like; amino acid copolymers; inactive virus particles or toxins, such as lyssavirus glycoprotein (G) in either chimeric or truncated forms (see, e.g., Desmezieres et al., *J. Gen. Virol.* (1999) 80:2343-2351; and U.S. Pat. Nos. 7,645,455, 7,235,245 incorporated herein by reference in their entireties); bacterial toxins and toxoids such as tetanus toxoid and detoxified mutants of a bacterial ADP-ribosylating toxin such as a cholera toxin (CT), a pertussis toxin (PT), or an *E. coli* heat-labile toxin (LT); serum albumins, keyhole limpet hemocyanin, thyroglobulin, ovalbumin, sperm whale myoglobin, and other proteins well known to those skilled in the art. Other suitable carriers for the antigens of the present invention include VP6 polypeptides of rotaviruses, or functional fragments thereof, as disclosed in U.S. Pat. No. 5,071,651.

For example, as explained above, one such carrier is lyssavirus glycoprotein (G) (also known as rabies virus G protein) and can be used to deliver the prion peptides of the invention. The G protein sequences of a number of lyssavirus isolates are known and described in e.g., U.S. Pat. No. 7,645,455, incorporated herein by reference in its entirety, as well as in, for example, GenBank Accession Nos. AGN94165.1, AGN94453.1, AGN94444.1, AGN94435.1, AGN94452.1, AGN94456.1, AGN94464.1, AAA65972.1, AAA65973.1, AGN94520.1, AFN24509.1, AGN94069.1, AGN94524.1, AGN94522.1, AGN94450.1, AGN94527.1, AGN94449.1, AGN94460, AFN27416.1, AGN94451.1, AGN94091.1, AAA19780.1, AGN94090.1, AGN94521.1, AAA64546.2, AAA65974.1, AFN24507.1, AAA64550.2, AAA64548.2, AAA19785.1, AAA19784.1, AAA64559.2, AFN24515.1, AFN24517.1, AGN94430.1, AGN94092.1, AAA64549.2, AGN94163.1, AGN94143.1, AAA19782.1, AGN94440.1, AAA64552.2, AAA64558.2, AAA64543.2, AGN94442.1, AAA19783.1, AAA19781.1, AGN94433.1. Any of these, as well as the G protein from other isolates, will find use herein.

Additionally, the full-length or portions of the G protein can be used. For example, all or part of the C-terminal transmembrane and cytoplasmic domains can be removed to produce a truncated G protein. The sequence of one such truncated G protein which includes a deletion of the transmembrane and cytoplasmic domains is shown in FIG. 10 (SEQ ID NO:49). The G protein can be chemically conjugated with the prion peptides or the conjugates can be conveniently fused with the G protein carriers using recombinant techniques, well known in the art, as described further below.

The above carriers may be used in their native form or their functional group content may be modified by, for example, succinylation of lysine residues or reaction with Cys-thiolactone. A sulfhydryl group may also be incorporated into the carrier (or antigen) by, for example, reaction of amino functions with 2-iminothiolane or the N-hydroxysuccinimide ester of 3-(4-dithiopyridyl) propionate. Suitable carriers may also be modified to incorporate spacer arms (such as hexamethylene diamine or other bifunctional molecules of similar size) for attachment of peptides.

Prion peptides can also be conjugated with a member of the RTX family of toxins (as described further below), such as a *Pasteurella haemolytica* leukotoxin (LKT) polypeptide. See, e.g., International Publication No. WO 93/08290, published 29 Apr. 1993, as well as U.S. Pat. Nos. 5,238,823, 5,273,889, 5,723,129, 5,837,268, 5,422,110, 5,708,155, 5,969,126, 6,022,960, 6,521,746 and 6,797,272, all incorporated herein by reference in their entireties.

Leukotoxin polypeptide carriers are derived from proteins belonging to the family of molecules characterized by the carboxy-terminus consensus amino acid sequence Gly-Gly-X-Gly-X-Asp (Highlander et al., DNA (1989) 8:15-28), where X is Lys, Asp, Val or Asn. Such proteins include, among others, leukotoxins derived from *P. haemolytica* and *Actinobacillus pleuropneumonias*, as well as *E. coli* alpha hemolysin (Strathdee et al., *Infect. Immun.* (1987) 55:3233-3236; Lo, *Can. J. Vet. Res.* (1990) 54:S33-S35; Welch, *Mol. Microbiol.* (1991) 5:521-528). This family of toxins is known as the "RTX" family of toxins (Lo, *Can. J. Vet. Res.* (1990) 54:S33-S35). The nucleotide sequences and corresponding amino acid sequences for several leukotoxins are known. See, e.g., U.S. Pat. Nos. 4,957,739 and 5,055,400; Lo et al., *Infect. Immun.* (1985) 50:667-67; Lo et al., *Infect. Immun.* (1987) 55:1987-1996; Strathdee et al., *Infect. Immun.* (1987) 55:3233-3236; Highlander et al., *DNA* (1989) 8:15-28; Welch, *Mol. Microbiol.* (1991) 5:521-528. Particular examples of immunogenic leukotoxin polypeptides for use herein include LKT 342, LKT 352, LKT 111, LKT 326 and LKT 101 which are described in greater detail below.

By "LKT 352" is meant a protein which is derived from the lktA gene present in plasmid pAA352 (FIG. 2) and described in U.S. Pat. No. 5,476,657, incorporated herein by reference in its entirety. LKT 352 has an N-terminal truncation of the native leukotoxin sequence and includes amino acids 38-951 of the native molecule. Thus, the gene in plasmid pAA352 encodes a truncated leukotoxin, having 914 amino acids which lacks the cytotoxic portion of the molecule. The nucleotide and amino acid sequences of LKT 352 is shown in FIGS. 3A-3F (SEQ ID NOS:8, 9 and 10).

By "LKT 111" is meant a leukotoxin polypeptide which is derived from the lktA gene present in plasmid pCB111. The plasmid and nucleotide sequence of this gene and the corresponding amino acid sequence are described in U.S. Pat. Nos. 5,723,129 and 5,969,126, incorporated herein by reference in their entireties. The gene encodes a shortened version of leukotoxin which was developed from the recombinant leukotoxin gene present in plasmid pAA352 by removal of an internal DNA fragment of approximately 1300 bp in length. The LKT 111 polypeptide has an estimated molecular weight of 52 kDa (as compared to the 99 kDa LKT 352 polypeptide), retains the ability to act as a carrier molecule, and contains convenient restriction sites for use in producing the fusion proteins of the present invention.

By "LKT 101" is meant a leukotoxin polypeptide which is derived from the lktA gene present in plasmid pAA101. The plasmid and sequence of LKT 101 is described in U.S. Pat. No. 5,476,657 (see FIG. 3 therein), incorporated herein by reference in its entirety. The LKT 101 polypeptide is expressed from a C-terminally truncated form of the lktA gene which contains the 5' end of the gene up to the unique Pst1 restriction endonuclease site. Thus, LKT 101 includes the first 377 amino acids of native, full-length, *P. haemolytica* leukotoxin.

By "LKT 342" is meant a leukotoxin polypeptide which is derived from the lktA gene present in plasmid pAA342, described in U.S. Pat. No. 5,476,657, incorporated herein in its entirety. LKT 342 has an N-terminal and C-terminal truncation of the native leukotoxin sequence and includes amino acids 38-334 of native leukotoxin.

The various LKT molecules described above are representative and other leukotoxin molecules which enhance the immunogenicity of the prion peptides will also find use herein. Moreover, the leukotoxin molecules need not be physically derived from the sequence present in the corresponding plasmids but may be generated in any manner, including for example, by chemical synthesis or recombinant production, as described below.

Additionally, the prion peptides can be fused to either the carboxyl or amino terminals or both of the carrier molecule, or at sites internal to the carrier.

Carriers can be physically conjugated to the prion peptides of interest, using standard coupling reactions. Alternatively, chimeric molecules can be prepared recombinantly for use in the present invention, such as by fusing a gene encoding a suitable polypeptide carrier to one or more copies of a gene, or fragment thereof, encoding for a selected prion peptide.

C. Production of Prion Peptides and Conjugates

The prion peptides described herein and conjugates with carrier molecules, can be prepared in any suitable manner (e.g. recombinant expression, purification from cell culture, chemical synthesis, etc.) and in various forms (e.g. native, mutant, fusions, etc.). Means for preparing such peptides and conjugates are well understood in the art. Peptides and conjugates are preferably prepared in substantially pure form (i.e. substantially free from other host cell or non host cell proteins).

The prion peptides and conjugates thereof can be conveniently synthesized chemically, by any of several techniques that are known to those skilled in the peptide art. In general, these methods employ the sequential addition of one or more amino acids to a growing peptide chain. Normally, either the amino or carboxyl group of the first amino acid is protected by a suitable protecting group. The protected or derivatized amino acid can then be either attached to an inert solid support or utilized in solution by adding the next amino acid in the sequence having the complementary (amino or carboxyl) group suitably protected, under conditions that allow for the formation of an amide linkage. The protecting group is then removed from the newly added amino acid residue and the next amino acid (suitably protected) is then added, and so forth. After the desired amino acids have been linked in the proper sequence, any remaining protecting groups (and any solid support, if solid phase synthesis techniques are used) are removed sequentially or concurrently, to render the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide. See, e.g., J. M. Stewart and J. D. Young, *Solid Phase Peptide Synthesis* (Pierce Chemical Co., Rockford, Ill. 1984) and G. Barany and R. B. Merrifield, *The Peptides: Analysis, Synthesis, Biology*, editors E. Gross and J. Meienhofer, Vol. 2, (Academic Press, New York, 1980), pp. 3-254, for solid phase peptide synthesis techniques; and M. Bodansky, *Principles of Peptide Synthesis*, (Springer-Verlag, Berlin 1984) and E. Gross and J. Meienhofer, Eds., *The Peptides: Analysis, Synthesis, Biology*, Vol. 1, for classical solution synthesis.

Typical protecting groups include t-butyloxycarbonyl (Boc), 9-fluorenylmethoxycarbonyl (Fmoc) benzyloxycarbonyl (Cbz); p-toluenesulfonyl (Tx); 2,4-dinitrophenyl; benzyl (Bzl); biphenylisopropyloxycarboxy-carbonyl, t-amyloxycarbonyl, isobornyloxycarbonyl, o-bromobenzyloxycarbonyl, cyclohexyl, isopropyl, acetyl, o-nitrophenylsulfonyl and the like. Typical solid supports are cross-linked polymeric supports. These can include divinylbenzene cross-linked-styrene-based polymers, for example, divinylbenzene-hydroxymethylstyrene copolymers, divinylbenzene-chloromethylstyrene copolymers and divinylbenzene-benzhydrylaminopolystyrene copolymers.

The peptides of the present invention can also be chemically prepared by other methods such as by the method of simultaneous multiple peptide synthesis. See, e.g., Houghten *Proc. Natl. Acad. Sci. USA* (1985) 82:5131-5135; U.S. Pat. No. 4,631,211.

Alternatively, the above-described prion peptides and conjugates can be produced recombinantly. Once coding sequences for the desired proteins have been isolated or synthesized, they can be cloned into any suitable vector or replicon for expression. Numerous cloning vectors are known to those of skill in the art, and the selection of an appropriate cloning vector is a matter of choice. A variety of bacterial, yeast, plant, mammalian and insect expression systems are available in the art and any such expression system can be used. Optionally, a polynucleotide encoding these proteins can be translated in a cell-free translation system. Such methods are well known in the art.

Examples of recombinant DNA vectors for cloning and host cells which they can transform include the bacteriophage λ, (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (*Bacillus*), pIJ61 (*Streptomyces*), pUC6 (*Streptomyces*), YIp5 (*Saccharomyces*), YCp19 (*Saccharomyces*) and bovine papilloma virus (mammalian cells). See, generally, DNA Cloning: Vols. I & II, supra; Sambrook et al., supra; B. Perbal, supra.

Insect cell expression systems, such as baculovirus systems, can also be used and are known to those of skill in the art and described in, e.g., Summers and Smith, Texas Agricultural Experiment Station Bulletin No. 1555 (1987). Materials and methods for baculovirus/insect cell expression systems are commercially available in kit form from, inter alia, Invitrogen, San Diego Calif. ("MaxBac" kit).

Plant expression systems can also be used to produce the immunogenic proteins. Generally, such systems use virus-based vectors to transfect plant cells with heterologous genes. For a description of such systems see, e.g., Porta et al., Mol. Biotech. (1996) 5:209-221; and Hackiand et al., Arch. Virol. (1994) 139:1-22.

Viral systems, such as a vaccinia based infection/transfection system, as described in Tomei et al., J. Virol. (1993) 67:4017-4026 and Selby et al., J. Gen. Virol. (1993) 74:1103-1113, will also find use with the present invention. In this system, cells are first transfected in vitro with a vaccinia virus recombinant that encodes the bacteriophage T7 RNA polymerase. This polymerase displays exquisite specificity in that it only transcribes templates bearing T7 promoters. Following infection, cells are transfected with the DNA of interest, driven by a T7 promoter. The polymerase expressed in the cytoplasm from the vaccinia virus recombinant transcribes the transfected DNA into RNA which is then translated into protein by the host translational machinery. The method provides for high level, transient, cytoplasmic production of large quantities of RNA and its translation product(s).

The coding sequence can be placed under the control of a promoter, ribosome binding site (for bacterial expression) and, optionally, an operator (collectively referred to herein as "control" elements), so that the DNA sequence encoding the desired immunogenic peptide is transcribed into RNA in the host cell transformed by a vector containing this expression construction. The coding sequence may or may not contain a signal peptide or leader sequence. Leader sequences can be removed by the host in post-translational processing. See, e.g., U.S. Pat. Nos. 4,431,739; 4,425,437; 4,338,397.

Other regulatory sequences may also be desirable which allow for regulation of expression of the peptide sequences relative to the growth of the host cell. Such regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

The control sequences and other regulatory sequences may be ligated to the coding sequence prior to insertion into a vector. Alternatively, the coding sequence can be cloned directly into an expression vector which already contains the control sequences and an appropriate restriction site.

In some cases it may be necessary to modify the coding sequence so that it may be attached to the control sequences with the appropriate orientation; i.e., to maintain the proper reading frame. It may also be desirable to produce mutants or analogs of the immunogenic peptides. Mutants or analogs may be prepared by the deletion of a portion of the sequence encoding the peptide, by insertion of a sequence, and/or by substitution of one or more nucleotides within the sequence. Techniques for modifying nucleotide sequences, such as site-directed mutagenesis, are well known to those skilled in the art. See, e.g., Sambrook et al., supra; DNA Cloning, Vols. I and II, supra; Nucleic Acid Hybridization, supra.

The expression vector is then used to transform an appropriate host cell. A number of mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human hepatocellular carcinoma cells (e.g., Hep G2), as well as others. Similarly, bacterial hosts such as *E. coli, Bacillus subtilis*, and *Streptococcus* spp., will find use with the present expression constructs. Yeast hosts useful in the present invention include inter alia, *Saccharomyces cerevisiae, Candida albicans, Candida maltosa, Hansenula polymorpha, Kluyveromyces fragilis, Kluyveromyces lactis, Pichia guillerimondii, Pichia pastoris, Schizosaccharomyces pombe* and *Yarrowia lipolytica*. Insect cells for use with baculovirus expression vectors include, inter alia, *Aedes aegypti, Autographa californica, Bombyx mori, Drosophila melanogaster, Spodoptera frugiperda*, and *Trichoplusia ni*.

Depending on the expression system and host selected, the peptides of the present invention are produced by growing host cells transformed by an expression vector described above under conditions whereby the protein of interest is expressed. The selection of the appropriate growth conditions is within the skill of the art. The cells are then disrupted, using chemical, physical or mechanical means, which lyse the cells yet keep the peptides substantially intact. Intracellular proteins can also be obtained by removing components from the cell wall or membrane, e.g., by the use of detergents or organic solvents, such that leakage of the immunogenic polypeptides occurs. Such methods are known to those of skill in the art and are described in, e.g., Protein Purification Applications: A Practical Approach, (E. L. V. Harris and S. Angal, Eds., 1990).

For example, methods of disrupting cells for use with the present invention include but are not limited to: sonication or ultrasonication; agitation; liquid or solid extrusion; heat treatment; freeze-thaw; desiccation; explosive decompression; osmotic shock; treatment with lytic enzymes including proteases such as trypsin, neuraminidase and lysozyme; alkali treatment; and the use of detergents and solvents such as bile salts, sodium dodecylsulphate, NP40 and CHAPS. The particular technique used to disrupt the cells is largely a matter of choice and will depend on the cell type in which the polypeptide is expressed, culture conditions and any pre-treatment used.

Following disruption of the cells, cellular debris is removed, generally by centrifugation, and the intracellularly produced peptide is further purified, using standard purification techniques such as but not limited to, column chromatography, ion-exchange chromatography, size-exclusion chromatography, electrophoresis, HPLC, immunoadsorbent techniques, affinity chromatography, immunoprecipitation, and the like.

For example, one method for obtaining the intracellular peptide of the present invention involves affinity purification, such as by immunoaffinity chromatography using specific antibodies. The choice of a suitable affinity resin is within the skill in the art. After affinity purification, the peptide can be further purified using conventional techniques well known in the art, such as by any of the techniques described above.

D. Prion Peptide Antibodies

The prion peptides of the present invention can be used to produce antibodies for therapeutic, diagnostic and purification purposes. These antibodies may be polyclonal or monoclonal antibody preparations, monospecific antisera, human antibodies, or may be hybrid or chimeric antibodies, such as humanized antibodies, altered antibodies, F(ab')$_2$ fragments, F(ab) fragments, Fv fragments, single-domain antibodies, dimeric or trimeric antibody fragment constructs, minibodies, or functional fragments thereof which bind to the antigen in question. Antibodies are produced using techniques well known to those of skill in the art and disclosed in, for example, U.S. Pat. Nos. 4,011,308; 4,722,890; 4,016,043; 3,876,504; 3,770,380; and 4,372,745.

For example, the prion peptides can be used to produce prion-specific polyclonal and monoclonal antibodies for use in diagnostic and detection assays, for purification and for use as therapeutics, such as for passive immunization. Such polyclonal and monoclonal antibodies specifically bind to the prion peptides in question. In particular, the prion peptides can be used to produce polyclonal antibodies by administering the peptide to a mammal, such as a mouse, a rat, a rabbit, a goat, or a horse. Serum from the immunized animal is collected and the antibodies are purified from the plasma by, for example, precipitation with ammonium sulfate, followed by chromatography, preferably affinity chromatography. Techniques for producing and processing polyclonal antisera are known in the art.

Mouse and/or rabbit monoclonal antibodies directed against epitopes present in the cell surface antigen can also be readily produced. In order to produce such monoclonal antibodies, the mammal of interest, such as a rabbit or mouse, is immunized, such as by mixing or emulsifying the antigen in saline, preferably in an adjuvant such as Freund's complete adjuvant ("FCA"), and injecting the mixture or emulsion parenterally (generally subcutaneously or intramuscularly). The animal is generally boosted 2-6 weeks later with one or more injections of the antigen in saline, preferably using Freund's incomplete adjuvant ("FIA").

Antibodies may also be generated by in vitro immunization, using methods known in the art. See, e.g., James et al., *J. Immunol. Meth.* (1987) 100:5-40.

Polyclonal antisera is then obtained from the immunized animal. However, rather than bleeding the animal to extract serum, the spleen (and optionally several large lymph nodes) is removed and dissociated into single cells. If desired, the spleen cells (splenocytes) may be screened (after removal of nonspecifically adherent cells) by applying a cell suspension to a plate or well coated with the antigen. B-cells, expressing membrane-bound immunoglobulin specific for the antigen, will bind to the plate, and are not rinsed away with the rest of the suspension. Resulting B-cells, or all dissociated splenocytes, are then induced to fuse with cells from an immortalized cell line (also termed a "fusion partner"), to form hybridomas. Typically, the fusion partner includes a property that allows selection of the resulting hybridomas using specific media. For example, fusion partners can be hypoxanthine/aminopterin/thymidine (HAT)-sensitive.

If rabbit-rabbit hybridomas are desired, the immortalized cell line will be from a rabbit. Such rabbit-derived fusion partners are known in the art and include, for example, cells of lymphoid origin, such as cells from a rabbit plasmacytoma as described in Spieker-Polet et al., *Proc. Natl. Acad. Sci. USA* (1995) 92:9348-9352 and U.S. Pat. No. 5,675,063, or the TP-3 fusion partner described in U.S. Pat. No. 4,859,595, incorporated herein by reference in their entireties. If a rabbit-mouse hybridoma or a rat-mouse or mouse-mouse hybridoma, or the like, is desired, the mouse fusion partner will be derived from an immortalized cell line from a mouse, such as a cell of lymphoid origin, typically from a mouse myeloma cell line. A number of such cell lines are known in the art and are available from the ATCC.

Fusion is accomplished using techniques well known in the art. Chemicals that promote fusion are commonly referred to as fusogens. These agents are extremely hydrophilic and facilitate membrane contact. One particularly preferred method of cell fusion uses polyethylene glycol (PEG). Another method of cell fusion is electrofusion. In this method, cells are exposed to a predetermined electrical discharge that alters the cell membrane potential. Additional methods for cell fusion include bridged-fusion methods. In this method, the antigen is biotinylated and the fusion partner is avidinylated. When the cells are added together, an antigen-reactive B cell-antigen-biotin-avidin-fusion partner bridge is formed. This permits the specific fusion of an antigen-reactive cell with an immortalizing cell. The method may additionally employ chemical or electrical means to facilitate cell fusion.

Following fusion, the cells are cultured in a selective medium (e.g., HAT medium). In order to enhance antibody secretion, an agent that has secretory stimulating effects can optionally be used, such as IL-6. See, e.g., Liguori et al., *Hybridoma* (2001) 20:189-198. The resulting hybridomas can be plated by limiting dilution, and are assayed for the production of antibodies which bind specifically to the immunizing antigen (and which do not bind to unrelated antigens). The selected monoclonal antibody-secreting hybridomas are then cultured either in vitro (e.g., in tissue culture bottles or hollow fiber reactors), or in vivo (e.g., as ascites in mice). For example, hybridomas producing prion peptide-specific antibodies can be identified using RIA or ELISA and isolated by cloning in semi-solid agar or by limiting dilution. Clones producing the desired antibodies can be isolated by another round of screening.

An alternative technique for generating the monoclonal antibodies of the present invention is the selected lymphocyte antibody method (SLAM). This method involves identifying a single lymphocyte that is producing an antibody with the desired specificity or function within a large population of lymphoid cells. The genetic information that encodes the specificity of the antibody (i.e., the immunoglobulin $V_H$ and $V_L$ DNA) is then rescued and cloned. See, e.g., Babcook et al., *Proc. Natl. Acad. Sci. USA* (1996) 93:7843-7848, for a description of this method.

For further descriptions of rabbit monoclonal antibodies and methods of making the same from rabbit-rabbit and rabbit-mouse fusions, see, e.g., U.S. Pat. No. 5,675,063 (rabbit-rabbit); U.S. Pat. No. 4,859,595 (rabbit-rabbit); U.S. Pat. No. 5,472,868 (rabbit-mouse); and U.S. Pat. No. 4,977,081 (rabbit-mouse). For a description of the production of conventional mouse monoclonal antibodies, see, e.g., Kohler and Milstein, *Nature* (1975) 256:495-497.

It may be desirable to provide chimeric antibodies. By "chimeric antibodies" is intended antibodies that are preferably derived using recombinant techniques and which comprise both human (including immunologically "related" species, e.g., chimpanzee) and non-human components. Such antibodies are also termed "humanized antibodies." Preferably, humanized antibodies contain minimal sequence derived from non-human immunoglobulin sequences. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. See, for example, U.S. Pat. Nos. 5,225,539; 5,585,089; 5,693,761; 5,693,762; 5,859,205. In some instances, framework residues of the human immunoglobulin are replaced by corresponding non-human residues (see, for example, U.S. Pat. Nos. 5,585,089; 5,693,761; 5,693,762). Furthermore, humanized antibodies may comprise residues that are not found in the recipient antibody or in the donor antibody. These modifications are made to further refine antibody performance (e.g., to obtain desired affinity). In general, the humanized antibody will comprise substantially all of at least one, and typically two, variable domains, in which all or substantially all of the hypervariable regions correspond to those of a non-human immunoglobulin and all or substantially all of the framework regions are those of a human immunoglobulin sequence. The humanized antibody optionally also will comprise at least a portion of an immunoglobulin constant region (Fc), typically that of a human immunoglobulin. For further details see Jones et al., *Nature* (1986) 331:522-525; Riechmann et al., *Nature* (1988) 332: 323-329; and Presta, *Curr. Op. Struct. Biol.* (1992) 2:593-596.

Also encompassed are xenogeneic or modified antibodies produced in a non-human mammalian host, more particularly a transgenic mouse, characterized by inactivated endogenous immunoglobulin (Ig) loci. In such transgenic animals, competent endogenous genes for the expression of light and heavy subunits of host immunoglobulins are rendered non-functional and substituted with the analogous human immunoglobulin loci. These transgenic animals produce human antibodies in the substantial absence of light or heavy host immunoglobulin subunits. See, for example, U.S. Pat. No. 5,939,598.

Antibody fragments which retain the ability to recognize the peptide of interest, will also find use herein. A number of antibody fragments are known in the art which comprise antigen-binding sites capable of exhibiting immunological binding properties of an intact antibody molecule. For example, functional antibody fragments can be produced by cleaving a constant region, not responsible for antigen binding, from the antibody molecule, using e.g., pepsin, to produce F(ab')2 fragments. These fragments will contain two antigen binding sites, but lack a portion of the constant region from each of the heavy chains. Similarly, if desired, Fab fragments, comprising a single antigen binding site, can be produced, e.g., by digestion of polyclonal or monoclonal antibodies with papain. Functional fragments, including only the variable regions of the heavy and light chains, can also be produced, using standard techniques such as recombinant production or preferential proteolytic cleavage of immunoglobulin molecules. These fragments are known as FV. See, e.g., Inbar et al., *Proc. Nat. Acad. Sci. USA* (1972) 69:2659-2662; Hochman et al., *Biochem.* (1976) 15:2706-2710; and Ehrlich et al., *Biochem.* (1980) 19:4091-4096.

A phage-display system can be used to expand antibody molecule populations in vitro. Saiki, et al., *Nature* (1986) 324:163; Scharf et al., *Science* (1986) 233:1076; U.S. Pat. Nos. 4,683,195 and 4,683,202; Yang et al., *J Mol Biol.* (1995) 254:392; Barbas, III et al., *Methods: Comp. Meth Enzymol.* (1995) 8:94; Barbas, III et al., *Proc Natl Acad Sci USA* (1991) 88:7978.

Once generated, the phage display library can be used to improve the immunological binding affinity of the Fab molecules using known techniques. See, e.g., Figini et al., *J. Mol. Biol.* (1994) 239:68. The coding sequences for the heavy and light chain portions of the Fab molecules selected from the phage display library can be isolated or synthesized, and cloned into any suitable vector or replicon for expression. Any suitable expression system can be used, including those described above.

Single chain antibodies can also be produced. A single-chain Fv ("sFv" or "scFv") polypeptide is a covalently linked VH-VL heterodimer which is expressed from a gene fusion including VH- and VL-encoding genes linked by a peptide-encoding linker. Huston et al., *Proc. Nat. Acad. Sci. USA* (1988) 85:5879-5883. A number of methods have been described to discern and develop chemical structures (linkers) for converting the naturally aggregated, but chemically separated, light and heavy polypeptide chains from an antibody V region into an sFv molecule which will fold into a three dimensional structure substantially similar to the structure of an antigen-binding site. See, e.g., U.S. Pat. Nos. 5,091,513, 5,132,405 and 4,946,778. The sFv molecules may be produced using methods described in the art. See, e.g., Huston et al., *Proc. Nat. Acad. Sci. USA* (1988) 85:5879-5883; U.S. Pat. Nos. 5,091,513, 5,132,405 and 4,946,778. Design criteria include determining the appropriate length to span the distance between the C-terminus of one chain and the N-terminus of the other, wherein the linker is generally formed from small hydrophilic amino acid residues that do not tend to coil or form secondary structures. Such methods have been described in the art. See, e.g., U.S. Pat. Nos. 5,091,513, 5,132,405 and 4,946,778. Suitable linkers generally comprise polypeptide chains of alternating sets of glycine and serine residues, and may include glutamic acid and lysine residues inserted to enhance solubility.

"Mini-antibodies" or "minibodies" will also find use with the present invention. Minibodies are sFv polypeptide chains which include oligomerization domains at their C-termini, separated from the sFv by a hinge region. Pack et al., *Biochem.* (1992) 31:1579-1584. The oligomerization domain comprises self-associating α-helices, e.g., leucine zippers, that can be further stabilized by additional disulfide bonds. The oligomerization domain is designed to be compatible with vectorial folding across a membrane, a process thought to facilitate in vivo folding of the polypeptide into a functional binding protein. Generally, minibodies are produced using recombinant methods well known in the art. See, e.g., Pack et al., *Biochem.* (1992) 31:1579-1584; Cumber et al., *J. Immunology* (1992) 149B:120-126.

Polynucleotide sequences encoding the antibodies and immunoreactive fragments thereof, described above, are readily obtained using standard techniques, well known in the art, such as those techniques described above with respect to the recombinant production of the prion peptides.

For subjects known to have a prion disease, an anti-prion peptide antibody may have therapeutic benefit and can be used to confer passive immunity to the subject in question. Alternatively, antibodies can be used in diagnostic applications, described further below, as well as for purification of the prion peptides.

E. Compositions

The prion peptides, conjugates thereof, nucleic acids and/or antibodies, can be formulated into compositions for delivery to subjects for either inhibiting infection, or for enhancing an immune response to prion proteins. Compositions of the invention may comprise or be co-administered with additional prion peptides, as well as non-prion antigens or combination of antigens. Methods of preparing such formulations are described in, e.g., *Remington's Pharmaceutical Sciences*, Mack Publishing Company, Easton, Pa., 18 Edition, 1990. Thus, DSEs can be administered alone in univalent vaccines, or together in multivalent vaccines comprising both YML and RL DSEs, YML and YYR DSEs, RL and YYR DSEs, YML, RL and YYR DSEs, etc. Additionally, the individual peptides can be co-administered in separate vaccines at the same or different sites. Moreover, additional prion DSEs can be present in the compositions. The compositions of the present invention can be prepared as injectables, either as liquid solutions or suspensions. Solid forms suitable for solution in or suspension in liquid vehicles prior to injection may also be prepared. The preparation may also be emulsified or the active ingredient encapsulated in liposome vehicles. The active immunogenic ingredient is generally mixed with a compatible pharmaceutical vehicle, such as, for example, water, saline, dextrose, glycerol, ethanol, or the like, and combinations thereof. In addition, if desired, the vehicle may contain minor amounts of auxiliary substances such as wetting or emulsifying agents and pH buffering agents.

If used to modulate an immune response, additional adjuvants which enhance the effectiveness of the composition may also be added to the formulation. Adjuvants may include for example, muramyl dipeptides, pyridine, aluminum hydroxide, dimethyldioctadecyl ammonium bromide (DDA), oils, oil-in-water emulsions, saponins, cytokines, and other substances known in the art.

The peptides may be used in their native form or their functional group content may be modified by, for example, succinylation of lysine residues or reaction with Cys-thiolactone. A sulfhydryl group may also be incorporated by, for example, reaction of amino functions with 2-iminothiolane or the N-hydroxysuccinimide ester of 3-(4-dithiopyridyl propionate.

Furthermore, the peptides and conjugates thereof may be formulated into compositions in either neutral or salt forms. Pharmaceutically acceptable salts include the acid addition salts (formed with the free amino groups of the active polypeptides) and which are formed with inorganic acids such as, for example, hydrochloric or phosphoric acids, or such organic acids as acetic, oxalic, tartaric, mandelic, and the like. Salts formed from free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Injectable formulations will contain a "pharmaceutically effective amount" of the active ingredient, that is, an amount capable of achieving the desired response in a subject to which the composition is administered. In the treatment and prevention of prion disease, for example, a "pharmaceutically effective amount" would preferably be an amount which reduces or ameliorates the symptoms of the disease in question. The exact amount is readily determined by one skilled in the art using standard tests. The prion peptide, conjugate thereof and/or nucleic acid will typically range from about 1% to about 95% (w/w) of the composition, or even higher or lower if appropriate. With the present formulations, 1 μg to 2 mg, such as 100 μg to 1 mg, of active ingredient per ml of injected solution should be adequate to treat or prevent infection when a dose of 1 to 5 ml per subject is administered. If an adjuvant is used to enhance the immune response to co-delivered prion peptides or conjugates thereof, the amount of adjuvant delivered will generally be in the range of 2 ng to 5 mg, more generally 5 ng to 500 ng, for example 10 ng to 250 ng, or any amount within these stated ranges. The quantity to be administered depends on the subject to be treated, the capacity of the subject's immune system to synthesize antibodies, and the degree of protection desired. Effective dosages can be readily established by one of ordinary skill in the art through routine trials establishing dose response curves.

The composition can be administered parenterally, e.g., by intratracheal, intramuscular, subcutaneous, intraperitoneal, intravenous injection, or by delivery directly to the lungs, such as through aerosol administration. The subject is administered at least one dose of the composition. Moreover, the subject may be administered as many doses as is required to bring about the desired biological effect.

Additional formulations which are suitable for other modes of administration include suppositories and, in some cases, aerosol, intranasal, oral formulations, and sustained release formulations. For suppositories, the vehicle composition will include traditional binders and carriers, such as, polyalkaline glycols, or triglycerides. Such suppositories may be formed from mixtures containing the active ingredient in the range of about 0.5% to about 10% (w/w), preferably about 1% to about 2%. Oral vehicles include such normally employed excipients as, for example, pharmaceutical grades of mannitol, lactose, starch, magnesium, stearate, sodium saccharin cellulose, magnesium carbonate, and the like. These oral vaccine compositions may be taken in the form of solutions, suspensions, tablets, pills, capsules, sustained release formulations, or powders, and contain from about 10% to about 95% of the active ingredient, preferably about 25% to about 70%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

Controlled or sustained release formulations are made by incorporating the protein into carriers or vehicles such as liposomes, nonresorbable impermeable polymers such as ethylenevinyl acetate copolymers and HYTREL copolymers, swellable polymers such as hydrogels, resorbable polymers such as collagen and certain polyacids or polyesters such as those used to make resorbable sutures, polyphosphazenes, alginate, microparticles, gelatin nanospheres, chitosan nanoparticles, and the like. The prion peptide, conjugates and/or nucleic acids described herein can also be delivered using implanted mini-pumps, well known in the art.

Prime-boost methods can be employed where one or more compositions are delivered in a "priming" step and, subsequently, one or more compositions are delivered in a "boosting" step. In certain embodiments, priming and boosting with one or more compositions described herein is followed by additional boosting. The compositions delivered can include the same prion peptides or conjugates thereof, or different prion peptides or conjugates thereof, given in any order and via any administration route. Similarly, if multiple DSEs are used, these can be administered either in a single composition or in separate compositions.

The prion peptides can also be administered via a carrier virus which expresses the same. Carrier viruses which will find use herein include, but are not limited to, the vaccinia and other pox viruses, adenovirus, and herpes virus. By way of example, vaccinia virus recombinants expressing the proteins can be constructed as follows. The DNA encoding a particular protein is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the desired immunogen into the viral genome. The resulting TK-recombinant can be selected by culturing the cells in the presence of 5-bromodeoxyuridine and picking viral plaques resistant thereto.

F. Nucleic Acid-Based Immunization Methods

Generally, nucleic acid-based vaccines for use with the present invention will include relevant regions encoding a prion peptide, with suitable control sequences and, optionally, ancillary therapeutic nucleotide sequences. The nucleic acid molecules are prepared in the form of vectors which include the necessary elements to direct transcription and translation in a recipient cell, as described above.

In order to augment an immune response in an immunized subject, the nucleic acid molecules can be administered in conjunction with ancillary substances, such as pharmacological agents, adjuvants, or in conjunction with delivery of vectors encoding biological response modifiers such as cytokines and the like.

Once prepared, the nucleic acid vaccine compositions can be delivered to the subject using known methods. In this regard, various techniques for immunization with antigen-encoding DNAs have been described. See, e.g., U.S. Pat. No. 5,589,466 to Feigner et al.; Tang et al. (1992) *Nature* 358:152; Davis et al. (1993) *Hum. Molec. Genet.* 2:1847; Ulmer et al. (1993) *Science* 258:1745; Wang et al. (1993) *Proc. Natl. Acad. Sci. USA* 90:4156; Eisenbraun et al. (1993) *DNA Cell Biol.* 12:791; Fynan et al. (1993) *Proc. Natl. Acad. Sci. USA* 90:12476; Fuller et al. (1994) *AIDS Res. Human Retrovir.* 10:1433; and Raz et al. (1994) *Proc. Natl. Acad. Sci. USA* 91:9519. General methods for delivering nucleic acid molecules to cells in vitro, for the subsequent reintroduction into the host, can also be used, such as liposome-mediated gene transfer. See, e.g., Hazinski et al. (1991) *Am. J. Respir. Cell Mol. Biol.* 4:206-209; Brigham et al. (1989) *Am. J. Med. Sci.* 298:278-281; Canonico et al. (1991) *Clin. Res.* 39:219 A; and Nabel et al. (1990) *Science* 249:1285-1288. Thus, the nucleic acid vaccine compositions can be delivered in either liquid or particulate form using a variety of known techniques. Typical vaccine compositions are described above.

G. Tests to Determine the Efficacy of an Immune Response

One way of assessing efficacy of therapeutic treatment involves monitoring infection after administration of a composition of the invention. One way of assessing efficacy of prophylactic treatment involves monitoring immune responses against the prion peptides in the compositions of the invention after administration of the composition.

Another way of assessing the immunogenicity of the component proteins of the immunogenic compositions of the present invention is to express the proteins recombinantly and to screen the subject's sera by immunoblot. A positive reaction between the protein and the serum indicates that the subject has previously mounted an immune response to the protein in question—that is, the protein is an immunogen. This method may also be used to identify immunodominant proteins and/or epitopes.

Another way of checking efficacy of therapeutic treatment involves monitoring infection after administration of the compositions of the invention. One way of checking efficacy of prophylactic treatment involves monitoring immune responses both systemically (such as monitoring the level of IgG1 and IgG2a production) and mucosally (such as monitoring the level of IgA production) against the antigens in the compositions of the invention after administration of the composition. Typically, serum-specific antibody responses are determined post-immunization but pre-challenge whereas mucosal specific antibody body responses are determined post-immunization and post-challenge. The immunogenic compositions of the present invention can be evaluated in in vitro and in vivo animal models prior to host administration.

The efficacy of immunogenic compositions of the invention can also be determined in vivo by challenging animal models of infection with the immunogenic compositions. The immunogenic compositions may or may not be derived from the same strains as the challenge strains. Preferably the immunogenic compositions are derivable from the same strains as the challenge strains.

The immune response may be one or both of a TH1 immune response and a TH2 response. The immune response may be an improved or an enhanced or an altered immune response. The immune response may be one or both of a systemic and a mucosal immune response. Preferably the immune response is an enhanced systemic and/or mucosal response.

An enhanced systemic and/or mucosal immunity is reflected in an enhanced TH1 and/or TH2 immune response. Preferably, the enhanced immune response includes an increase in the production of IgG1 and/or IgG2a and/or IgA. Preferably the mucosal immune response is a TH2 immune response. Preferably, the mucosal immune response includes an increase in the production of IgA.

Activated TH2 cells enhance antibody production and are therefore of value in responding to extracellular infections. Activated TH2 cells may secrete one or more of IL-4, IL-5, IL-6, and IL-10. A TH2 immune response may result in the production of IgG1, IgE, IgA and memory B cells for future protection.

A TH2 immune response may include one or more of an increase in one or more of the cytokines associated with a TH2 immune response (such as IL-4, IL-5, IL-6 and IL-10), or an increase in the production of IgG1, IgE, IgA and memory B cells. Preferably, the enhanced TH2 immune response will include an increase in IgG1 production.

A TH1 immune response may include one or more of an increase in CTLs, an increase in one or more of the cytokines associated with a TH1 immune response (such as IL-2, IFNγ, and TNFβ), an increase in activated macrophages, an increase in NK activity, or an increase in the production of IgG2a. Preferably, the enhanced TH1 immune response will include an increase in IgG2a production.

Immunogenic compositions of the invention, in particular, immunogenic composition comprising one or more antigens of the present invention may be used either alone or in combination with other antigens optionally with an immunoregulatory agent capable of eliciting a Th1 and/or Th2 response.

The immunogenic compositions of the invention will preferably elicit both a cell mediated immune response as well as a humoral immune response in order to effectively address an infection. This immune response will preferably induce long lasting (e.g., neutralizing) antibodies and a cell mediated immunity that can quickly respond upon exposure to one or more infectious antigens. By way of example, evidence of neutralizing antibodies in patient blood samples is considered as a surrogate parameter for protection.

H. Diagnostic Assays

Antibodies, produced as described above, can be used in vivo, i.e., injected into subjects suspected of having prion disease, for diagnostic or therapeutic uses. The use of antibodies for in vivo diagnosis is well known in the art. The label used will depend on the imaging modality chosen. Radioactive labels such as Indium-111, Technetium-99m, or Iodine-131 can be used for planar scans or single photon emission computed tomography (SPECT). Positron emitting labels such as Fluorine-19 can also be used for positron emission tomography (PET). For MRI, paramagnetic ions such as Gadolinium (III) or Manganese (II) can be used. Localization of the label within the patient allows determination of the presence of the disease.

The antibodies can also be used in standard in vitro immunoassays, to screen biological samples such as blood and/or tissues for the presence or absence of the infectious form of prions, $PrP^{Sc}$. Thus, the antibodies produced as described above, can be used in assays to diagnose prion disease. The antibodies can be used as either the capture component and/or the detection component in the assays, as described further below. Thus, the presence of prion disease can be determined by the presence of $PrP^{Sc}$ antigens and/or anti-prion peptide antibodies.

For example, the presence of $PrP^{Sc}$ antigens can be detected using standard electrophoretic and immunodiagnostic techniques, including immunoassays such as competition, direct reaction, or sandwich type assays. Such assays include, but are not limited to, Western blots; agglutination tests; enzyme-labeled and mediated immunoassays, such as enzyme-linked immunosorbent assays ("ELISAs"); biotin/avidin type assays; radioimmunoassays; immunoelectrophoresis; immunoprecipitation, etc. The reactions generally include revealing labels such as fluorescent, chemiluminescent, radioactive, or enzymatic labels or dye molecules, or other methods for detecting the formation of a complex between the antigens and the antibodies described above.

Assays can also be conducted in solution, such that the antigens and antibodies thereto form complexes under precipitating conditions. The precipitated complexes can then be separated from the test sample, for example, by centrifugation. The reaction mixture can be analyzed to determine the presence or absence of antibody-antigen complexes using any of a number of standard methods, such as those immunodiagnostic methods described above.

I. Kits

The invention also provides kits comprising one or more containers of compositions of the invention. Compositions can be in liquid form or can be lyophilized, as can individual antigens. Suitable containers for the compositions include, for example, bottles, vials, syringes, and test tubes. Containers can be formed from a variety of materials, including glass or plastic. A container may have a sterile access port (for example, the container may be an intravenous solution bag or a vial having a stopper pierceable by a hypodermic injection needle).

The kit can further comprise a second container comprising a pharmaceutically-acceptable buffer, such as phosphate-buffered saline, Ringer's solution, or dextrose solution. It can also contain other materials useful to the end-user, including other pharmaceutically acceptable formulating solutions such as buffers, diluents, filters, needles, and syringes or other delivery device. The kit may further include a third component comprising an adjuvant.

The kit can also comprise a package insert containing written instructions for methods of inducing immunity or for treating infections. The package insert can be an unapproved draft package insert or can be a package insert approved by the Food and Drug Administration (FDA) or other regulatory body.

The invention also provides a delivery device pre-filled with the immunogenic compositions of the invention.

Similarly, antibodies can be provided in kits, with suitable instructions and other necessary reagents, in order to conduct immunoassays as described above. The kit can also contain, depending on the particular immunoassay used, suitable labels and other packaged reagents and materials (i.e. wash buffers and the like). Standard immunoassays, such as those described above, can be conducted using these kits.

3. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Materials and Methods

A. In Silico Epitope Expansion:

Weakly immunogenic DSE sequences were made more immunogenic through the expansion of the core sequence, in the context of $PrP^C$, to include immunogenic B cell epitopes. This was conducted through the in silico creation of a comprehensive panel of all the theoretical expansions around the DSE core sequence of interest. This panel encompassed all possible combinations of expansions for up to ten residues in both the N and C terminal directions. This panel of sequences was then evaluated using the approach of Larson et al., which is publicly available at tools.immuneepitope.org/main/, for prediction of B cell epitopes which would be anticipated to increase immunogenicity (Larson et al., *Immunome Research* (2006) 2:2). Notably, in the context of the final recombinant carrier protein these epitopes are in a forward-back-back presentation that is repeated four times (Hedlin et al., *Vaccine* (2010) 28:981-988). A double repeat within the final immunizing epitope presentation pattern was considered in the analysis for B cell epitopes. The vaccine epitope sequences exhibited high predicted immunogenicity while adhering to conformational specificity restrictions. In addition, the expansions were designed such that the resulting epitope would exhibit a high degree of conservation across target species of interest including deer, elk, sheep, cattle, and mice.

B. Construction and Purification of Lkt Constructs:

Genes expressing the desired prion DSEs were synthesized by Genscript (Piscataway, N.J.) and provided in the pUC57 plasmid. The appropriate fragments were removed via restriction digestion with BamHI and NcoI (New England BioLabs, Ipswich, Mass.) and ligated into a modified version plasmid pAA352 as described in U.S. Pat. Nos. 5,476,657; 5,422,110; 5,723,129 and 5,837,268, incorporated herein by reference in their entireties. Plasmid pAA352 is depicted in FIG. 2. The modified plasmid replaced the Ampicillin resistance marker with a Kanamycin marker. These plasmids express LKT 352, the sequence of which is depicted in FIGS. 3A-3F (SEQ ID NOS:8, 9 and 10). LKT 352 is derived from the lktA gene of *Pasteurella haemolytica* leukotoxin and is a truncated leukotoxin molecule, having 914 amino acids and an estimated molecular weight of around 99 kDa, which lacks the cytotoxic portion of the molecule. The DSEs were expressed as C-terminal fusions to the highly immunogenic leukotoxin protein which has been shown to be effective for inducing antibody responses against self-peptides, including GnRH (see, e.g., U.S. Pat. Nos. 6,521,746, 6,022,960, 5,969,126, 5,837,268 and 5,723,129 incorporated herein in their entireties) and prion epitopes (Hedlin et al., *Vaccine* (2010) 28:981-988).

A series of plasmid constructs were created representing different expansions of the DSEs as well as different presentations of the antigens as either linear or inverted repeats. The various constructs are described further below. All plasmids were sequenced to ensure the fidelity of sequence and reading frame.

Chimeric LktA expression vectors were transformed into BL21(DE3) followed by growth and IPTG induction by standard protocols. The recombinant proteins were produced as inclusion bodies and re-solubilized in 4M Guanidine-HCl as described. See, Harland et al., *Can. Vet. J.* (1992) 33:734-741 and U.S. Pat. No. 6,100,066, incorporated herein by reference in its entirety). The isolated protein was determined by denaturing polyacrylamide gel electrophoresis to be approximately 85% pure, which is of sufficient purity for immunization trials.

B. Vaccine Formulation and Delivery:

Mice:

Mice were injected subcutaneously (SC) with 10 µg of leukotoxin recombinant fusion formulated in saline with 30% EMULSIGEN-D (MVP Technologies, Omaha, Nebr.), an adjuvant containing dimethyl dioctadecyl ammonium bromide, for a final injection volume of 100 µl per vaccine dose. Mice, at 5-6 weeks of age, received 3 injections of the vaccine on days 0, 21 and 42. Serum samples were obtained on days 0, 21, 28, 42, 49, and 70.

Sheep:

Sheep of mixed sex and breed (Suffolk and Arcott) were injected SC with 50 µg of Lkt recombinant fusion prepared in PBS (0.188 M $Na_2HPO_4$, 0.012 M $NaH_2PO_4$, 1.8% NaCl, pH 7.8) and 30% EMULSIGEN-D (MVP Technologies, Omaha, Nebr.), for a final injection volume of 1 mL per vaccine dose. Vaccines were administered 3 times at 6-week intervals.

C. Peptide Synthesis:

To detect peptide-specific antibody responses, peptides consisting of a single repeat motif for each DSE sequence were synthesized as previously described (Hedlin et al., *Vaccine* (2010) 28:981-988). The purity and molecular weight of the respective peptides were confirmed by matrix-assisted laser desorption ionization (MALDI)-time of flight mass spectrometry on a PE Biosystems Voyager system 4068 (National Research Council, Plant Biotechnology Institute, Saskatoon, Canada).

D. ELISAs:

The epitope, carrier, and $PrP^C$-specific antibody responses were quantified by ELISA for serum and nasal mucosal samples, as previously described (Hedlin et al., *Vaccine* (2010) 28:981-988). ELISA titres were expressed as the reciprocal of the highest serum dilution resulting in a reading exceeding two standard deviations above the negative control (pre-immune).

E. Statistical Analysis:

The data represents ELISA antibody titres in animals taken over time and did not adhere to a normal distribution. To account for the repeated measures study design, data for each animal were first summed over time. The data sums were then ranked to account for their non-normal distribution and then a one-way ANOVA analysis was performed on the ranked sums. Where appropriate, Tukey's test was used to examine the differences among the groups. P values less than 0.05 were considered significant. All analysis met the assumptions of ANOVA.

F. Immunoprecipitation of $PrP^{Sc}$:

Serum samples from immunized sheep were evaluated for specific interaction with $PrP^{Sc}$ and $PrP^C$. Prior to the immunoprecipitation, immunoglobulin was separated from the serum using column-affinity purification to reduce background. Immunoglobulin conjugated to magnetic beads was used in immunoprecipitation assays with brain homogenates from uninfected and Rocky Mountain Laboratory scrapie (RML)-infected mice as described by (Paramithiotis et al., *Nature Medicine* (2003) 9:893-899).

G. Preparation of Brain Homogenates for PK Digest and Antibody-Induced Misfolding:

Ovine brain homogenates (10% w/v) were prepared in ice-cold lysis buffer (100 mM NaCl, 10 mM EDTA, 0.5% NONIDET P-40, 0.5% sodium deoxycholate, 10 mM Tris-HCl, pH 7.5) using a handheld electric homogenizer and 3 cycles of 30 seconds of homogenization on ice. Lysates were incubated on ice for 30 min with periodic vortexing then centrifuged at 1000 g at 4° C. for 10 min. Supernatants were transferred into sterile 1.5 ml microfuge tubes and stored at −80° C. prior to Proteinase K digests or use in antibody-induced misfolding experiments.

H. Proteinase K Digests:

PK digestion of 50 µl of 10% w/v ovine brain homogenates was carried out with 20 µg/ml of Proteinase K (PK) (Sigma) at 37° C. with shaking for 1 hr. Digested and undigested control samples were analyzed by SDS-PAGE and western blotting to PVDF membrane followed by detection using the primary antibody 6H4 (Prionics, Switzerland), and secondary antibody Alkaline phosphatase conjugated goat anti-mouse (KPL labs, Gaithersburg, Md.). Blots were detected with BCIP/NBT (SIGMA, St. Louis, Mo.) according to the manufacturers suggested protocol.

I. Antibody-Induced Misfolding:

Antibody induced misfolding experiments with ovine brain homogenates were carried out by adding 2 ml of pooled prebleed or 15-week post-vaccination sera from each group to 49 µl of 10% (w/v) brain homogenate, in a sterile 1.5 ml microfuge tube. Serum from an unvaccinated animal was included as a negative control. Homogenates were incubated at 37° C. for 24 hrs with shaking at 200 rpm in an Innova 4900 Multi-tier environmental shaker. After incubation, homogenates were spun at 2,500×g for 1 min to collect all liquid at the bottom of each tube. The reaction mixture was pipetted 5 times prior to removing a 25 µl aliquot for Proteinase K (PK) digestion. PK digestion was carried out with 20 µg/ml of PK as described above but for 1 hr, and digestion was halted with 2 mM PMSF. Undigested samples were incubated the same way with $H_2O$ instead of PK. An equal volume of 2× Laemmli SDS-PAGE loading buffer containing 5% v/v β-mercaptoethanol was added to each digested or undigested homogenate, vortexed to mix, and heated for 5 min at 95° C. Samples were allowed to cool to room temperature, and then centrifuged at 18,000×g for 1 min prior to loading 18 µl into each lane of a 15-well 1.0 mm 12% polyacrylamide SDS Tris-Glycine mini-gel for electrophoresis. Western blotting and detection was carried out as described for Proteinase K digests.

J. Immunohistochemical Staining for $PrP^{Sc}$.

Immunohistochemical staining was conducted at Prairie Diagnostic Services (Saskatoon, SK) using the Benchmark staining platform (Ventana Medical Systems, Tuscon, Ariz.) and an HRP-labelled multimer detection system (BMK Ultraview DAB Paraffin detection kit, Ventana Medical Systems, Tuscon, Ariz.). Heat-induced epitope retrieval consisted of applying CC 1 extended incubation followed by Protease 3 for two minutes (these and other reagents are included in the kit from Ventana Medical Systems Inc.). The Mouse anti-TSE clone F99/97.6.1 primary antibody (VMRD Inc, Pullman, Wash.) was applied for 32 minutes at a dilution of 1:1500.

Example 1

Production of Expanded YYR Epitopes

Epitope β2(2+YYR+9)I, shown in Table 1 below and described in U.S. Patent Publ. 2009/0280125, incorporated herein by reference in its entirety, was used to create a panel of epitope candidates based on systematic truncations from the C-terminus: 2+YYR+8, 2+YYR+7, 2+YYR+6, 2+YYR+5, 2+YYR+4 and 2+YYR+3. A list of the peptide sequences used in this investigation is presented in Table 1. This series of epitopes was created in the context of C-terminal fusions with the recombinant Lkt carrier protein as described above.

TABLE 1

| Construct Design and Notation | Peptide Sequence | Epitope Presentation | Sequence |
|---|---|---|---|
| β2(2 + YYR + 9)I | QVYYRPVDQYSNQN (SEQ ID NO: 24) | (→←←)$_4$ | QVYYRPVDQYSNQNNQNSYQDVPR YYVQNQNSYQDVPRYYVQQVYYRP VDQYSNQNNQNSYQDVPRYYVQNQ NSYQDVPRYYVQQVYYRPVDQYSN QNNQNSYQDVPRYYVQNQNSYQDV PRYYVQQVYYRPVDQYSNQNNQNS YQDVPRYYVQNQNSYQDVPRYYVQ (SEQ ID NO: 25) |
| β2(2 + YYR + 8)I | QVYYRPVDQYSNQ (SEQ ID NO: 26) | (→←←)$_4$ | QVYYRPVDQYSNQQNSYQDVPRYY VQQNSYQDVPRYYVQQVYYRPVDQ YSNQQNSYQDVPRYYVQQNSYQDV PRYYVQQVYYRPVDQYSNQQNSYQ DVPRYYVQQNSYQDVPRYYVQQVY YRPVDQYSNQQNSYQDVPRYYVQQ NSYQDVPRYYVQ (SEQ ID NO: 27) |
| β2(2 + YYR + 7)I | QVYYRPVDQYSN (SEQ ID NO: 28) | (→←←)$_4$ | QVYYRPVDQYSNNSYQDVPRYYVQ NSYQDVPRYYVQQVYYRPVDQYSN NSYQDVPRYYVQNSYQDVPRYYVQ QVYYRPVDQYSNNSYQDVPRYYVQ NSYQDVPRYYVQQVYYRPVDQYSN NSYQDVPRYYVQNSYQDVPRYYVQ (SEQ ID NO: 29) |
| β2(2 + YYR + 6)I | QVYYRPVDQYS (SEQ ID NO: 30) | (→←←)$_4$ | QVYYRPVDQYSSYQDVPRYYVQSY QDVPRYYVQQVYYRPVDQYSSYQD VPRYYVQSYQDVPRYYVQQVYYRP VDQYSSYQDVPRYYVQSYQDVPRY YVQQVYYRPVDQYSSYQDVPRYYV QSYQDVPRYYVQ (SEQ ID NO: 31) |
| β2(2 + YYR + 5)I | QVYYRPVDQY (SEQ ID NO: 32) | (→←←)$_4$ | QVYYRPVDQYYQDVPRYYVQYQDV PRYYVQQVYYRPVDQYYQDVPRYY VQYQDVPRYYVQQVYYRPVDQYYQ DVPRYYVQYQDVPRYYVQQVYYRP VDQYYQDVPRYYVQYQDVPRYYVQ (SEQ ID NO: 33) |

TABLE 1-continued

| Construct Design and Notation | Peptide Sequence | Epitope Presentation | Sequence |
|---|---|---|---|
| β2(2 + YYR + 4)I | QVYYRPVDQ (SEQ ID NO: 34) | (→←←)$_4$ | QVYYRPVDQQDVPRYYVQQDVPRY YVQQVYYRPVDQQDVPRYYVQQDV PRYYVQQVYYRPVDQQDVPRYYVQ QDVPRYYVQQVYYRPVDQQDVPRY YVQQDVPRYYVQ (SEQ ID NO: 35) |
| β2(2 + YYR + 3)I | QVYYRPVD (SEQ ID NO: 36) | (→←←)$_4$ | QVYYRPVDDVPRYYVQDVPRYYVQ QVYYRPVDDVPRYYVQDVPRYYVQ QVYYRPVDDVPRYYVQDVPRYYVQ QVYYRPVDDVPRYYVQDVPRYYVQ (SEQ ID NO: 37) |

Example 2

Immunization of Mice with LKT-YYR Vaccines

The above expanded sequences were formulated into vaccines as described above, at identical doses and formulations, and were used to immunize C57BL6 mice (n=8) three times, at three week intervals. Antibody responses specific to each epitope were quantified over a 10-week time course with peptide-specific capture ELISAs. Among this panel of vaccine epitopes, there were marked differences in immunogenicity with the titre of epitope-specific antibody responses, ranging from titres of 100,000 to 2,000 (FIG. 4A). Within each experimental group, there was a varying degree of consistency of peptide-specific antibody responses; highly immunogenic constructs produced a highly consistent response and poorly immunogenic constructs produced a broader range of responses within the experimental group (FIG. 4B). Importantly, there was no significant correlation between epitope length and the magnitude of epitope-specific antibody responses; the immunogenicity of a peptide epitope is determined by a variety of sequence based factors. For example, the shortest peptide, 2+YYR+3, induced the highest peak antibody responses. The magnitude of the response to this epitope was significantly ($p<0.01$) higher than for the vaccines containing the longer epitopes (FIG. 4B). It was also apparent that small differences in epitope sequence had a significant influence on immunogenicity, as determined by the presence or absence of a substantial antibody response. For example, the 2+YYR+4 construct was significantly ($p<0.01$) more immunogenic than the 2+YYR+5 construct with over a 35-fold difference in antibody titres, and an increase in the proportion of responders from 38% to 100%; a consequence of the addition of only one amino acid (FIGS. 4A and 4B). This panel of vaccine epitopes, and the associated antibody responses, highlighted the importance of peptide optimization for immunogenicity as well as the dramatic impact made by small differences in peptide sequence.

Example 3

Production of Expanded YML and RL Epitopes

Through thermodynamic algorithms for predicting protein misfolding two additional regions of PrP were identified as exhibiting properties consistent with increased likelihood of surface exposure in the misfolded conformation of $PrP^{Sc}$. These epitopes correspond to the YML sequence of β-sheet 1 and a distinctive rigid loop linking β-sheet 2 to α-helix 2. The sequences and positioning of the three described prion DSEs (YYR, YML and RL), with respect to the primary structure of $PrP^C$, are presented in FIG. 1 (bolded).

Beginning with the YML DSE, preliminary non-optimized YML iterations, produced using the screening method described for the YYR epitope, lacked sufficient immunogenicity to induce an antibody response. As such, it was necessary to optimize the core sequence to increase immunogenicity, using a more systematic approach, as described in the materials and methods. Through this approach the expansion (1+YML+7—GYMLGSAMSRP, SEQ ID NO:17) was created and was highly immunogenic. The epitope presentation in this construct was (→←←)$_4$ and had the sequence GYMLGSAMSRPPRSMASGLMYGPRS-MASGLMYG GYMLGSAMSRPPRSMASGLMYGPRS-MASGLMYGGYMLGSAMSRPPRSMASGLMY GPRS-MASGLMYGGYMLGSAMSRPPRSMASGLMYGPRS-MASGLMYG (SEQ ID NO:38). In contrast, previously tested non-optimized sequence expansions corresponding to 2+YML+9 (GGYMLGSAMSRPLI, SEQ ID NO:39) and 9+YML+2 (GAVVGGLGGYMLGS, SEQ ID NO:40) induced weak immune responses. The expansion sequences of 2+YML+9 and 9+YML+2 also had the formula (→←←)$_4$. The expanded sequence of 2+YML+9 was GGYMLGSAMSRPLIILPRSMASGLMYGGGGYMLG-SAMSRPLIILPRSMASGLMYGG GGYMLGSAMSRPLI-ILPRSMASGLMYGG GGYMLGSAMSRPLIILPRSMAS-GLMYGG (SEQ ID NO:41). The expanded sequence of 9+YML+2 was GAVVGGLGGYMLGSSGLMYGGLGGV VAGGAV-VAGGAVVGGLGGYMLGSSGLMYGGLGGV VAGGAV-VGGLGGYMLGSSGLMYGGLGGVVAGGAVVGGLG-GYMLGSSGLMYGGL GGVVAG (SEQ ID NO:42).

The series of epitopes above was created in the context of C-terminal fusions with the recombinant Lkt carrier protein as described above.

A similar approach was employed for the RL DSE but in this case a single peptide epitope was selected for vaccine production, corresponding to 2+RL+4—VDQYSNQNNF (SEQ ID NO:19). The epitope presentation in this construct was (→←←)$_4$ and had the sequence VDQYSNQNNFFN-NQNSYQDVVDQYSNQNNFFNNQNSYQDVVDQYSN-QNNFFNNQ NSYQDVVDQYSNQNNFFNNQNSYQDV (SEQ ID NO:43) that was predicted to be highly immunogenic.

Example 4

Immunization of Mice with LKT-YML and RL Vaccines

Figure 6:
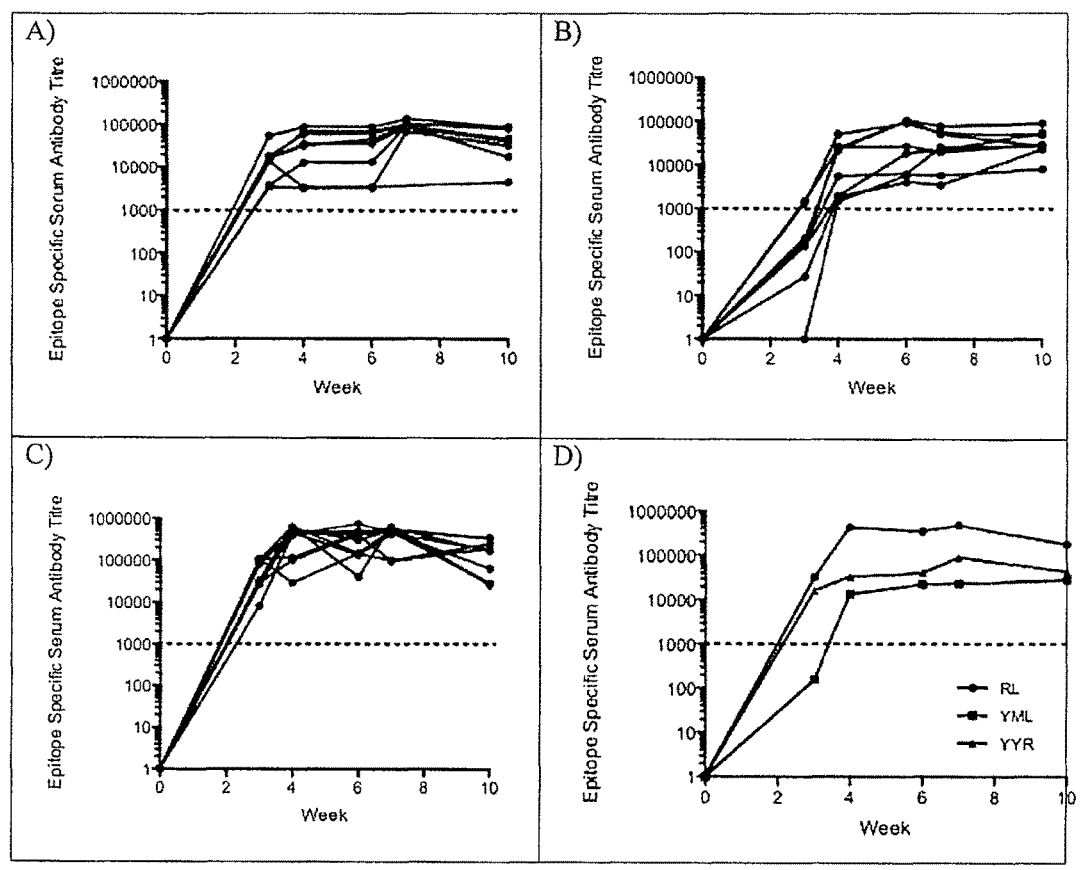

The above expanded sequences were formulated into vaccines as described above, at identical doses and formulations, and were used to immunize mice (n=8) three times, at three week intervals. Serum antibody responses to each epitope were determined with peptide capture ELISAs over a 10-week time-course. The 1+YML+7 vaccine induced the highest antibody responses while the vaccines containing non-optimized peptide epitopes induced low antibody responses. See, FIGS. 5A and 5B. Specifically, the 1+YML+7 vaccine induced significantly higher antibody responses (p<0.001) than the constructs predicted to be weakly immunogenic. There was a 100 to 1000-fold difference in antibody responses when comparing among the peptide epitopes. Notably, the optimization of the YML epitope dramatically improved the proportion of animals that generated an antibody response from 0% to 100%, based on our threshold for a positive response, at a titre of 1000. The RL peptide was also highly immunogenic. Individual animal antibody titres are presented in FIGS. 6A-6D for YYR (FIG. 6A), YML (FIG. 6B), and RL (FIG. 6C). Median titres for each DSE vaccine are compared in FIG. 6D. The dashed line indicates the threshold for a positive response, at a titre of 1000.

Example 5

Univalent Versus Multivalent Vaccination

The immunogenicity of the expanded epitope, multiple repeat vaccines described above Lkt-YML (1+YML+7 vaccine,), Lkt-YYR (2+YYR+3 vaccine) and Lkt-RL (2+RL+4 vaccine) were assessed in a large animal species. Groups of sheep (n=8) received 3 injections at 6 week intervals of either the Lkt-YML, Lkt-YYR, or Lkt-RL vaccines. Additionally, two groups of sheep (n=8) were separately injected with each of the three DSE vaccines, or the three DSE vaccines were co-formulated and injected at a single site. These two groups were included to determine if there were possible interactions among the three DSEs that may alter their immunogenicity. Serum antibody responses were monitored every three weeks using peptide capture ELISAs.

With each vaccination strategy (univalent, multivalent co-administered and multivalent co-formulated) there were consistent epitope-specific serum antibody responses in all animals within each group (FIG. 7A), but epitope specific antibody titres varied significantly among the three DSEs. The RL DSE was consistently found to exhibit the highest immunogenicity in all formulations. In the univalent vaccine format, the RL epitope induced stronger epitope-specific antibody responses than YYR (p<0.05), however the increase in immunogenicity compared to YML was found to be insignificant. For both multivalent vaccine formulations, the RL epitope was more immunogenic than both YYR and YML (p<0.001). The YML and YYR epitope-specific serum antibody titres were found to be significantly different only in the multivalent co-formulated vaccine where YYR was more immunogenic than YML (p<0.05) (FIG. 5B).

In addition, vaccine formulation and delivery significantly altered antibody responses to each DSE epitope (YYR, p<0.0001; YML, p<0.0001; RL, p=0.0413). The greatest effect on the antibody response was observed with the YYR and YML vaccines. For both DSE vaccines, co-formulation resulted in a significant decrease in the antibody response generated (p<0.01-p<0.001), when compared to the univalent and multivalent co-administered vaccines. There was no significant difference between the univalent and multivalent co-administered formulations. In contrast to YYR and YML, the antibody response generated against the RL vaccine was less sensitive to manipulations in vaccine formulation. The multivalent co-administered format generated an antibody response significantly greater than the multivalent co-formulated vaccine (p<0.05). However, this response was not significantly greater than the antibody response to the univalent vaccine and there was no significant difference between the univalent and the multivalent co-administered vaccines.

When comparing the two approaches to multivalent vaccine delivery, co-delivery at separate sites induced significantly greater antibody responses for all three DSEs than co-formulation. In addition, when comparing univalent and multivalent co-delivery, there is no significant effect on the antibody response to each DSE when the three vaccines are co-administered (FIG. 5C).

Example 6

Mucosal Responses to Vaccination

Figure 8:
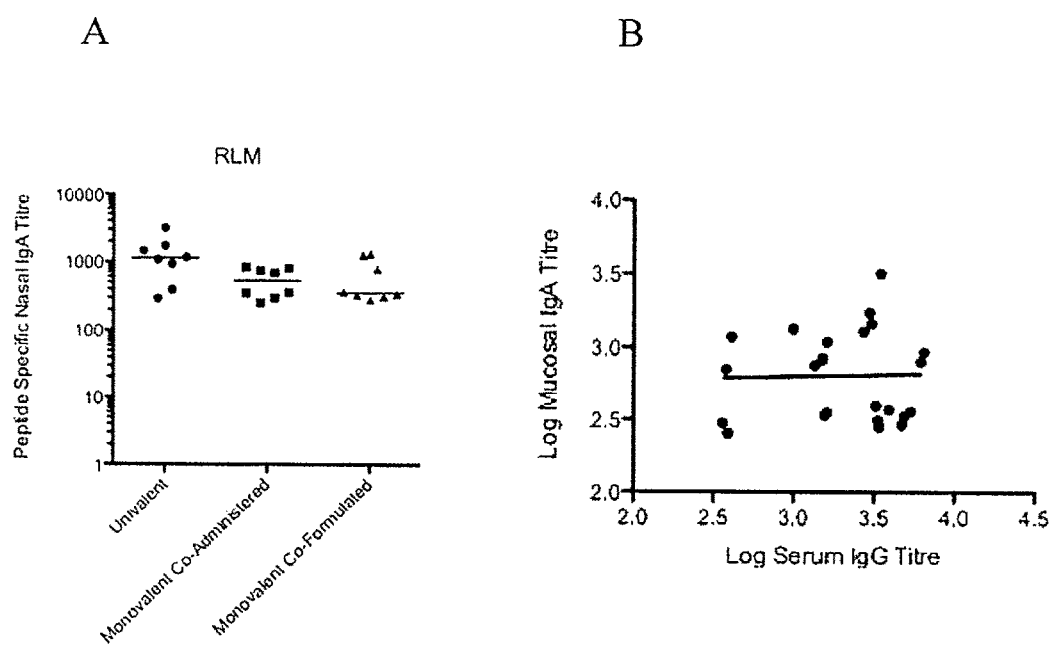

There is evidence for the uptake and amplification of prions at mucosal surfaces including the upper respiratory tract (tonsils) and intestine (Peyer's patches) (Heggebo et al., *J. Comp. Pathol.* (2003) 128:172-181), which consequently act as sites for neural invasion (Andreoletti et al., *J. Gen. Virol.* (2000) 81:3115-3126). Therefore, the generation of antibodies at these critical sites facilitates neutralization of the infectious $PrP^{Sc}$ prior to amplification and neural invasion. Peptide-specific antibody responses at a mucosal site (nasal secretions) were quantified following vaccination. Sheep (n=8) were immunized 3 times at 6-week intervals, with an additional boost at week 21. Nasal secretions were collected at week 23. Peptide-specific capture ELISAs confirmed the presence of epitope-specific antibody responses in the mucosal secretions of animals receiving the Lkt-RL vaccine in the univalent, multivalent co-administered, and multivalent co-formulated formats (FIGS. 8A-8B). There was no significant correlation (r2=0.0008541, p=0.8922) between serum IgG antibody titres and peptide-specific IgA antibody in mucosal secretions. The optimization of the DSEs resulted in a low but detectable level of antibody titres at the mucosal surface.

Example 7

Antibody Specificity

A major concern when expanding an epitope is the potential for conformational specificity to be compromised. The magnitude of the antibody responses against each DSE was significantly enhanced through the expansion based strategy described herein. However, antibody specificity must be thoroughly examined when this method is employed to ensure that gains in immunogenicity are not at the expense of specificity.

Antibody specificity was investigated using an ELISA to compare the reactivity of pre-immune and peak immune sera with recombinant $PrP^C$. Two possible mechanisms for generating antibody reactivity to $PrP^C$ were considered: $PrP^C$ reactivity could result either from one of the expanded epitopes, or a portion of one of the expanded epitopes, being surface exposed on $PrP^C$ or through epitope spreading from the $PrP^C$-DSE regions to other portions of the protein. In either scenario there was also the possibility that the vaccines, and the induced antibodies, might not function independently of each other at either a structural or immunological level. For instance, one antibody binding to its epitope may influence the structure of the protein to reveal protein regions that would normally not be surface exposed. Similarly, at an immunological level, the presence of multiple epitopes, representing a large portion of the protein, may facilitate epitope spreading.

Figure 7:
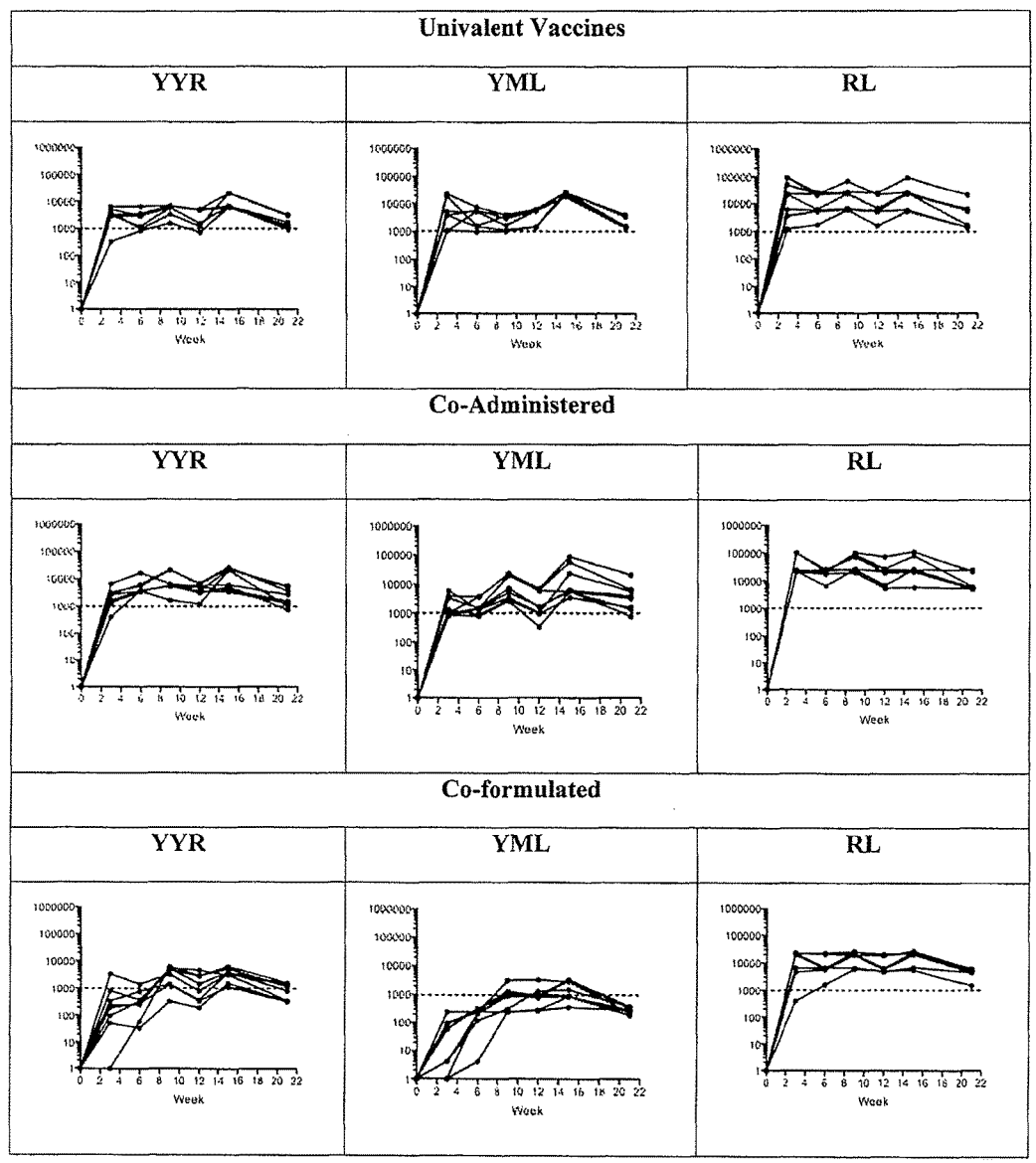

All of the animals that received the univalent DSE vaccines demonstrated no difference in $PrP^C$ recognition between the pre-immune and post-vaccination serum (FIG. 7). The absence of reactivity validates that these targets do, in fact, represent disease specific epitopes and that, individually, the conformational specificity of these targets has not been compromised by the expansions of the core DSE sequences in the univalent format. Interestingly, there was one animal in each of the co-administered and co-formulated multivalent vaccine groups that displayed low-level responses to $PrP^C$. These titres were above the pre-serum levels and the reaction was reproducible in independent ELISA tests. Subsequently, samples representing the full time-course for each of the positive animals were assessed for reactivity against $PrP^C$. Both animals displayed $PrP^C$ reactivity throughout the trial, which peaked following each immunization.

Figure 9:
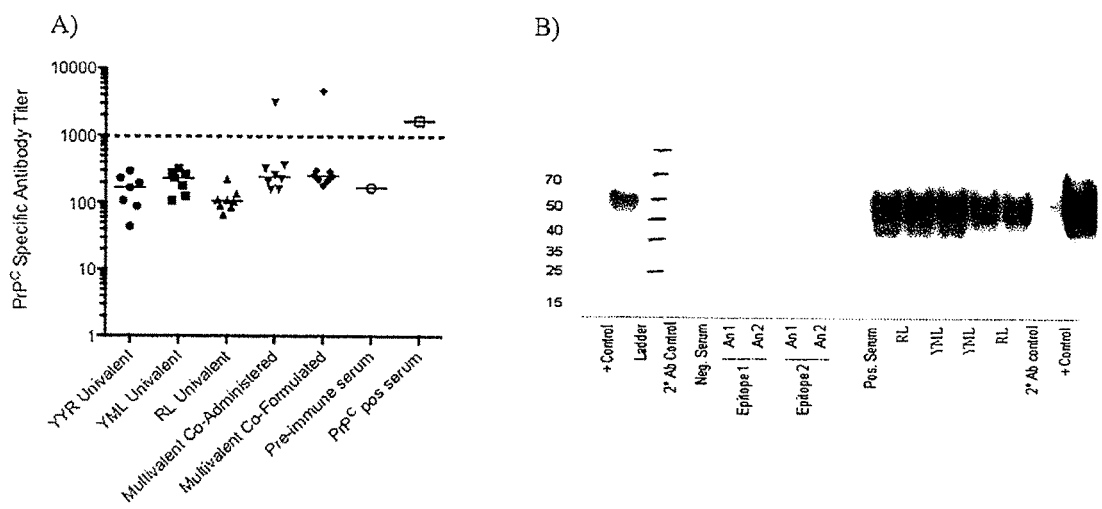

The conformational specificity of the antibodies generated against the YML, YYR, and RL epitopes was further examined by immunoprecipitation of $PrP^C$ from non-infected and $PrP^{Sc}$ from infected brain homogenate (FIG. 9). The DSE antibodies were cross-linked to magnetic beads and incubated with non-infected and infected 10% brain homogenate. Magnetic beads coated with 6D11 monoclonal antibody or naïve sheep serum were included as positive and negative controls, respectively. The peptide specific serum antibodies, generated in response to the univalent vaccines, preferentially bind $PrP^{Sc}$ with YML serum displaying a very minimal reactivity against $PrP^C$ at longer exposure times.

Example 8

Antibody-Induced Misfolding of $PrP^C$

One concern in the generation of antibodies against $PrP^{Sc}$, is the possibility that these antibodies may be capable of initiating template-directed misfolding of endogenous $PrP^C$, through stabilization of the misfolded structure. The ability of the DSE based vaccines to facilitate template-directed misfolding was examined both in vitro and in vivo. No symptoms of scrapie were observed in the sheep in all vaccinated groups up to collection, 23 weeks after their first vaccination. Obex and cerebellum samples from three sheep immunized with the multivalent co-administered vaccine were assayed for the presence of Proteinase K (PK) resistant $PrP^{Sc}$. This vaccine group was selected as the animals received a higher total vaccine dose (50 µg×3/dose) compared to the univalent vaccine group (50 µg/dose), and also generated a greater total $PrP^{Sc}$ specific antibody titre compared to the multivalent co-formulated vaccinated animals, which received the same total vaccine dose. No PK resistant $PrP^{Sc}$ could be detected after 1 hr of digest at a relatively low concentration of PK (20 µg/ml). IHC examination of obex, cerebellum, and rectal lymphoid follicles coupled with ELISA tests for PK resistant $PrP^{Sc}$ in obex and cerebellum were confirmed negative by Prairie Diagnostic Services (Saskatoon, SK). These results indicate that the multivalent co-administered vaccine did not induce formation of $PrP^{Sc}$ in vivo 23 weeks post vaccination.

To further determine if antibodies generated in response to the DSE vaccines could act as catalysts for the misfolding of $PrP^C$ to PK resistant $PrP^{Sc}$ in vitro, prebleed and post-vaccination sera from all vaccinated animals were pooled separately and applied to ovine brain homogenates. Homogenates and sera were incubated with shaking at 37° C. for 24 hrs to attempt conversion. PK resistant $PrP^{Sc}$ was undetectable in homogenates treated with both the prebleed and peak titre post-vaccination sera. These results demonstrate that the antibodies generated against DSEs of $PrP^{Sc}$ were unable to induce template-directed misfolding of $PrP^C$ to PK resistant $PrP^{Sc}$ both in vivo and in vitro under the conditions tested.

Thus, in the foregoing examples, the present inventors have demonstrated the efficient translation of newly predicted DSEs of the prion protein into peptide-based vaccines. As described herein, the immunogenicity of these vaccines, as well as the specificity for the misfolded form of the protein, were validated through vaccination trials. There is a strong possibility that a vaccine that targets multiple epitopes, while retaining $PrP^{Sc}$ specificity, is advantageous over a univalent vaccine. The above studies demonstrate the generation of a multivalent vaccine, based on the three prion DSEs, capable of inducing responses to each of these targets.

One concern regarding the use of $PrP^{Sc}$-specific vaccines is the potential for induction of disease in vaccinated animals, possibly through DSE antibody binding and stabilization of the misfolded structure. In this investigation, the antibodies generated following immunization with the DSE vaccines were incapable of facilitating template-directed conversion of $PrP^C$ into the PK-resistant isoform, both in vitro and in vivo, under the conditions tested. Notably, the generation of $PrP^{Sc}$ was absent in animals that received the maximum dose of DSE vaccine and generated the highest titres of DSE antibodies.

Currently, the only tools available for the control of prion diseases are management practises to limit the spread of this infectious agent through livestock animals. The inability of current management practises to significantly influence the spread of this disease is strong evidence for the need of new disease management tools for prions. There are no effective therapies or treatments that can be administered to an individual animal, such as antibiotics, to stop or even impact the inevitable disease-mediated death of the animal. Accordingly, the development of a vaccine for the prion diseases appears to be the most logical approach for disease management.

A number of groups have provided evidence of the potential for immunotherapy to protect animals from prion infection (White et al., Nature (2003) 422:80-83; Sigurdsson et al., Neurosci. Lett. (2003) 336:185-187; Sigurdsson et al., Am. J. Pathol. (2002) 161:13-17; Schwarz et al., Neurosci. Lett. (2003) 350:187-189). While encouraging, these investigations have typically induced immune responses in a manner in which the resulting antibodies do not discriminate the healthy and infectious conformations of the prion protein. There is evidence from in vitro investigations, as well as other examples in which induction of immune responses to a self-protein from a therapeutic perspective, has had adverse consequences. Furthermore, due to the inherent lack of PrP immunogenicity, these efforts often require very aggressive, complicated measures which limit the applicability of these approaches to real world vaccines.

While prion diseases are appropriately categorized as infectious diseases they also display many characteristics with cancer. Specifically, cancers and prion diseases share a common denominator of transformation of a normal, healthy component of the body into a malignant, pathological form. A central challenge in the treatment of cancer is the specificity of targeting of the disease-associated components while preserving the function of the normal, healthy cells.

Achieving this specificity is dependent upon the identification of disease-associated traits or biomarkers. Similarly, for the prion diseases, there is the potential for specific targeting of regions of the protein which are exposed upon misfolding; disease-specific epitopes. The strategy for targeted immunotherapy involves identification of these cryptic epitopes and their subsequent optimization and translation into vaccines capable of inducing an active immune response to an antigen derived from a self-protein.

With the expanded panel of vaccines, the inventors herein were successful in generating a strong conformation specific antibody response against three separate DSEs. Consequently, the PrP$^{Sc}$ specific antibodies generated by these vaccines can discriminate between the healthy and infectious conformations of PrP, potentially reducing the occurrence of adverse effects. In addition, the expanded sequences are highly conserved across a wide range of relevant species, including cattle, sheep, elk, deer, and humans, enabling the application of these to a variety of TSEs.

The PrP$^{Sc}$ specific antibodies induced by the described univalent and multivalent DSE vaccines have the potential to interfere with prion pathology through several mechanisms. The amplification of infectious PrP$^{Sc}$ requires an interaction between the infiltrating PrP$^{Sc}$ protein and endogenous PrP$^{C}$; PrP$^{Sc}$-specific antibodies may be capable of interfering with this process due to the localization of endogenous PrP$^{C}$ at or near the cell surface. Thus, if antibodies can inhibit this critical component of prion pathology, it may be possible for immunoprophylaxis to protect animals from prion infection following exposure to PrP$^{Sc}$. In addition, antibody binding specifically to PrP$^{Sc}$ may enhance cellular uptake and destruction of infectious prions by triggering Fc mediated effector functions, if activated before PrP$^{Sc}$ fully converts to the protease resistant isoform. Consequently, the reduction of PrP$^{Sc}$ formation and amplification within an infected animal may also lead to a reduction in PrP$^{Sc}$ shedding and subsequent disease transmission.

The misfolding of self-proteins is the basis for a variety of other neurodegenerative diseases including ALS, Alzheimer's and Parkinson's. Therefore, the current strategy for inducing immune responses against cryptic self-epitopes may have broad application for immunotherapy of protein misfolding diseases. In particular, the establishment of a rational pipeline in which predicted disease-specific epitopes can be optimized for immunogenicity and rapidly translated into established strategies of formulation and delivery of peptide-based vaccines has significant potential to advance the emerging field of conformation-specific immunotherapy of diseases associated with misfolding of self proteins.

Example 9 tgG-RL Fusions

Glycoprotein G (gG) of rabies virus (also known as lyssavirus G protein) is the primary antigen responsible for inducing protective virus-neutralizing antibodies. gG is present as both a truncated and membrane-bound isoform during natural rabies infections (Dietzschold et al., *Virol.* (1983) 124:330-337). The soluble form lacks carboxy-terminal amino acids coding for transmembrane and cytosolic domains present in the full-length protein. Although this truncation causes release of soluble gG from infected cells, the protein retains the quaternary structural conformation and immunogenicity of full-length gG (Gupta et al., *Vet. Microbiol.* (2005) 108:207-214; Wojczyk et al., *Glycobiol.* (1998) 8:121-130). The ability of full-length and truncated iterations of gG to induce humoral response against heterologous antigenic determinants of infectious pathogens has been investigated and immunization with constructs expressing chimeric proteins have been shown to induce strong humoral responses to both the heterologous peptide epitopes, as well as the gG carrier. See, Smith et al., *Virol.* (2006) 353:344-356 and Desmézières et al., *J. Gen. Virol.* (1999) 80:2343-2351

The magnitude, duration and isotype of antibody responses specific to an RL DSE expressed as a recombinant fusion with a truncated form of rabies glycoprotein G (tgG) depicted in FIG. 10 (SEQ ID NO:49) was investigated.

Materials and Methods for this study were as follows:

A. RL DSE:

The RL DSE used was a fusion of SEQ ID NO:19 with the epitope presentation of (→←←)$_4$ and including flanking and linking Gly and Ser amino acid residues (bolded), having the sequence:

(SEQ ID NO: 48)
GSVDQYSNQNNFFNNQNSYQDVFNNQNSYQDVSGSVDQYSNQNNFFNNQ

NSYQDVFNNQNSYQDVGSSVDQYSNQNNFFNNQNSYQDVFNNQNSYQDV

SGSVDQYSNQNNFFNNQNSYQDVFNNQNSYQDVSGS.

B. Leukotoxin Constructs:

The sequence encoding the RL DSE described above was subcloned into the modified version of pAA352 described above, to be expressed as C-terminal fusions to the LKT protein. All constructs were sequence verified (National Research Council Plant Biotechnology Institute, Saskatoon) and the resulting LKT-DSE recombinant fusion was produced in BL21 as described previously (Hedlin et al., Vaccine (2010):28:981-988; Gupta et al., *Vet. Microbiol.* (2005) 108:207-214). The recombinant fusion protein was produced and isolated as inclusion bodies and resolubilized in 4M Guanidine-HCl. The isolated protein was determined by denaturing polyacrylamide gel electrophoresis to be greater than 85% pure.

C. Generation of Truncated Rabies Glycoprotein G constructs:

The tgG molecule was produced as follows. Total RNA was isolated from rabies-positive fox brain tissue using RNeasy Mini Kit (Qiagen). A cDNA library was synthesized using Superscript III cDNA Library Construction Kit (Life Technologies). Truncated gG was synthesized by using appropriate primers to amplify the gene without the 3' nucleotides encoding the transmembrane and cytosolic domains. The produced gene was restricted and cloned into pEB4.3, a eukaryotic expression plasmid conferring puromycin resistance. The optimized rigid-loop (RL) peptide-epitope was amplified to facilitate C-terminal his-tag addition and subcloning into the pEB4.3-tgG plasmid. Sequence verified plasmid was transfected into HEK293T cells using X-tremeGENE HP DNA transfection reagent (Roche). Transfected cells were selected by the addition of 2 μg/mL puromycin to the culture medium. Cultures were subsequently transferred into HyClone SFM4HEK293 serum-free media (Thermo Scientific), incubated with light shaking, and maintained at a cell density of approximately 4×10$^6$ cells/mL. Recombinant his-tagged chimeric protein was purified from conditioned and clarified media by gravity flow chromatography using TALON Cobalt Affinity Resin (Clontech) following the manufacturers specifications for native purification conditions. Purified protein was identified by western blot and determined to be greater than 85% pure by SDS-PAGE.

D. Vaccine Formulation and Delivery:

C57/BL6 or BALB/c mice were injected subcutaneously with 10 µg of either Lkt-RL or tgG-RL formulated in a final volume of 100 µl phosphate buffered saline and 30% EMULSIGEN-D (MVP Technologies). Vaccines were administered as either a single dose, or as two separate immunizations on days 0 and 21.

E. Peptide Synthesis:

To detect peptide-specific antibody responses, peptides consisting of a single repeat motif for each DSE sequence were synthesized and verified as described in the Materials and Methods above.

F. ELISAs:

Serum epitope-specific antibody responses were quantified by ELISA, as previously described (Hedlin et al., Vaccine (2010) 28:981-988). Epitope-specific IgG antibody isotypes in serum collected 9 weeks after primary immunization were quantified by ELISA, as described previously (Huang et al., J. Gen. Virol. (2005) 86:997-898). ELISA titres were expressed as the reciprocal of the highest serum dilution resulting in an OD reading exceeding two standard deviations above the value for the pre-immune serum.

IFN-γ and IL-5 ELISPOT Assays:

Spleens were isolated from BALB/c mice (n=6) at 5 weeks post-immunization. Splenocyte isolation and culture, as well as ELISPOT plate preparation and development were described previously (Mapletoft et al., J. Gen. Virol. (2008) 89:250-260), with appropriate substitution of splenocyte-stimulating antigens. Stimulating antigens were added to three replicate splenocyte cultures and included: media control; RL peptide (1, 5, 10 µg/ml); tgG (0.1 and 1.0 µg/ml), and Lkt (0.1 and 1.0 µg/ml). Results were expressed as the number of cytokine-secreting cells per million cells in wells containing stimulatory antigen.

Statistical Analysis:

The data represents repeated measures of ELISA antibody titres in animals over time and did not adhere to a normal distribution. To account for the repeated measures study design, data for each animal were first summed over time. The data sums were then ranked to account for their non-normal distribution and then a one-way ANOVA analysis was performed on the ranked sums. Where appropriate, Tukey's test was used to examine differences among treatment groups. P values less than 0.05 were considered significant. All analysis met the assumptions of ANOVA.

Results were as follows.

Figure 11:
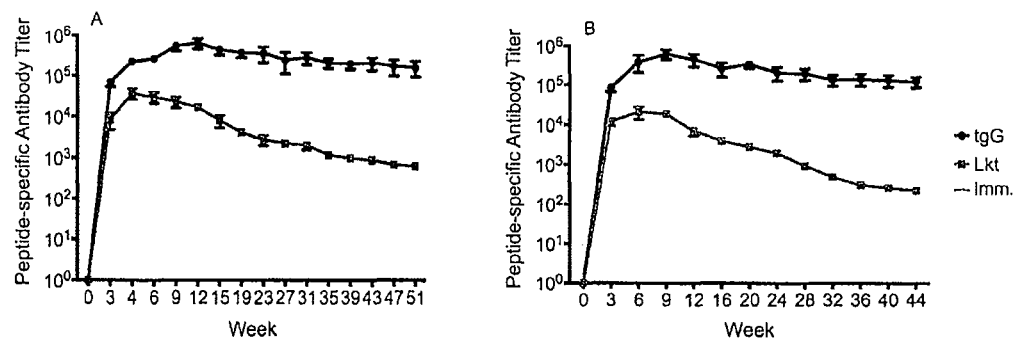

I. Magnitude and Duration of Antibody Responses:

Presentation of the PrP DSE peptide with either the Lkt or tgG carrier resulted in strong peptide-specific antibody responses. Peak titers induced by the tgG construct were over 10-fold higher than those induced by the Lkt-DSE fusion and following the peak response were often 100-fold higher (FIG. 11A). There was a clear difference in the duration of DSE-specific antibody responses following two immunizations with the tgG versus Lkt fusion proteins (FIG. 11A). DSE-specific antibody titers induced by the tgG fusion protein were maintained at a relatively constant level for one year. The duration of an antibody response may be a critical vaccine parameter, as this can influence the interval during which a vaccine provides a therapeutic benefit. The prolonged antibody response induced by the tgG carrier may reduce the need for booster vaccinations and reduce the cost of vaccination while providing a prolonged period of disease protection.

II. Single Immunization:

The capacity of each carrier protein construct to induce DSE-specific antibody responses following a single immunization was also investigated. Both carrier systems induced a marked rise in DSE-specific antibody titres within 3 weeks after the primary immunization (FIG. 11B). A similar difference in peak antibody tires was again observed, with the tgG-DSE fusion inducing a 10-fold greater antibody titer than the Lkt-DSE fusion and peptide-specific antibody responses were also maintained at a higher level following a single tgG-DSE fusion immunization. This experiment confirmed that a single immunization with the tgG-DSE fusion was sufficient to induce an antibody response that was sustained for over 44 weeks. From a practical perspective, there is considerable value in a vaccine technology capable of inducing a rapid and sustained antibody response following a single vaccination.

Figure 12:
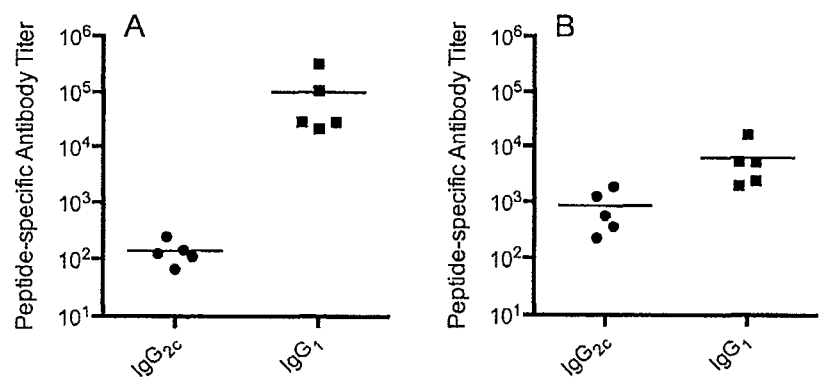
Figure 13:
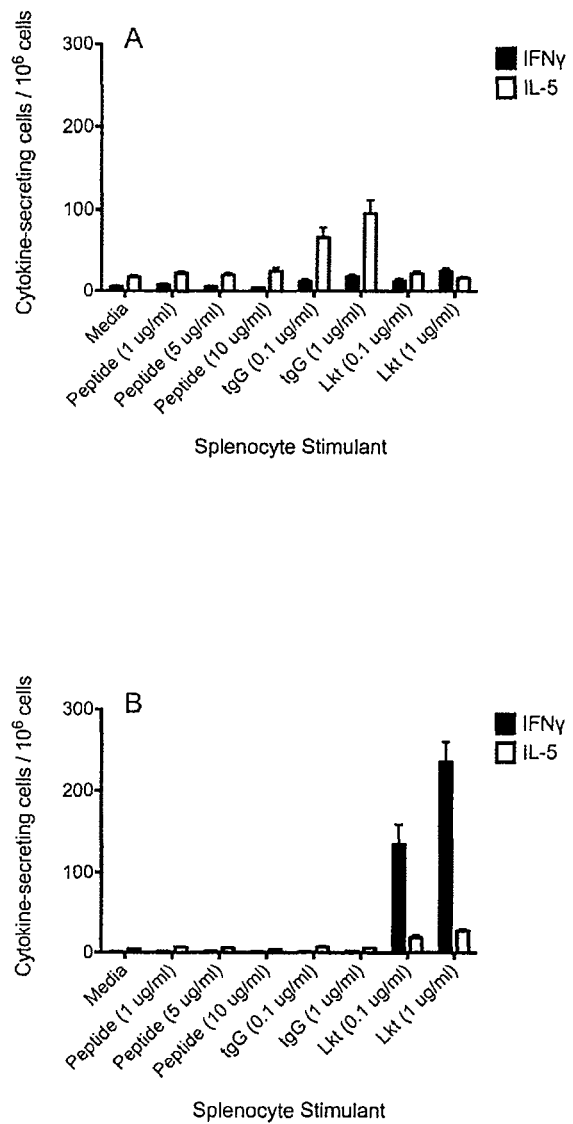

III. Antibody Isotype Bias:

The isotype of DSE-specific antibodies induced by each of the carrier proteins was further evaluated. Mice injected with the tgG-DSE fusion developed primarily an IgG1 antibody response (FIG. 12A) but mice injected with the Lkt-DSE fusion developed a balanced IgG1/IgG2c antibody response (FIG. 12B). This difference in antibody isotypes was further explored by analyzing splenocyte cytokine production following in vitro re-stimulation with both peptide antigen and carrier proteins. Restimulation with the DSE peptide did not induce detectable cytokine secretion which is consistent with the absence of a T cell epitope (FIG. 13). Re-stimulation with tgG protein induced primarily IL-5 secretion only in mice immunized with the tgG-DSE fusion (FIG. 13). In contrast, restimulation with Lkt protein induced primarily IFNγ secretion by splenocytes isolated from mice previously with the Lkt-DSE fusion (FIG. 13B). These observations support the conclusion that each carrier protein had a differential effect on T cell responses which was consistent with the bias observed for the isotype of DSE-specific antibodies. Therefore, it may be possible to use carrier proteins to influence the isotype of antibodies produced in response to peptide epitopes selected from self-proteins.

Thus, the present application describes prion expanded epitopes as well as methods of use thereof. Although preferred embodiments of the subject invention have been described in some detail, it is understood that obvious variations can be made without departing from the spirit and the scope of the invention as defined by the appended claims.

The invention claimed is:

1. A fusion peptide comprising three or more repeats of an immunogenic peptide, wherein the immunogenic peptide is selected from (a) a peptide comprising the sequence GYMLGSAMSRP (SEQ ID NO:17); (b) a peptide comprising the sequence VDQYSNQNNF (SEQ ID NO:19); or (c) a peptide comprising a sequence corresponding to GYMLGSAMSRP (SEQ ID NO:17) or VDQYSNQNNF (SEQ ID NO:19) from another non-bovine mammalian species,
    wherein one or more of the repeats is in an inverted orientation.

2. The fusion peptide of claim 1, wherein said fusion peptide comprises the amino acid sequence of SEQ ID NO:38.

3. The fusion peptide of claim 1, wherein said fusion peptide comprises the amino acid sequence of SEQ ID NO:43.

4. The fusion peptide of claim 1, wherein said fusion peptide comprises the amino acid sequence of SEQ ID NO:48.

5. The fusion peptide of claim 1, linked to a carrier molecule.

6. The fusion peptide of claim 5, wherein the carrier molecule is an RTX toxin characterized by a carboxy-terminus consensus amino acid sequence of Gly-Gly-X-Gly-X-Asp (SEQ ID NO: 11) wherein X is Lys, Asp, Val or Asn.

7. The fusion peptide of claim 6, wherein the carrier molecule is a leukotoxin polypeptide.

8. The fusion peptide of claim 7, wherein the leukotoxin polypeptide is leukotoxin (LKT) 352.

9. The fusion peptide of claim 5, wherein the carrier molecule is a lyssavirus glcoprotein G or a portion thereof comprising a deletion of all or part of the C-terminal transmembrane and cytoplasmic domains.

10. The fusion peptide of claim 9, wherein the lyssavirus glycoprotein G comprises the sequence of amino acids of SEQ ID NO:49.

11. A composition comprising the fusion peptide of claim 1, and a pharmaceutically acceptable vehicle.

12. The composition of claim 11 comprising a fusion peptide with the amino acid sequence of SEQ ID NO:38, and a fusion peptide with the amino acid sequence of SEQ ID NO:43 or SEQ ID NO:48.

13. The composition of claim 12, further comprising a fusion peptide with the amino acid sequence of SEQ ID NO:37.

14. A method of producing a composition comprising combining the fusion peptide of claim 1 with a pharmaceutically acceptable vehicle.

15. An immunodiagnostic test kit for detecting prion infection, said test kit comprising the fusion peptide according to claim 1, and instructions for conducting the immunodiagnostic test.

16. A method of eliciting an immune response to a prion in a mammal comprising administering to said mammal an immunologically effective amount of the composition of claim 11.

17. A method of detecting presence or absence of prion antibodies in a biological sample comprising:
   (a) providing a biological sample;
   (b) reacting said biological sample with the fusion peptide of claim 1 under conditions which allow prion antibodies, when present in the biological sample, to bind specifically to said fusion peptide to form an antibody-antigen complex; and
   (c) detecting the presence or the absence of said complex, thereby detecting the presence or the absence of the prion antibodies in said sample.

\* \* \* \* \*